United States Patent
Bhattacharjee et al.

(10) Patent No.: US 12,077,610 B2
(45) Date of Patent: *Sep. 3, 2024

(54) PEPTIDES AND OTHER AGENTS FOR TREATING PAIN AND INCREASING PAIN SENSITIVITY

(71) Applicant: The Research Foundation for The State University of New York, Amherst, NY (US)

(72) Inventors: Arindam Bhattacharjee, Buffalo, NY (US); Kerri Pryce, Amherst, NY (US)

(73) Assignee: THE RESEARCH FOUNDATION FOR THE STATE UNIVERSITY OF NEW YORK, Amherst, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/956,031

(22) Filed: Sep. 29, 2022

(65) Prior Publication Data

US 2023/0046305 A1 Feb. 16, 2023

Related U.S. Application Data

(63) Continuation of application No. 16/771,204, filed as application No. PCT/US2018/065545 on Dec. 13, 2018, now Pat. No. 11,535,649.

(60) Provisional application No. 62/598,067, filed on Dec. 13, 2017.

(51) Int. Cl.
*C07K 7/08* (2006.01)
*A61K 38/45* (2006.01)
*A61K 45/06* (2006.01)
*A61P 29/00* (2006.01)

(52) U.S. Cl.
CPC .............. *C07K 7/08* (2013.01); *A61K 38/45* (2013.01); *A61P 29/00* (2018.01); *A61K 45/06* (2013.01); *C12Y 207/04008* (2013.01)

(58) Field of Classification Search
None
See application file for complete search history.

(56) References Cited

U.S. PATENT DOCUMENTS

| | | | |
|---|---|---|---|
| 7,858,322 B2 | 12/2010 | Tymianski et al. | 435/7.1 |
| 8,143,005 B2 | 3/2012 | Rouleau et al. | |
| 8,691,783 B2 | 4/2014 | Thum et al. | 514/44 A |
| 9,241,970 B2 | 1/2016 | Tymianski | |
| 9,765,115 B2 | 9/2017 | Shah | |
| 11,535,649 B2 * | 12/2022 | Bhattacharjee | C07K 7/08 |
| 2003/0216310 A1 | 11/2003 | Thornton et al. | 424/139.1 |
| 2004/0180848 A1 | 9/2004 | Fesik et al. | |
| 2008/0069773 A1 | 3/2008 | Franco et al. | 424/9.2 |
| 2009/0087436 A1 | 4/2009 | Roch et al. | |
| 2009/0227533 A1 | 9/2009 | Bader et al. | |
| 2010/0088778 A1 | 4/2010 | Mulley et al. | 800/16 |
| 2014/0322307 A1 | 10/2014 | Ferrer Montiel et al. | |
| 2016/0222071 A1 | 8/2016 | Park et al. | |
| 2017/0081662 A1 | 3/2017 | Yu | |

FOREIGN PATENT DOCUMENTS

| | | |
|---|---|---|
| EP | 2307035 | 4/2011 |
| EP | 2593547 | 5/2013 |
| EP | 2616094 | 7/2013 |
| WO | WO/1998/011254 | 3/1998 |
| WO | WO/2000/056772 | 9/2000 |
| WO | WO/2003/029821 | 4/2003 |
| WO | WO/2003/087768 | 10/2003 |
| WO | WO/2004/045535 | 6/2004 |
| WO | WO/2006/040357 | 4/2006 |
| WO | WO/2009/059208 | 5/2009 |
| WO | WO/2010/034670 | 4/2010 |
| WO | WO/2017/147379 | 8/2017 |

OTHER PUBLICATIONS

MAGI-1 siRNA (h): sc-41999, Santa Cruz Biotechnology, Inc. Oct. 29, 2014.
Le, S. et al. (2011) "PSD95 Gene Specific siRNAs Attenuate Neuropathic Pain through Modulating Neuron Sensibility and Post-synaptic CaMKII(alpha) Phosphorylation," *Chinese Medical Sciences Journal* 26(4), 201-207.
Matsumoto, M. et al. (2015) "Channel Properties of Nax Expressed in Neurons," *PLoS One* 10(5), e0126109.
Nissen, K. B. et al. (2015) "Design, Synthesis, and Characterization of Fatty Acid Derivatives of a Dimeric Peptide-Based Postsynaptic Density-95 (PSD-95) Inhibitor," *Journal of Medicinal Chemistry* 58(3), 1575-1580.
Pryce, K. D. (2017) The scaffold protein Magi-1 regulates voltage-dependent sodium channels in dorsal rott ganglion neurons, in *Neuroscience Meeting Planner*, p. 2, Society for Neuroscience.
Pryce, K. D. (2018) Functional Regulation of Ion Channels in Dorsal Root Ganglion Neurons by Magi-1: Implications in Pain Signaling, p. 133, University at Buffalo.
Pryce, K. D. et al. (2019) "Magi-1 scaffolds Nav1-8 and Slack KNa channels in dorsal root ganglion neurons regulating excitability and pain," *FASEB Journal* 33(6), 7315-7330.
Rasband, M. N. (2010) "Clustered K+ channel complexes in axons," *Neuroscience Letters* 486(2), 101-106.

(Continued)

*Primary Examiner* — Sudhakar Katakam
*Assistant Examiner* — Zachary J Miknis
(74) *Attorney, Agent, or Firm* — Medlen & Carroll, LLP

(57) ABSTRACT

Described herein are peptides that can be used to treat pain or increase pain sensitivity in subject in need of treatment. Additionally, peptides of the present disclosure can be administered with an analgesic agent and/or anesthetic agent. Peptides of the present disclosure are suitable for use when a subject in need of treatment has an injury, a chronic disease, a chronic inflammation, Morton's neuroma, operative/post-operative pain, or a combination thereof.

10 Claims, 24 Drawing Sheets

Specification includes a Sequence Listing.

(56) References Cited

OTHER PUBLICATIONS

PCT International Search Report of International Application No. PCT/US2018/065545 dated Jun. 14, 2019.

\* cited by examiner

A.

| | | |
|---|---|---|
| *Xenopus* | RLELNDIVYLIRSDPLAHVANESHSRKSSNSYKTDPVGNPETRDETQL | SEQ ID NO:100 |
| chicken | RLELNDIVYLIRSDPLAHVANDGHSRKSSCSNKLGP-CNPETRDETQL | SEQ ID NO:101 |
| rat | RLEPNDIVYLIRSDPLAHVTSSQSRKSSCSNKLSS-CNPETRDETQL | SEQ ID NO:102 |
| human | RLEPSDIVYLIRSDPLAHVASSQSRKSSCSNKLSS-CNPETRDETQL | SEQ ID NO:103 |
| rat Slick | RLELNDVVYLIRPDPL----SYLPNSEPSRKNSICNAAVQDSREETQL | SEQ ID NO:104 |

D.

E.

»

A.

B.

C.

D.

E.

| | | | Residue # |
|---|---|---|---|
| rNav1.1 | SEQ ID NO:105 | STAACPPSYDRVTKP | 1978-1992 |
| rNav1.2 | SEQ ID NO:106 | PSTTSPPSYDSVTKP | 1967-1981 |
| rNav1.3 | SEQ ID NO:107 | SSTTSPPSYDSVTKP | 1913-1927 |
| rNav1.5 | SEQ ID NO:108 | SSTSFPPSYDSVTRA | 1972-1986 |
| rNav1.7 | SEQ ID NO:109 | ASTISPPSYDSVTKP | 1948-1962 |
| rNav1.8 | SEQ ID NO:110 | SATSFPPSYDSVTRG | 1912-1926 |
| rNav1.6 | SEQ ID NO:111 | PSTASLPSYDSVTKP | 1937-1951 |

SEQUENCE LISTING

```
Sequence total quantity: 114
SEQ ID NO: 1            moltype = AA  length = 15
FEATURE                 Location/Qualifiers
REGION                  1..15
                        note = Synthetic peptide
SITE                    1
                        note = MISC_FEATURE - The peptide of this residue is
                         optionally myristoylated.
source                  1..15
                        mol_type = protein
                        organism = synthetic construct
SEQUENCE: 1
STAACPPSYD RVTKP                                                        15

SEQ ID NO: 2            moltype = AA  length = 15
```

```
FEATURE              Location/Qualifiers
REGION               1..15
                     note = Synthetic peptide
SITE                 1
                     note = MISC_FEATURE - The residue at this position is
                      optionally phosphorylated.
source               1..15
                     mol_type = protein
                     organism = synthetic construct
SEQUENCE: 2
PSTTSPPSYD SVTKP                                                           15

SEQ ID NO: 3         moltype = AA  length = 15
FEATURE              Location/Qualifiers
REGION               1..15
                     note = Synthetic peptide
SITE                 1
                     note = MISC_FEATURE - The peptide of this residue is
                      optionally myristoylated.
source               1..15
                     mol_type = protein
                     organism = synthetic construct
SEQUENCE: 3
SSTTSPPSYD SVTKP                                                           15

SEQ ID NO: 4         moltype = AA  length = 15
FEATURE              Location/Qualifiers
REGION               1..15
                     note = Synthetic peptide
SITE                 1
                     note = MISC_FEATURE - The peptide of this residue is
                      optionally myristoylated.
source               1..15
                     mol_type = protein
                     organism = synthetic construct
SEQUENCE: 4
SSTSFPPSYD SVTRA                                                           15

SEQ ID NO: 5         moltype = AA  length = 15
FEATURE              Location/Qualifiers
REGION               1..15
                     note = Synthetic peptide
SITE                 1
                     note = MISC_FEATURE - The residue at this position is
                      optionally phosphorylated.
source               1..15
                     mol_type = protein
                     organism = synthetic construct
SEQUENCE: 5
PSTASLPSYD SVTKP                                                           15

SEQ ID NO: 6         moltype = AA  length = 15
FEATURE              Location/Qualifiers
REGION               1..15
                     note = Synthetic peptide
SITE                 1
                     note = MISC_FEATURE - The peptide of this residue is
                      optionally myristoylated.
source               1..15
                     mol_type = protein
                     organism = synthetic construct
SEQUENCE: 6
SSTTSPPSYD SVTKP                                                           15

SEQ ID NO: 7         moltype = AA  length = 15
FEATURE              Location/Qualifiers
REGION               1..15
                     note = Synthetic peptide
SITE                 1
                     note = MISC_FEATURE - The peptide of this residue is
                      optionally myristoylated.
source               1..15
                     mol_type = protein
                     organism = synthetic construct
SEQUENCE: 7
SATSFPPSYE SVTRG                                                           15

SEQ ID NO: 8         moltype = AA  length = 15
FEATURE              Location/Qualifiers
```

```
REGION                    1..15
                          note = Synthetic peptide
SITE                      1
                          note = MISC_FEATURE - The peptide of this residue is
                           optionally myristoylated.
SITE                      13
                          note = MISC_FEATURE - The peptide of this residue is
                           optionally phosphorylated.
source                    1..15
                          mol_type = protein
                          organism = synthetic construct
SEQUENCE: 8
STAACPPSYD RVTKP                                                              15

SEQ ID NO: 9              moltype = AA  length = 15
FEATURE                   Location/Qualifiers
REGION                    1..15
                          note = Synthetic peptide
SITE                      1
                          note = MISC_FEATURE - The residue at this position is
                           optionally phosphorylated.
SITE                      13
                          note = MISC_FEATURE - The peptide of this residue is
                           optionally phosphorylated.
source                    1..15
                          mol_type = protein
                          organism = synthetic construct
SEQUENCE: 9
PSTTSPPSYD SVTKP                                                              15

SEQ ID NO: 10             moltype = AA  length = 15
FEATURE                   Location/Qualifiers
REGION                    1..15
                          note = Synthetic peptide
SITE                      1
                          note = MISC_FEATURE - The peptide of this residue is
                           optionally myristoylated.
SITE                      13
                          note = MISC_FEATURE - The peptide of this residue is
                           optionally phosphorylated.
source                    1..15
                          mol_type = protein
                          organism = synthetic construct
SEQUENCE: 10
SSTTSPPSYD SVTKP                                                              15

SEQ ID NO: 11             moltype = AA  length = 15
FEATURE                   Location/Qualifiers
REGION                    1..15
                          note = Synthetic peptide
SITE                      1
                          note = MISC_FEATURE - The peptide of this residue is
                           optionally myristoylated.
SITE                      13
                          note = MISC_FEATURE - The peptide of this residue is
                           optionally phosphorylated.
source                    1..15
                          mol_type = protein
                          organism = synthetic construct
SEQUENCE: 11
SSTSFPPSYD SVTRA                                                              15

SEQ ID NO: 12             moltype = AA  length = 15
FEATURE                   Location/Qualifiers
REGION                    1..15
                          note = Synthetic peptide
SITE                      1
                          note = MISC_FEATURE - The residue at this position is
                           optionally phosphorylated.
SITE                      13
                          note = MISC_FEATURE - The peptide of this residue is
                           optionally phosphorylated.
source                    1..15
                          mol_type = protein
                          organism = synthetic construct
SEQUENCE: 12
PSTASLPSYD SVTKP                                                              15

SEQ ID NO: 13             moltype = AA  length = 15
```

```
FEATURE                  Location/Qualifiers
REGION                   1..15
                         note = Synthetic peptide
SITE                     1
                         note = MISC_FEATURE - The peptide of this residue is
                          optionally myristoylated.
SITE                     13
                         note = MISC_FEATURE - The peptide of this residue is
                          optionally phosphorylated.
source                   1..15
                         mol_type = protein
                         organism = synthetic construct
SEQUENCE: 13
SSTTSPPSYD SVTKP                                                              15

SEQ ID NO: 14            moltype = AA  length = 15
FEATURE                  Location/Qualifiers
REGION                   1..15
                         note = Synthetic peptide
SITE                     1
                         note = MISC_FEATURE - The peptide of this residue is
                          optionally myristoylated.
SITE                     13
                         note = MISC_FEATURE - The peptide of this residue is
                          optionally phosphorylated.
source                   1..15
                         mol_type = protein
                         organism = synthetic construct
SEQUENCE: 14
SATSFPPSYE SVTRG                                                              15

SEQ ID NO: 15            moltype = AA  length = 15
FEATURE                  Location/Qualifiers
REGION                   1..15
                         note = Synthetic peptide
SITE                     1
                         note = MISC_FEATURE - The peptide of this residue is
                          optionally myristoylated.
source                   1..15
                         mol_type = protein
                         organism = synthetic construct
SEQUENCE: 15
STAACPPSYD RVAKP                                                              15

SEQ ID NO: 16            moltype = AA  length = 15
FEATURE                  Location/Qualifiers
REGION                   1..15
                         note = Synthetic peptide
SITE                     1
                         note = MISC_FEATURE - The residue at this position is
                          optionally phosphorylated.
source                   1..15
                         mol_type = protein
                         organism = synthetic construct
SEQUENCE: 16
PSTTSPPSYD SVAKP                                                              15

SEQ ID NO: 17            moltype = AA  length = 15
FEATURE                  Location/Qualifiers
REGION                   1..15
                         note = Synthetic peptide
SITE                     1
                         note = MISC_FEATURE - The peptide of this residue is
                          optionally myristoylated.
source                   1..15
                         mol_type = protein
                         organism = synthetic construct
SEQUENCE: 17
SSTTSPPSYD SVAKP                                                              15

SEQ ID NO: 18            moltype = AA  length = 15
FEATURE                  Location/Qualifiers
REGION                   1..15
                         note = Synthetic peptide
SITE                     1
                         note = MISC_FEATURE - The peptide of this residue is
                          optionally myristoylated.
source                   1..15
                         mol_type = protein
```

```
                           organism = synthetic construct
SEQUENCE: 18
SSTSFPPSYD SVARA                                                           15

SEQ ID NO: 19              moltype = AA   length = 15
FEATURE                    Location/Qualifiers
REGION                     1..15
                           note = Synthetic peptide
SITE                       1
                           note = MISC_FEATURE - The residue at this position is
                            optionally phosphorylated.
source                     1..15
                           mol_type = protein
                           organism = synthetic construct
SEQUENCE: 19
PSTASLPSYD SVAKP                                                           15

SEQ ID NO: 20              moltype = AA   length = 15
FEATURE                    Location/Qualifiers
REGION                     1..15
                           note = Synthetic peptide
SITE                       1
                           note = MISC_FEATURE - The peptide of this residue is
                            optionally myristoylated.
source                     1..15
                           mol_type = protein
                           organism = synthetic construct
SEQUENCE: 20
SSTTSPPSYD SVAKP                                                           15

SEQ ID NO: 21              moltype = AA   length = 15
FEATURE                    Location/Qualifiers
REGION                     1..15
                           note = Synthetic peptide
SITE                       1
                           note = MISC_FEATURE - The peptide of this residue is
                            optionally myristoylated.
source                     1..15
                           mol_type = protein
                           organism = synthetic construct
SEQUENCE: 21
SATSFPPSYE SVARG                                                           15

SEQ ID NO: 22              moltype = AA   length = 15
FEATURE                    Location/Qualifiers
REGION                     1..15
                           note = Synthetic peptide
SITE                       1
                           note = MISC_FEATURE - The peptide of this residue is
                            optionally myristoylated.
source                     1..15
                           mol_type = protein
                           organism = synthetic construct
SEQUENCE: 22
STAACPPSYD RVEKP                                                           15

SEQ ID NO: 23              moltype = AA   length = 15
FEATURE                    Location/Qualifiers
REGION                     1..15
                           note = Synthetic peptide
SITE                       1
                           note = MISC_FEATURE - The residue at this position is
                            optionally phosphorylated.
source                     1..15
                           mol_type = protein
                           organism = synthetic construct
SEQUENCE: 23
PSTTSPPSYD SVEKP                                                           15

SEQ ID NO: 24              moltype = AA   length = 15
FEATURE                    Location/Qualifiers
REGION                     1..15
                           note = Synthetic peptide
SITE                       1
                           note = MISC_FEATURE - The peptide of this residue is
                            optionally myristoylated.
source                     1..15
                           mol_type = protein
                           organism = synthetic construct
```

```
SEQUENCE: 24
SSTTSPPSYD SVEKP                                                    15

SEQ ID NO: 25          moltype = AA  length = 15
FEATURE                Location/Qualifiers
REGION                 1..15
                       note = Synthetic peptide
SITE                   1
                       note = MISC_FEATURE - The peptide of this residue is
                        optionally myristoylated.
source                 1..15
                       mol_type = protein
                       organism = synthetic construct
SEQUENCE: 25
SSTSFPPSYD SVERA                                                    15

SEQ ID NO: 26          moltype = AA  length = 15
FEATURE                Location/Qualifiers
REGION                 1..15
                       note = Synthetic peptide
SITE                   1
                       note = MISC_FEATURE - The residue at this position is
                        optionally phosphorylated.
source                 1..15
                       mol_type = protein
                       organism = synthetic construct
SEQUENCE: 26
PSTASLPSYD SVEKP                                                    15

SEQ ID NO: 27          moltype = AA  length = 15
FEATURE                Location/Qualifiers
REGION                 1..15
                       note = Synthetic peptide
SITE                   1
                       note = MISC_FEATURE - The peptide of this residue is
                        optionally myristoylated.
source                 1..15
                       mol_type = protein
                       organism = synthetic construct
SEQUENCE: 27
SSTTSPPSYD SVEKP                                                    15

SEQ ID NO: 28          moltype = AA  length = 15
FEATURE                Location/Qualifiers
REGION                 1..15
                       note = Synthetic peptide
SITE                   1
                       note = MISC_FEATURE - The peptide of this residue is
                        optionally myristoylated.
source                 1..15
                       mol_type = protein
                       organism = synthetic construct
SEQUENCE: 28
SATSFPPSYE SVERG                                                    15

SEQ ID NO: 29          moltype = AA  length = 15
FEATURE                Location/Qualifiers
REGION                 1..15
                       note = Synthetic peptide
SITE                   1
                       note = MISC_FEATURE - The peptide of this residue is
                        optionally myristoylated.
source                 1..15
                       mol_type = protein
                       organism = synthetic construct
SEQUENCE: 29
STAACPPSYD RVDKP                                                    15

SEQ ID NO: 30          moltype = AA  length = 15
FEATURE                Location/Qualifiers
REGION                 1..15
                       note = Synthetic peptide
SITE                   1
                       note = MISC_FEATURE - The residue at this position is
                        optionally phosphorylated.
source                 1..15
                       mol_type = protein
                       organism = synthetic construct
SEQUENCE: 30
```

```
PSTTSPPSYD SVDKP                                                              15

SEQ ID NO: 31           moltype = AA  length = 15
FEATURE                 Location/Qualifiers
REGION                  1..15
                        note = Synthetic peptide
SITE                    1
                        note = MISC_FEATURE - The peptide of this residue is
                         optionally myristoylated.
source                  1..15
                        mol_type = protein
                        organism = synthetic construct
SEQUENCE: 31
SSTTSPPSYD SVDKP                                                              15

SEQ ID NO: 32           moltype = AA  length = 15
FEATURE                 Location/Qualifiers
REGION                  1..15
                        note = Synthetic peptide
SITE                    1
                        note = MISC_FEATURE - The peptide of this residue is
                         optionally myristoylated.
source                  1..15
                        mol_type = protein
                        organism = synthetic construct
SEQUENCE: 32
SSTSFPPSYD SVDRA                                                              15

SEQ ID NO: 33           moltype = AA  length = 15
FEATURE                 Location/Qualifiers
REGION                  1..15
                        note = Synthetic peptide
SITE                    1
                        note = MISC_FEATURE - The residue at this position is
                         optionally phosphorylated.
source                  1..15
                        mol_type = protein
                        organism = synthetic construct
SEQUENCE: 33
PSTASLPSYD SVDKP                                                              15

SEQ ID NO: 34           moltype = AA  length = 15
FEATURE                 Location/Qualifiers
REGION                  1..15
                        note = Synthetic peptide
SITE                    1
                        note = MISC_FEATURE - The peptide of this residue is
                         optionally myristoylated.
source                  1..15
                        mol_type = protein
                        organism = synthetic construct
SEQUENCE: 34
SSTTSPPSYD SVDKP                                                              15

SEQ ID NO: 35           moltype = AA  length = 15
FEATURE                 Location/Qualifiers
REGION                  1..15
                        note = Synthetic peptide
SITE                    1
                        note = MISC_FEATURE - The peptide of this residue is
                         optionally myristoylated.
source                  1..15
                        mol_type = protein
                        organism = synthetic construct
SEQUENCE: 35
SATSFPPSYE SVDRG                                                              15

SEQ ID NO: 36           moltype = AA  length = 15
FEATURE                 Location/Qualifiers
REGION                  1..15
                        note = Synthetic peptide
SITE                    1
                        note = MISC_FEATURE - The peptide of this residue is
                         optionally myristoylated.
source                  1..15
                        mol_type = protein
                        organism = synthetic construct
SEQUENCE: 36
STAACPPSYD RVTKP                                                              15
```

```
SEQ ID NO: 37           moltype = AA  length = 15
FEATURE                 Location/Qualifiers
REGION                  1..15
                        note = Synthetic peptide
SITE                    1
                        note = MISC_FEATURE - The residue at this position is
                         optionally phosphorylated.
source                  1..15
                        mol_type = protein
                        organism = synthetic construct
SEQUENCE: 37
PSTTSPPSYD SVTKP                                                            15

SEQ ID NO: 38           moltype = AA  length = 15
FEATURE                 Location/Qualifiers
REGION                  1..15
                        note = Synthetic peptide
SITE                    1
                        note = MISC_FEATURE - The peptide of this residue is
                         optionally myristoylated.
source                  1..15
                        mol_type = protein
                        organism = synthetic construct
SEQUENCE: 38
SSTTSPPSYD SVTKP                                                            15

SEQ ID NO: 39           moltype = AA  length = 15
FEATURE                 Location/Qualifiers
REGION                  1..15
                        note = Synthetic peptide
source                  1..15
                        mol_type = protein
                        organism = synthetic construct
SEQUENCE: 39
SSTSFPPSYD SVTRA                                                            15

SEQ ID NO: 40           moltype = AA  length = 15
FEATURE                 Location/Qualifiers
REGION                  1..15
                        note = Synthetic peptide
SITE                    1
                        note = MISC_FEATURE - The peptide of this residue is
                         optionally myristoylated.
source                  1..15
                        mol_type = protein
                        organism = synthetic construct
SEQUENCE: 40
SSTASLPSYD SVTKP                                                            15

SEQ ID NO: 41           moltype = AA  length = 15
FEATURE                 Location/Qualifiers
REGION                  1..15
                        note = Synthetic peptide
SITE                    1
                        note = MISC_FEATURE - The peptide of this residue is
                         optionally myristoylated.
source                  1..15
                        mol_type = protein
                        organism = synthetic construct
SEQUENCE: 41
SSTISPPSYD SVTKP                                                            15

SEQ ID NO: 42           moltype = AA  length = 15
FEATURE                 Location/Qualifiers
REGION                  1..15
                        note = Synthetic peptide
SITE                    1
                        note = MISC_FEATURE - The peptide of this residue is
                         optionally myristoylated.
source                  1..15
                        mol_type = protein
                        organism = synthetic construct
SEQUENCE: 42
SATSFPPSYD SVTRG                                                            15

SEQ ID NO: 43           moltype = AA  length = 15
FEATURE                 Location/Qualifiers
REGION                  1..15
```

```
                        note = Synthetic peptide
SITE                    1
                        note = MISC_FEATURE - The peptide of this residue is
                         optionally myristoylated.
SITE                    13
                        note = MISC_FEATURE - The peptide of this residue is
                         optionally phosphorylated.
source                  1..15
                        mol_type = protein
                        organism = synthetic construct
SEQUENCE: 43
STAACPPSYD RVTKP                                                                 15

SEQ ID NO: 44           moltype = AA  length = 15
FEATURE                 Location/Qualifiers
REGION                  1..15
                        note = Synthetic peptide
SITE                    1
                        note = MISC_FEATURE - The residue at this position is
                         optionally phosphorylated.
SITE                    13
                        note = MISC_FEATURE - The peptide of this residue is
                         optionally phosphorylated.
source                  1..15
                        mol_type = protein
                        organism = synthetic construct
SEQUENCE: 44
PSTTSPPSYD SVTKP                                                                 15

SEQ ID NO: 45           moltype = AA  length = 15
FEATURE                 Location/Qualifiers
REGION                  1..15
                        note = Synthetic peptide
SITE                    1
                        note = MISC_FEATURE - The peptide of this residue is
                         optionally myristoylated.
SITE                    13
                        note = MISC_FEATURE - The peptide of this residue is
                         optionally phosphorylated.
source                  1..15
                        mol_type = protein
                        organism = synthetic construct
SEQUENCE: 45
SSTTSPPSYD SVTKP                                                                 15

SEQ ID NO: 46           moltype = AA  length = 15
FEATURE                 Location/Qualifiers
REGION                  1..15
                        note = Synthetic peptide
SITE                    1
                        note = MISC_FEATURE - The peptide of this residue is
                         optionally myristoylated.
SITE                    13
                        note = MISC_FEATURE - The peptide of this residue is
                         optionally phosphorylated.
source                  1..15
                        mol_type = protein
                        organism = synthetic construct
SEQUENCE: 46
SSTSFPPSYD SVTRA                                                                 15

SEQ ID NO: 47           moltype = AA  length = 15
FEATURE                 Location/Qualifiers
REGION                  1..15
                        note = Synthetic peptide
SITE                    1
                        note = MISC_FEATURE - The peptide of this residue is
                         optionally myristoylated.
SITE                    13
                        note = MISC_FEATURE - The peptide of this residue is
                         optionally phosphorylated.
source                  1..15
                        mol_type = protein
                        organism = synthetic construct
SEQUENCE: 47
SSTASLPSYD SVTKP                                                                 15

SEQ ID NO: 48           moltype = AA  length = 15
FEATURE                 Location/Qualifiers
```

```
REGION                  1..15
                        note = Synthetic peptide
SITE                    1
                        note = MISC_FEATURE - The peptide of this residue is
                        optionally myristoylated.
SITE                    13
                        note = MISC_FEATURE - The peptide of this residue is
                        optionally phosphorylated.
source                  1..15
                        mol_type = protein
                        organism = synthetic construct
SEQUENCE: 48
SSTISPPSYD SVTKP                                                            15

SEQ ID NO: 49           moltype = AA  length = 15
FEATURE                 Location/Qualifiers
REGION                  1..15
                        note = Synthetic peptide
SITE                    1
                        note = MISC_FEATURE - The peptide of this residue is
                        optionally myristoylated.
SITE                    13
                        note = MISC_FEATURE - The peptide of this residue is
                        optionally phosphorylated.
source                  1..15
                        mol_type = protein
                        organism = synthetic construct
SEQUENCE: 49
SATSFPPSYD SVTRG                                                            15

SEQ ID NO: 50           moltype = AA  length = 15
FEATURE                 Location/Qualifiers
REGION                  1..15
                        note = Synthetic peptide
SITE                    1
                        note = MISC_FEATURE - The peptide of this residue is
                        optionally myristoylated.
source                  1..15
                        mol_type = protein
                        organism = synthetic construct
SEQUENCE: 50
STAACPPSYD RVAKP                                                            15

SEQ ID NO: 51           moltype = AA  length = 15
FEATURE                 Location/Qualifiers
REGION                  1..15
                        note = Synthetic peptide
SITE                    1
                        note = MISC_FEATURE - The residue at this position is
                        optionally phosphorylated.
source                  1..15
                        mol_type = protein
                        organism = synthetic construct
SEQUENCE: 51
PSTTSPPSYD SVAKP                                                            15

SEQ ID NO: 52           moltype = AA  length = 15
FEATURE                 Location/Qualifiers
REGION                  1..15
                        note = Synthetic peptide
SITE                    1
                        note = MISC_FEATURE - The peptide of this residue is
                        optionally myristoylated.
source                  1..15
                        mol_type = protein
                        organism = synthetic construct
SEQUENCE: 52
SSTTSPPSYD SVAKP                                                            15

SEQ ID NO: 53           moltype = AA  length = 15
FEATURE                 Location/Qualifiers
REGION                  1..15
                        note = Synthetic peptide
SITE                    1
                        note = MISC_FEATURE - The peptide of this residue is
                        optionally myristoylated.
source                  1..15
                        mol_type = protein
                        organism = synthetic construct
```

```
SEQUENCE: 53
SSTSFPPSYD SVARA                                                        15

SEQ ID NO: 54           moltype = AA  length = 15
FEATURE                 Location/Qualifiers
REGION                  1..15
                        note = Synthetic peptide
SITE                    1
                        note = MISC_FEATURE - The peptide of this residue is
                         optionally myristoylated.
source                  1..15
                        mol_type = protein
                        organism = synthetic construct
SEQUENCE: 54
SSTASLPSYD SVAKP                                                        15

SEQ ID NO: 55           moltype = AA  length = 15
FEATURE                 Location/Qualifiers
REGION                  1..15
                        note = Synthetic peptide
SITE                    1
                        note = MISC_FEATURE - The peptide of this residue is
                         optionally myristoylated.
source                  1..15
                        mol_type = protein
                        organism = synthetic construct
SEQUENCE: 55
SSTISPPSYD SVAKP                                                        15

SEQ ID NO: 56           moltype = AA  length = 15
FEATURE                 Location/Qualifiers
REGION                  1..15
                        note = Synthetic peptide
SITE                    1
                        note = MISC_FEATURE - The peptide of this residue is
                         optionally myristoylated.
source                  1..15
                        mol_type = protein
                        organism = synthetic construct
SEQUENCE: 56
SATSFPPSYD SVARG                                                        15

SEQ ID NO: 57           moltype = AA  length = 15
FEATURE                 Location/Qualifiers
REGION                  1..15
                        note = Synthetic peptide
SITE                    1
                        note = MISC_FEATURE - The peptide of this residue is
                         optionally myristoylated.
source                  1..15
                        mol_type = protein
                        organism = synthetic construct
SEQUENCE: 57
STAACPPSYD RVEKP                                                        15

SEQ ID NO: 58           moltype = AA  length = 15
FEATURE                 Location/Qualifiers
REGION                  1..15
                        note = Synthetic peptide
SITE                    1
                        note = MISC_FEATURE - The residue at this position is
                         optionally phosphorylated.
source                  1..15
                        mol_type = protein
                        organism = synthetic construct
SEQUENCE: 58
PSTTSPPSYD SVEKP                                                        15

SEQ ID NO: 59           moltype = AA  length = 15
FEATURE                 Location/Qualifiers
REGION                  1..15
                        note = Synthetic peptide
SITE                    1
                        note = MISC_FEATURE - The peptide of this residue is
                         optionally myristoylated.
source                  1..15
                        mol_type = protein
                        organism = synthetic construct
SEQUENCE: 59
```

```
SSTTSPPSYD SVEKP                                                                    15

SEQ ID NO: 60              moltype = AA   length = 15
FEATURE                    Location/Qualifiers
REGION                     1..15
                           note = Synthetic peptide
SITE                       1
                           note = MISC_FEATURE - The peptide of this residue is
                            optionally myristoylated.
source                     1..15
                           mol_type = protein
                           organism = synthetic construct
SEQUENCE: 60
SSTSFPPSYD SVERA                                                                    15

SEQ ID NO: 61              moltype = AA   length = 15
FEATURE                    Location/Qualifiers
REGION                     1..15
                           note = Synthetic peptide
SITE                       1
                           note = MISC_FEATURE - The peptide of this residue is
                            optionally myristoylated.
source                     1..15
                           mol_type = protein
                           organism = synthetic construct
SEQUENCE: 61
SSTASLPSYD SVEKP                                                                    15

SEQ ID NO: 62              moltype = AA   length = 15
FEATURE                    Location/Qualifiers
REGION                     1..15
                           note = Synthetic peptide
SITE                       1
                           note = MISC_FEATURE - The peptide of this residue is
                            optionally myristoylated.
source                     1..15
                           mol_type = protein
                           organism = synthetic construct
SEQUENCE: 62
SSTISPPSYD SVEKP                                                                    15

SEQ ID NO: 63              moltype = AA   length = 15
FEATURE                    Location/Qualifiers
REGION                     1..15
                           note = Synthetic peptide
SITE                       1
                           note = MISC_FEATURE - The peptide of this residue is
                            optionally myristoylated.
source                     1..15
                           mol_type = protein
                           organism = synthetic construct
SEQUENCE: 63
SATSFPPSYD SVERG                                                                    15

SEQ ID NO: 64              moltype = AA   length = 15
FEATURE                    Location/Qualifiers
REGION                     1..15
                           note = Synthetic peptide
SITE                       1
                           note = MISC_FEATURE - The peptide of this residue is
                            optionally myristoylated.
source                     1..15
                           mol_type = protein
                           organism = synthetic construct
SEQUENCE: 64
STAACPPSYD RVDKP                                                                    15

SEQ ID NO: 65              moltype = AA   length = 15
FEATURE                    Location/Qualifiers
REGION                     1..15
                           note = Synthetic peptide
SITE                       1
                           note = MISC_FEATURE - The residue at this position is
                            optionally phosphorylated.
source                     1..15
                           mol_type = protein
                           organism = synthetic construct
SEQUENCE: 65
PSTTSPPSYD SVDKP                                                                    15
```

```
SEQ ID NO: 66            moltype = AA   length = 15
FEATURE                  Location/Qualifiers
REGION                   1..15
                         note = Synthetic peptide
SITE                     1
                         note = MISC_FEATURE - The peptide of this residue is
                         optionally myristoylated.
source                   1..15
                         mol_type = protein
                         organism = synthetic construct
SEQUENCE: 66
SSTTSPPSYD SVDKP                                                          15

SEQ ID NO: 67            moltype = AA   length = 15
FEATURE                  Location/Qualifiers
REGION                   1..15
                         note = Synthetic peptide
SITE                     1
                         note = MISC_FEATURE - The peptide of this residue is
                         optionally myristoylated.
source                   1..15
                         mol_type = protein
                         organism = synthetic construct
SEQUENCE: 67
SSTSFPPSYD SVDRA                                                          15

SEQ ID NO: 68            moltype = AA   length = 15
FEATURE                  Location/Qualifiers
REGION                   1..15
                         note = Synthetic peptide
SITE                     1
                         note = MISC_FEATURE - The peptide of this residue is
                         optionally myristoylated.
source                   1..15
                         mol_type = protein
                         organism = synthetic construct
SEQUENCE: 68
SSTASLPSYD SVDKP                                                          15

SEQ ID NO: 69            moltype = AA   length = 15
FEATURE                  Location/Qualifiers
REGION                   1..15
                         note = Synthetic peptide
SITE                     1
                         note = MISC_FEATURE - The peptide of this residue is
                         optionally myristoylated.
source                   1..15
                         mol_type = protein
                         organism = synthetic construct
SEQUENCE: 69
SSTISPPSYD SVDKP                                                          15

SEQ ID NO: 70            moltype = AA   length = 15
FEATURE                  Location/Qualifiers
REGION                   1..15
                         note = Synthetic peptide
SITE                     1
                         note = MISC_FEATURE - The peptide of this residue is
                         optionally myristoylated.
source                   1..15
                         mol_type = protein
                         organism = synthetic construct
SEQUENCE: 70
SATSFPPSYD SVDRG                                                          15

SEQ ID NO: 71            moltype =    length =
SEQUENCE: 71
000

SEQ ID NO: 72            moltype = AA   length = 4
FEATURE                  Location/Qualifiers
REGION                   1..4
                         note = Synthetic peptide
source                   1..4
                         mol_type = protein
                         organism = synthetic construct
SEQUENCE: 72
TAAC                                                                       4
```

```
SEQ ID NO: 73          moltype = AA  length = 4
FEATURE                Location/Qualifiers
REGION                 1..4
                       note = Synthetic peptide
source                 1..4
                       mol_type = protein
                       organism = synthetic construct
SEQUENCE: 73
PPSY                                                                    4

SEQ ID NO: 74          moltype = AA  length = 6
FEATURE                Location/Qualifiers
REGION                 1..6
                       note = Synthetic peptide
source                 1..6
                       mol_type = protein
                       organism = synthetic construct
SEQUENCE: 74
DRVTKP                                                                  6

SEQ ID NO: 75          moltype =     length =
SEQUENCE: 75
000

SEQ ID NO: 76          moltype =     length =
SEQUENCE: 76
000

SEQ ID NO: 77          moltype = AA  length = 15
FEATURE                Location/Qualifiers
REGION                 1..15
                       note = Synthetic peptide
SITE                   1
                       note = MISC_FEATURE - The peptide of this residue is
                        optionally myristoylated.
SITE                   13
                       note = MISC_FEATURE - The peptide of this residue is
                        optionally phosphorylated.
source                 1..15
                       mol_type = protein
                       organism = synthetic construct
SEQUENCE: 77
SATSFPPSYD SVTRG                                                        15

SEQ ID NO: 78          moltype = AA  length = 4
FEATURE                Location/Qualifiers
REGION                 1..4
                       note = Synthetic peptide
source                 1..4
                       mol_type = protein
                       organism = synthetic construct
SEQUENCE: 78
PPRY                                                                    4

SEQ ID NO: 79          moltype = AA  length = 10
FEATURE                Location/Qualifiers
REGION                 1..10
                       note = Synthetic peptide
source                 1..10
                       mol_type = protein
                       organism = synthetic construct
SEQUENCE: 79
NPETRDETQL                                                              10

SEQ ID NO: 80          moltype = AA  length = 10
FEATURE                Location/Qualifiers
REGION                 1..10
                       note = Synthetic peptide
source                 1..10
                       mol_type = protein
                       organism = synthetic construct
SEQUENCE: 80
QPNTRLDETE                                                              10

SEQ ID NO: 81          moltype = AA  length = 14
FEATURE                Location/Qualifiers
REGION                 1..14
                       note = Synthetic peptide
```

```
source                     1..14
                           mol_type = protein
                           organism = synthetic construct
SEQUENCE: 81
SDRPVTSYSF SAPG                                                             14

SEQ ID NO: 82              moltype = DNA  length = 30
FEATURE                    Location/Qualifiers
misc_feature               1..30
                           note = Primer
source                     1..30
                           mol_type = other DNA
                           organism = synthetic construct
SEQUENCE: 82
gtcttcgagg gggccgagaa tataacatgg                                            30

SEQ ID NO: 83              moltype = DNA  length = 22
FEATURE                    Location/Qualifiers
misc_feature               1..22
                           note = Primer
source                     1..22
                           mol_type = other DNA
                           organism = synthetic construct
SEQUENCE: 83
ggtggagggg ccgttcctgt cg                                                    22

SEQ ID NO: 84              moltype = DNA  length = 21
FEATURE                    Location/Qualifiers
misc_feature               1..21
                           note = Primer
source                     1..21
                           mol_type = other DNA
                           organism = synthetic construct
SEQUENCE: 84
cccaaagggc agcaggagct g                                                     21

SEQ ID NO: 85              moltype = DNA  length = 22
FEATURE                    Location/Qualifiers
misc_feature               1..22
                           note = Primer
source                     1..22
                           mol_type = other DNA
                           organism = synthetic construct
SEQUENCE: 85
cggcgagtgc agccttctgt ga                                                    22

SEQ ID NO: 86              moltype = DNA  length = 24
FEATURE                    Location/Qualifiers
misc_feature               1..24
                           note = Primer
source                     1..24
                           mol_type = other DNA
                           organism = synthetic construct
SEQUENCE: 86
ctgccacaag tccaaaagtg tgaa                                                  24

SEQ ID NO: 87              moltype = DNA  length = 22
FEATURE                    Location/Qualifiers
misc_feature               1..22
                           note = Primer
source                     1..22
                           mol_type = other DNA
                           organism = synthetic construct
SEQUENCE: 87
agtcatcggg ctcgtccaga tc                                                    22

SEQ ID NO: 88              moltype = RNA  length = 21
FEATURE                    Location/Qualifiers
misc_feature               1..21
                           note = siRNA
source                     1..21
                           mol_type = other RNA
                           organism = synthetic construct
SEQUENCE: 88
ggaaagacag ccagaatagt t                                                     21

SEQ ID NO: 89              moltype = RNA  length = 21
FEATURE                    Location/Qualifiers
misc_feature               1..21
```

```
                        note = siRNA
source                  1..21
                        mol_type = other RNA
                        organism = synthetic construct
SEQUENCE: 89
gcccaagctc cagatcaaac t                                              21

SEQ ID NO: 90           moltype = RNA   length = 21
FEATURE                 Location/Qualifiers
misc_feature            1..21
                        note = siRNA
source                  1..21
                        mol_type = other RNA
                        organism = synthetic construct
SEQUENCE: 90
gtggatggga cgccagtaat t                                              21

SEQ ID NO: 91           moltype = RNA   length = 21
FEATURE                 Location/Qualifiers
misc_feature            1..21
                        note = siRNA
source                  1..21
                        mol_type = other RNA
                        organism = synthetic construct
SEQUENCE: 91
gaagcattct cgagctatag a                                              21

SEQ ID NO: 92           moltype = RNA   length = 21
FEATURE                 Location/Qualifiers
misc_feature            1..21
                        note = siRNA
source                  1..21
                        mol_type = other RNA
                        organism = synthetic construct
SEQUENCE: 92
gtttccccta ttcaccagtg t                                              21

SEQ ID NO: 93           moltype = RNA   length = 21
FEATURE                 Location/Qualifiers
misc_feature            1..21
                        note = siRNA
source                  1..21
                        mol_type = other RNA
                        organism = synthetic construct
SEQUENCE: 93
gcctctcgca ccatgtgatt a                                              21

SEQ ID NO: 94           moltype = RNA   length = 21
FEATURE                 Location/Qualifiers
misc_feature            1..21
                        note = siRNA
source                  1..21
                        mol_type = other RNA
                        organism = synthetic construct
SEQUENCE: 94
gaccaagagc gaaggaatgt t                                              21

SEQ ID NO: 95           moltype = RNA   length = 21
FEATURE                 Location/Qualifiers
misc_feature            1..21
                        note = siRNA
source                  1..21
                        mol_type = other RNA
                        organism = synthetic construct
SEQUENCE: 95
gttcctcaga tccaattgtt a                                              21

SEQ ID NO: 96           moltype = RNA   length = 21
FEATURE                 Location/Qualifiers
misc_feature            1..21
                        note = siRNA
source                  1..21
                        mol_type = other RNA
                        organism = synthetic construct
SEQUENCE: 96
gaccatctga gcccactact a                                              21

SEQ ID NO: 97           moltype = RNA   length = 21
FEATURE                 Location/Qualifiers
```

```
misc_feature            1..21
                        note = siRNA
source                  1..21
                        mol_type = other RNA
                        organism = synthetic construct
SEQUENCE: 97
ggaaacatgt gactataacct t                                              21

SEQ ID NO: 98           moltype = RNA  length = 21
FEATURE                 Location/Qualifiers
misc_feature            1..21
                        note = siRNA
source                  1..21
                        mol_type = other RNA
                        organism = synthetic construct
SEQUENCE: 98
gatcttaca tagcttagtg t                                                21

SEQ ID NO: 99           moltype = AA  length = 4
FEATURE                 Location/Qualifiers
REGION                  1..4
                        note = Synthetic peptide
source                  1..4
                        mol_type = protein
                        organism = synthetic construct
SEQUENCE: 99
ETQL                                                                  4

SEQ ID NO: 100          moltype = AA  length = 48
FEATURE                 Location/Qualifiers
source                  1..48
                        mol_type = protein
                        organism = Xenopus sp.
SEQUENCE: 100
RLELNDIVYL IRSDPLAHVA NESHSRKSSN SYKTDPVGNP ETRDETQL                  48

SEQ ID NO: 101          moltype = AA  length = 47
FEATURE                 Location/Qualifiers
source                  1..47
                        mol_type = protein
                        organism = Gallus gallus
SEQUENCE: 101
RLELNDIVYL IRSDPLAHVA NDGHSRKSSC SNKLGPCNPE TRDETQL                   47

SEQ ID NO: 102          moltype = AA  length = 47
FEATURE                 Location/Qualifiers
source                  1..47
                        mol_type = protein
                        organism = Rattus norvegicus
SEQUENCE: 102
RLEPNDIVYL IRSDPLAHVT SSSQSRKSSC SNKLSSCNPE TRDETQL                   47

SEQ ID NO: 103          moltype = AA  length = 47
FEATURE                 Location/Qualifiers
source                  1..47
                        mol_type = protein
                        organism = Homo sapiens
SEQUENCE: 103
RLEPSDIVYL IRSDPLAHVA SSSQSRKSSC SHKLSSCNPE TRDETQL                   47

SEQ ID NO: 104          moltype = AA  length = 44
FEATURE                 Location/Qualifiers
source                  1..44
                        mol_type = protein
                        organism = Rattus norvegicus
SEQUENCE: 104
RLELNDVVYL IRPDPLSYLP NSEPSRKNSI CNAAVQDSRE ETQL                      44

SEQ ID NO: 105          moltype = AA  length = 15
FEATURE                 Location/Qualifiers
source                  1..15
                        mol_type = protein
                        organism = Rattus norvegicus
SEQUENCE: 105
STAACPPSYD RVTKP                                                      15

SEQ ID NO: 106          moltype = AA  length = 15
FEATURE                 Location/Qualifiers
source                  1..15
```

```
                                   mol_type = protein
                                   organism = Rattus norvegicus
SEQUENCE: 106
PSTTSPPSYD SVTKP                                                           15

SEQ ID NO: 107           moltype = AA   length = 15
FEATURE                  Location/Qualifiers
source                   1..15
                         mol_type = protein
                         organism = Rattus norvegicus
SEQUENCE: 107
SSTTSPPSYD SVTKP                                                           15

SEQ ID NO: 108           moltype = AA   length = 15
FEATURE                  Location/Qualifiers
source                   1..15
                         mol_type = protein
                         organism = Rattus norvegicus
SEQUENCE: 108
SSTSFPPSYD SVTRA                                                           15

SEQ ID NO: 109           moltype = AA   length = 15
FEATURE                  Location/Qualifiers
source                   1..15
                         mol_type = protein
                         organism = Rattus norvegicus
SEQUENCE: 109
ASTISPPSYD SVTKP                                                           15

SEQ ID NO: 110           moltype = AA   length = 15
FEATURE                  Location/Qualifiers
source                   1..15
                         mol_type = protein
                         organism = Rattus norvegicus
SEQUENCE: 110
SATSFPPSYD SVTRG                                                           15

SEQ ID NO: 111           moltype = AA   length = 15
FEATURE                  Location/Qualifiers
source                   1..15
                         mol_type = protein
                         organism = Rattus norvegicus
SEQUENCE: 111
PSTASLPSYD SVTKP                                                           15

SEQ ID NO: 112           moltype = AA   length = 4
FEATURE                  Location/Qualifiers
source                   1..4
                         mol_type = protein
                         organism = Xenopus sp.
SEQUENCE: 112
ETQL                                                                        4

SEQ ID NO: 113           moltype = AA   length = 10
FEATURE                  Location/Qualifiers
REGION                   1..10
                         note = Synthetic peptide
SITE                     1
                         note = MISC_FEATURE - The peptide of this residue is
                          optionally myristoylated.
source                   1..10
                         mol_type = protein
                         organism = synthetic construct
SEQUENCE: 113
QPNTRLDETE                                                                 10

SEQ ID NO: 114           moltype = AA   length = 15
FEATURE                  Location/Qualifiers
source                   1..15
                         mol_type = protein
                         organism = synthetic construct
MOD_RES                  1
                         note = The residue at this position is optionally asylated
                          at a nucleophilic atom of the amino acid residue.
MOD_RES                  1
                         note = X1 - X1 is selected from the group consisting of S
                          P, and A
MOD_RES                  2
                         note = X2 - X2 is selected from the group consisting of T
```

```
                        S, and A
MOD_RES                 2
                        note = X2 - The residue at this position is optionally
                          asylated at a nucleophilic atom of the amino acid residue.
MOD_RES                 3
                        note = X3 - X3 is selected from the group consisting of A
                          and T.
MOD_RES                 3
                        note = X3 - The residue at this position is optionally
                          asylated at a nucleophilic atom of the amino acid residue.
MOD_RES                 4
                        note = X4 - X4 is selected from the group consisting of A
                          T, I, and S.
MOD_RES                 4
                        note = X4 - The residue at this position is optionally
                          asylated at a nucleophilic atom of the amino acid residue.
MOD_RES                 5
                        note = X5 - X5 is selected from the group consisting of C
                          S, and F
MOD_RES                 6
                        note = X6 - X6 is selected from the group consisting of P
                          and L
MOD_RES                 8
                        note = X7 - X7 is any amino acid residue.
MOD_RES                 10
                        note = X8 - X8 is selected from the group consisting of E,
                          D and Y.
MOD_RES                 11
                        note = X9 - X9 is selected from the group consisting of S
                          and R.
MOD_RES                 13
                        note = X10 - X10 is selected from the group consisting of
                          T, A, E, and D, and T is optionally phosphorylated.
MOD_RES                 13
                        note = X10 - The residue at this position is optionally
                          asylated at a nucleophilic atom of the amino acid residue.
MOD_RES                 14
                        note = X11 - X11 is selected from the group consisting of K
                          and R.
MOD_RES                 14
                        note = X11 - The residue at this position is optionally
                          asylated at a nucleophilic atom of the amino acid residue.
MOD_RES                 15
                        note = X12 - X12 is selected from the group consisting of P
                          A, and G.
SEQUENCE: 114
XXXXXPPSYX XVXXX                                                                    15
```

PEPTIDES AND OTHER AGENTS FOR TREATING PAIN AND INCREASING PAIN SENSITIVITY

CROSS REFERENCE TO RELATED APPLICATION

This application claims priority to co-pending U.S. application Ser. No. 16/771,204, filed on Jun. 9, 2020, which claims priority to PCT/US2018/065545, filed Dec. 13, 2018, which claims priority to U.S. Provisional Application No. 62/598,067, filed on Dec. 13, 2017, the disclosure of which is incorporated by reference.

STATEMENT REGARDING FEDERAL FUNDING

This invention was made with government support under Grant No. NS078184 awarded by National Institutes of Health. The government has certain rights in the invention.

REFERENCE TO AN ELECTRONIC SEQUENCE LISTING

The contents of the electronic sequence listing (20136.xml; Size: 170,572 bytes; and Date of Creation: Sep. 29, 2022) is herein incorporated by reference in its entirety.

BACKGROUND OF THE DISCLOSURE

Nociceptive neurons are endowed with a specific subset of voltage-dependent sodium channels ($Na_V$) allowing neurons to uniquely respond to noxious and inflammatory stimuli. Therefore, a current strategy for new analgesic development relies on targeting nociceptor-specific sodium channels. For example, the $Na_V1.8$ channel (SCN10A) has distinctive biophysical properties permitting nociceptive neurons to repetitively fire action potentials (AP) under compromised conditions associated with tissue damage. This has led to the clinical testing of $Na_V1.8$ channel specific blockers for pain relief. Because channels also traffic to the membrane during inflammatory signaling, an alternative approach to affect $Na_V1.8$ channel functioning would be to perturb their trafficking. However, the precise molecular mechanisms controlling $Na_V1.8$ channel trafficking are not completely understood and therefore, specific agents targeting $Na_V.8$ still remain elusive.

There is a continuing need for development of agents that act on $Na_V1.8$ channels to increase or decrease a subject's pain sensitivity.

SUMMARY OF THE DISCLOSURE

The present provides peptides, compositions, and methods of using these peptides and/or compositions to treat pain, induce analgesia, or increase pain sensitivity. In addition, the present disclosure provides methods of treating pain or inducing local analgesia by administering Magi-1 (Membrane-Associated Guanylate Kinase 1) targeting shRNA, or Magi-1 targeting siRNA. The present disclosure further provides peptides for use as research tools. Use of the peptides having the sequence of SEQ ID No. 1-35, Magi-1 targeting shRNA, or Magi-1 targeting siRNA will diminish or eliminate the need for narcotics to combat pain.

In an aspect, the present disclosure provides a peptide comprising or consisting of the following sequence:

$X^1X^2X^3X^4X^5X^6PX^7YX^8X^9VX^{10}X^{11}X^{12}$     (SEQ ID NO:75), wherein $X^1$ is S, P, or A; $X^2$ is T, S, or A; $X^3$ is A or T; $X^4$ is A, T, 1, or S; $X^5$ is C, S, or F; $X^6$ is P or L; $X^7$ is any amino acid residue, $X^8$ is E, D, or Y; $X^9$ is S or R; $X^{10}$ is T, A, E, or D, and T is optionally phosphorylated; $X^{11}$ is K or R; and $X^{12}$ is P, A, or G, and wherein $X^1$, $X^2$, $X^3$, $X^9$, $X^{10}$, $X^{11}$, or a combination thereof is acylated

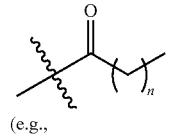

(e.g., )

and n is 4-18, (e.g., 4, 5, 6, 7, 8, 9, 10, 11, 12, 13, 14, 15, 16, 17, or 18). In a further embodiment, the acyl group

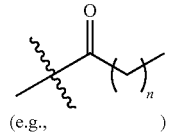

(e.g., )

is a myristoyl group.

In an aspect, the present disclosure also provides a pharmaceutical composition comprising a pharmaceutically acceptable carrier, a peptide of the present disclosure, optionally, a Magi-1 targeting shRNA or Magi-1 targeting siRNA and, optionally, one or more analgesic agents (e.g., nonsteroidal anti-inflammatory drugs (NSAIDS)) and/or one or more anesthetic agent. Non-limiting examples of analgesic agents or anesthetic agents include bupivacaine, etidocaine, levobupivacaine, lidocaine, mepivacaine, prilocaine, ropivacaine, procaine, chloroprocaine, meloxicam, ketorolac, diclofenac, ketoprofen, piroxicam, metamizole, or a combination thereof. Additional examples of analgesics include acetaminophen, aspirin, ibuprofen, naproxen, and the like, and salts thereof. Using techniques and carriers known to those of skill in the art (e.g., *Remington: The Science and Practice of Pharmacy* (2005) 21st Edition, Philadelphia, Pa. Lippincott Williams & Wilkins), the compositions can be formulated as intramuscular, intradermal, intrathecal or nerve injections, topical creams or transdermal patches.

In an aspect, peptide of the present disclosure or composition thereof is used to alter (e.g., increase or decrease) a subject's pain sensitivity (e.g., a subject in need of treatment for pain and pain sensitivity). In an example, a subject's pain is decreased (e.g., ameliorated) when the subject's pain sensitivity is decreased. In another example, a subject's pain sensitivity is increased. In an example, a peptide of the present disclosure, a composition thereof, Magi-1 targeting shRNA, or Magi-1 targeting siRNA are used to manage pain (e.g., pain control).

In an aspect, the present disclosure provides a method of inducing local analgesia in a subject comprising administering composition comprising a peptide having the sequence of any one of SEQ ID NOs. 1-7 or 15-21, Magi-1 targeting shRNA, or Magi-1 targeting siRNA to the subject in analgesic effective amount (e.g., a therapeutically effective amount).

The present disclosure further provides a method of increasing pain sensitivity of a subject comprising administering a composition comprising a peptide having the sequence of any one of SEQ ID NOs. 8-14 or 21-35 to the subject at an amount effective to increase pain sensitivity.

In an aspect, the present disclosure further provides peptides of SEQ ID NOs:36-70 for use as research tools. As such, they can be administered to research subjects, such as mice and rats. The peptides are also useful for in vitro testing.

DESCRIPTION OF THE DRAWINGS

For a fuller understanding of the nature and objects of the disclosure, reference should be made to the following detailed description taken in conjunction with the accompanying figures.

*p<0.05 vs control. Values are expressed as mean+/−SEM. (D) Formalin induced second-phase inflammatory pain as measured by three nocifensive behaviors (paw licking (left graph), lifting (middle graph) and whole body flinches (right graph)) in each interval of 5 mins, is reduced in mice injected with Magi-1 targeting shRNA after 15 days as compared to controls. Behavior from nine different animals (n=9) per experimental condition was analyzed and values are expressed as mean+/−SEM. (ANOVA, licking: $F_{(1,16)}$=7.545, p=0.0143, Lifting: $F_{(1,16)}$=11.67, p=0.0035, flinching: $F_{(1,16)}$=5.007, p=0.0398, *p<0.05, p<0.01 vs respective controls). In each series, the left bar is "scrambled shRNA" and the right bar is "Magi-1 shRNA." (E) Representative Magi-1 immunolabeling in DRG sections obtained from one mouse injected with Magi-1 targeting shRNA (left bottom) compared to one mouse injected with non-targeting scrambled shRNA (left top). Magi-1 immunoreactivity was significantly reduced in ipsilateral paw from mice injected with Magi-1 shRNA as compared to contralateral paw (right). No significant change in immunoreactivity was observed in mice injected with non-targeting scrambled shRNA. DRGs from three different animals were analyzed and values expressed as mean+/−SEM (ANOVA, $F_{(3,20)}$=9.872, p=0.0003, p<0.01 vs. respective controls). (F) Western blot analysis confirmed Magi-1 knockdown in DRGs 15 days after in vivo transfection of Magi-1 targeting shRNA (left). Quantification of Western blot is shown on the right. Intact DRGs from three different animals were analyzed and values expressed as mean+/−SEM. (ANOVA, $F_{(3,8)}$=5.161 *p=0.0282, *p<0.05 vs respective controls.

Figure 8:
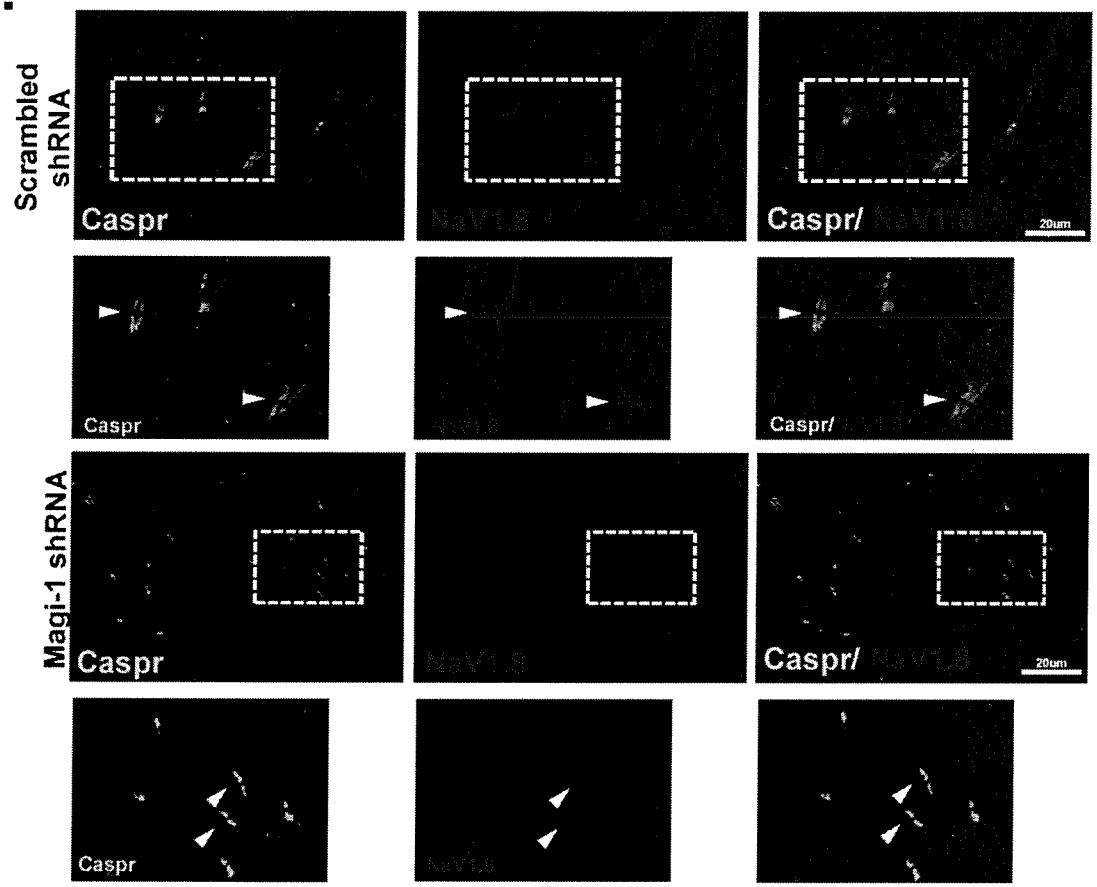
Figure 8:
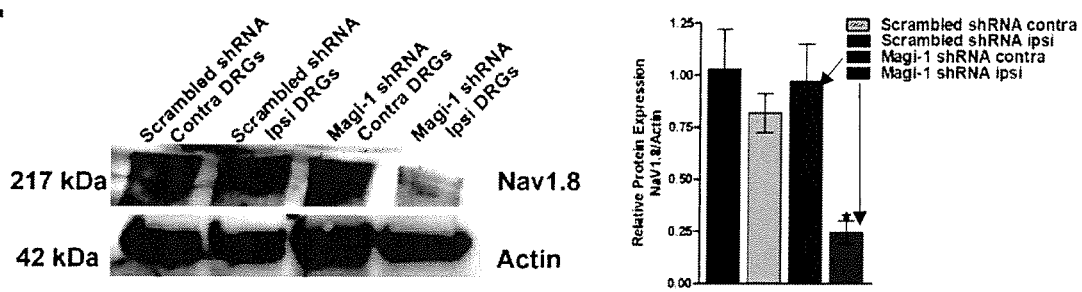
Figure 8:
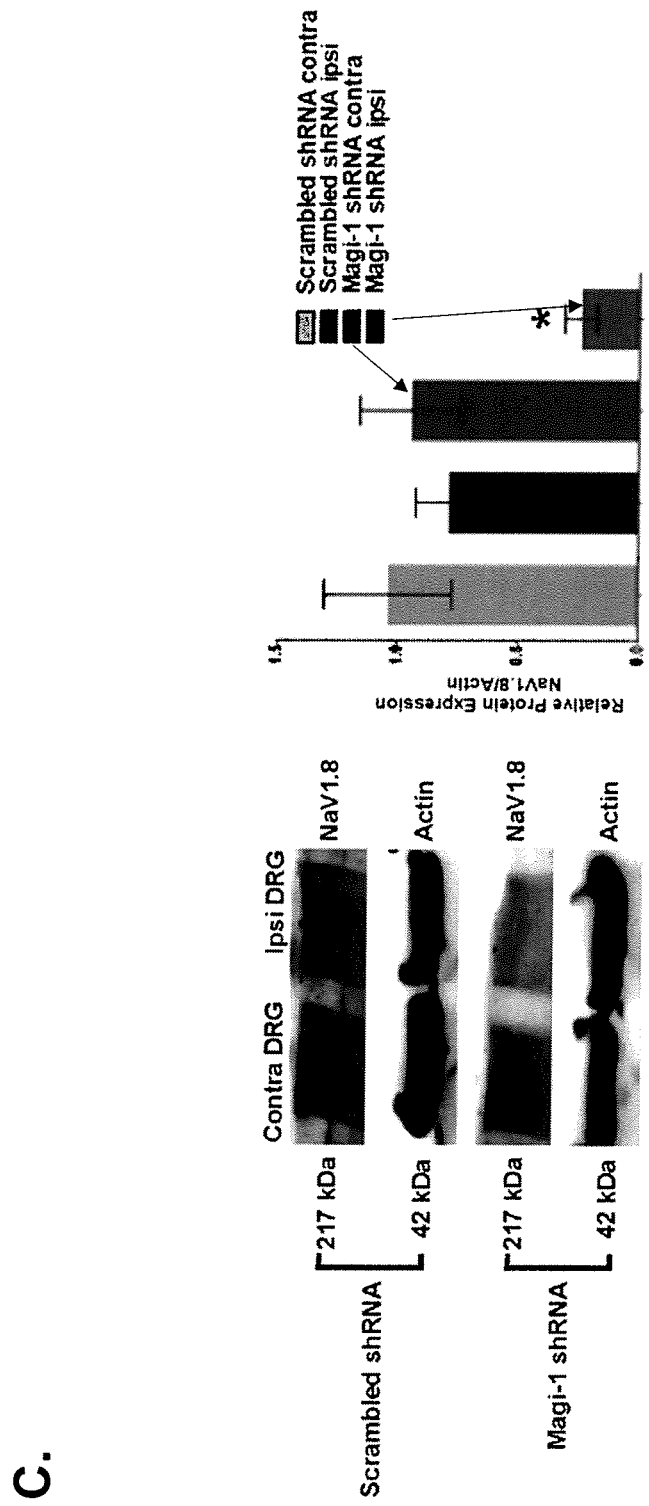

FIG. 8 shows Na$_V$1.8 expression decreases after Magi-1 knockdown in vivo. (A) Representative immunolabeling of sciatic nerve depicting Na$_V$1.8 expression in paw injected with non-targeting shRNA after 15 days (top), expression of Na$_V$1.8 at Nodes of Ranvier was detected using the paranodal marker Caspr. Boxed area is shown below as a high magnification image of Na$_V$1.8 and Caspr immunoreactivity. Bottom, Na$_V$1.8 immunoreactivity was absent in sciatic nerve and at nodes in paw injected with Magi-1 targeting shRNA after 15 days. (B) Representative immunoblots of Na$_V$1.8 expression from ipsilateral and contralateral DRG lysates of mice injected in the sciatic nerve with non-targeting Magi-1 shRNA (scrambled) or Magi-1 targeting shRNA. Representative blot shown for each condition is taken from the same mice. Quantification of Na$_V$1.8 expression is shown of the right. Lumbar DRGs from three different animals were analyzed and values expressed as +/−SEM. *P<0.05 vs representative controls. (C) Western blot analysis showing decreased Na$_V$1.8 expression after Magi-1 knockdown in vivo (left). Quantification of western blot is shown on the right (*p<0.05; One-way ANOVA, and n=3).

Figure 9:
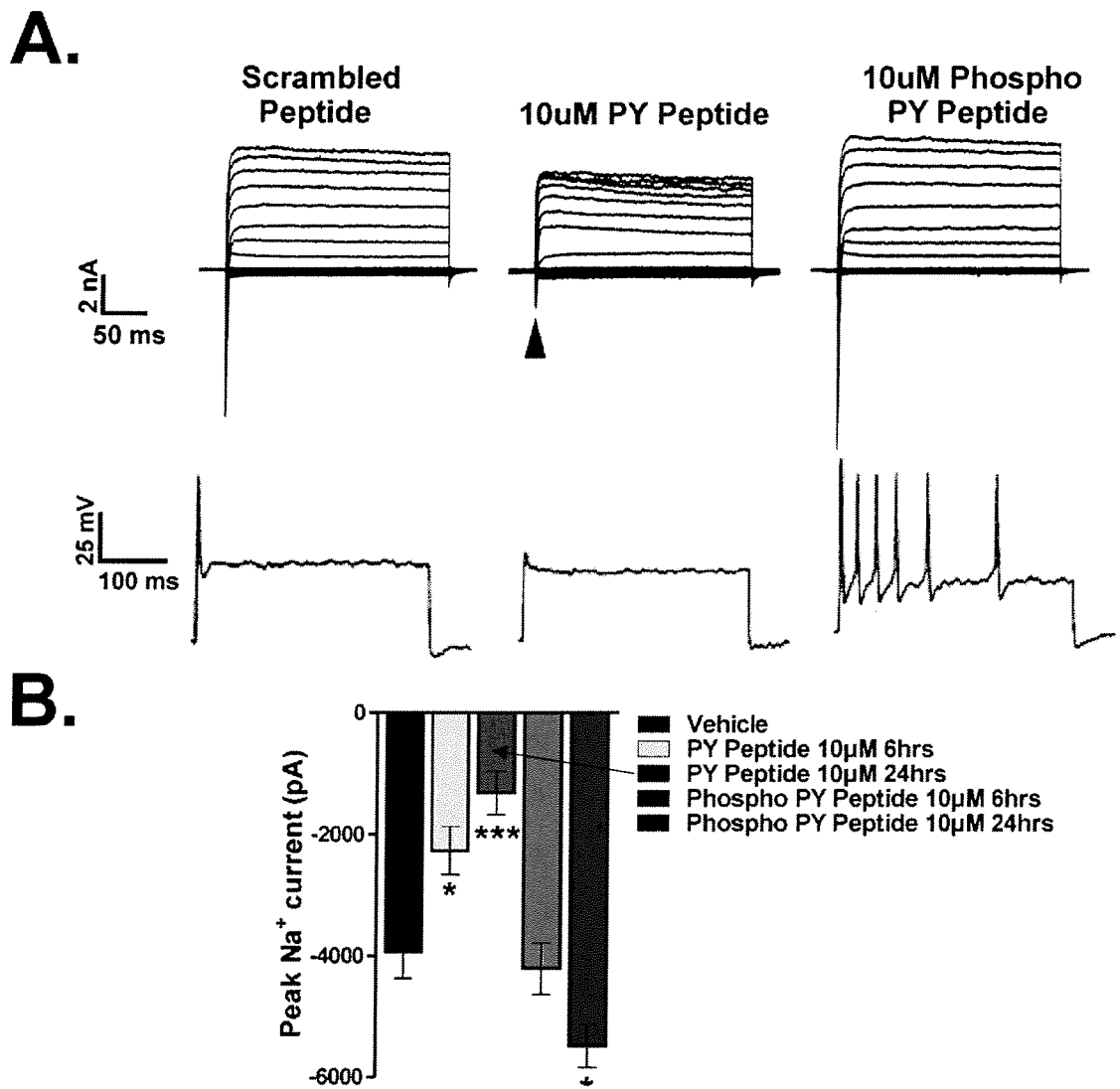
Figure 9:
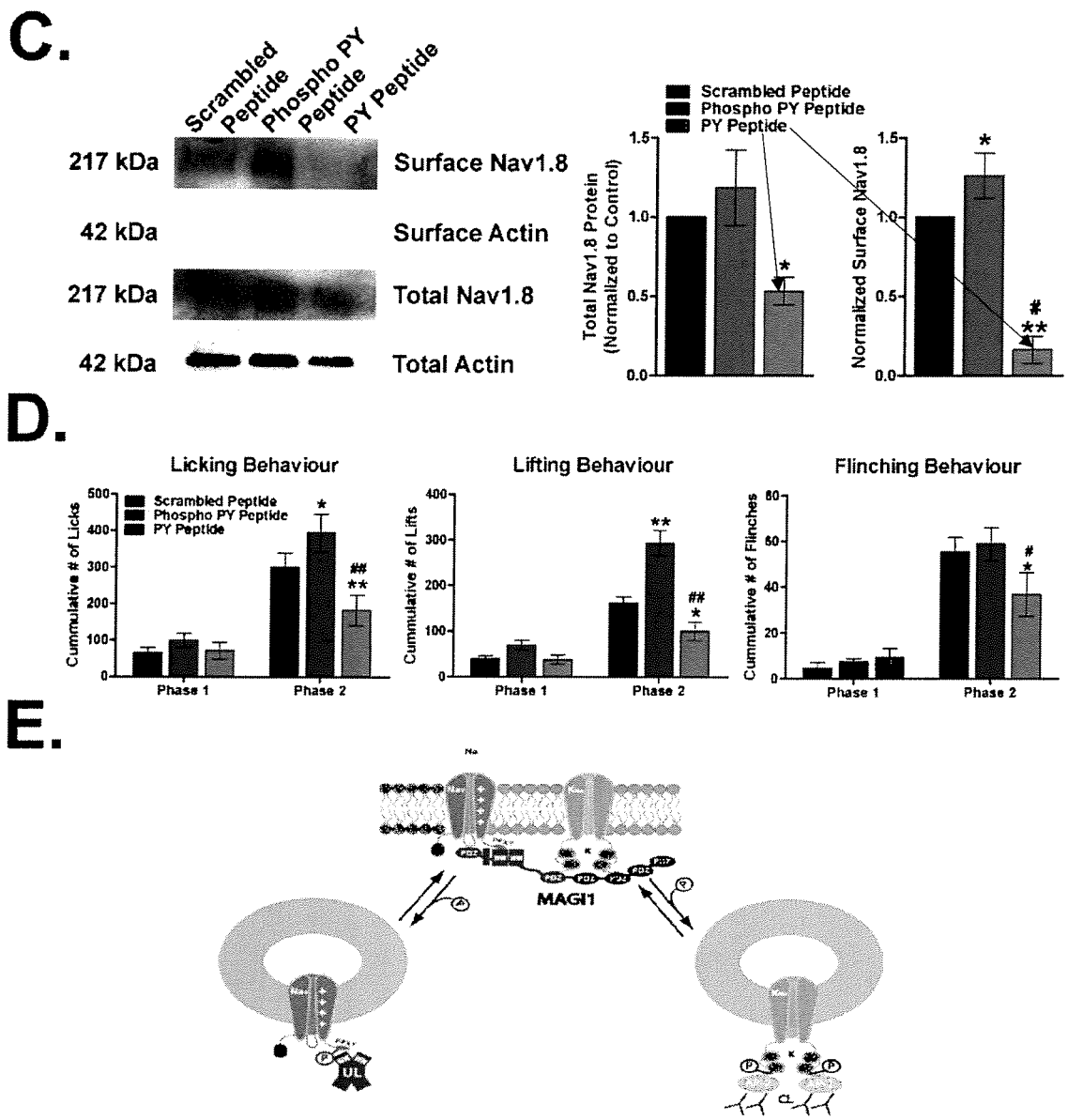

FIG. 9 shows cell penetrating WW motif peptidomimetics alter neuronal excitability and affect pain behavior. (A) Representative voltage-clamp recordings depicting decreased $I_{Na}$ (arrow) in cultured DRG neurons after 24 hr pre-treatment with peptide mimetic designated 'PY peptide' whereas the phospho-PY peptide increased $I_{Na}$ (top). Bottom, representative AP traces from cultured DRG neurons pretreated with PY peptide or phospho-PY peptide for 24 hrs during suprathreshold stimulation (400 pA) for 1000 ms (bottom). (B) Peak $I_{Na}$ (at voltage step −20 mV) with different peptide treatments in DRG neurons. Neurons were treated for 6 hrs or 24 hrs with PY peptide or phospho-PY peptide. 10-12 DRG neurons/experimental condition were analyzed and values are expressed as mean+/−SEM. ANOVA, $F_{(4,35)}$=19.11, P<0.0001, *p<0.05, ***p<0.001 vs respective controls). (C) $Na_V1.8$ protein expression was altered after peptidomimetic treatment. Representative Western blot of total and surface $Na_V1.8$ membrane expression after DRG neurons were treated with PY peptide, phospho-PY peptide or a scrambled (left) for 24 hrs. Quantification of Western blots shown to the right. Treatment with the PY peptide produced a significant reduction of both total and surface $Na_V1.8$ expression when compared to scrambled peptide. The phospho-PY peptide increased surface expression of $Na_V1.8$ when compared to scrambled peptide. Data from three independent cultures were analyzed and values expressed as mean+/−SEM.*$p<0.05$, **$p<0.01$ vs. control; #$p<0.01$ vs phospho-PY peptide. (D) Phase II formalin inflammatory pain was measured by nocifensive behaviors (paw licking (left), lifting (middle) and whole body flinches (right)) in each interval of 5 min, is reduced by intraplantar pre-treatment (24 hrs) with 100 µM (20 µl), of PY peptide whereas phospho-PY peptide increased nocifensive behavioral responses compared to scrambled peptide control. Peptides were administered 24 hr before the formalin injection (5%, µl). Behavior from six different animals per experimental condition were analyzed and values are expressed as mean+/−SEM. *$p<0.05$, **$p<0.01$ vs controls. #$p<0.05$, ##$p<0.01$ vs phospho-PY peptide. (E) Magi-1 constitutes the sodium signalosome in DRG neurons. Slack $K_{Na}$ channels were previously shown to internalize by adaptin2-dependent clathrin-mediated endocytosis. AP-2-adaptin complex, CL-clathrin, UL-ubiquitin ligase.

Figure 10:
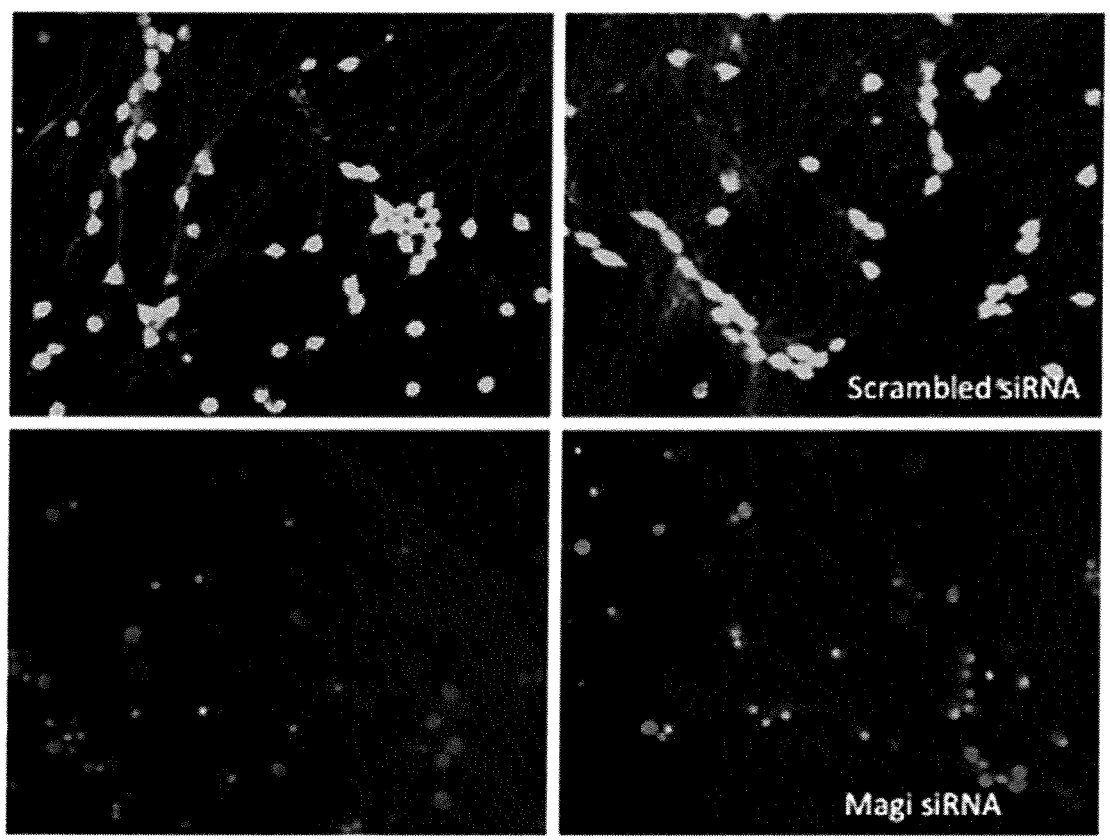

FIG. 10 shows additional images of scrambled siRNA treated and Magi-1 siRNA treated neurons. Transfection of scrambled siRNA (upper panels) and Magi-1 siRNA (lower panels) of cultured DRG neurons was generally non-cytotoxic and equivalent numbers of neurons were used for the quantitative analyses of immunofluorescence.

Figure 11:
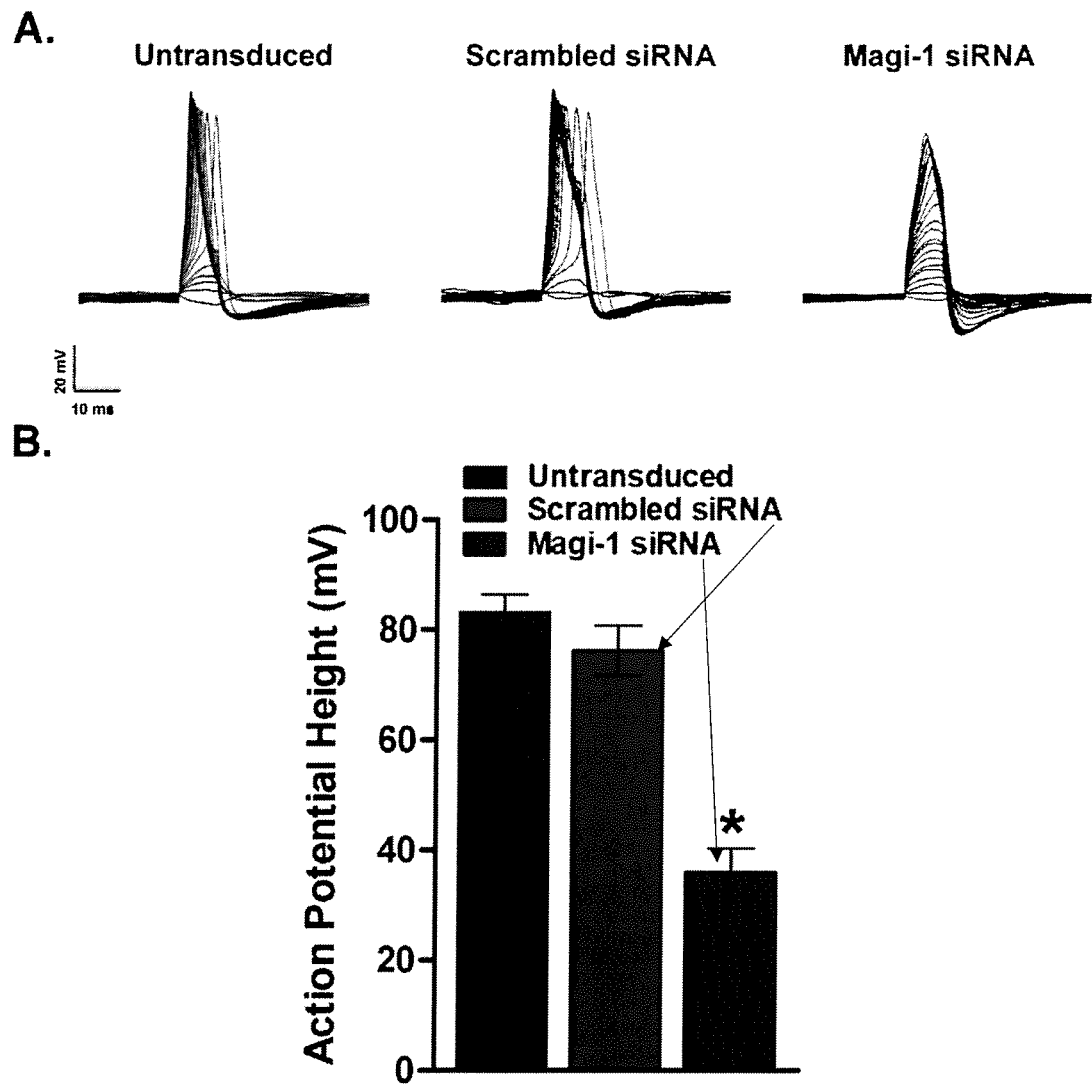

FIG. 11 shows Magi-1 Knockdown DRG neurons alters AP properties. (A) Representative traces of increasing current injection used to elicit APs. Magi-1 knockdown caused graded potentials rather than typical all-or-none APs. (B) Measurements of AP height in untreated (n=10), scrambled siRNA: (n=12), and Magi-1 siRNA n=18 neurons. Corresponding rheobase measurements: untreated neurons 211+/−27 pA; scrambled siRNA 142+/−24 pA; Magi-1 siRNA 583+/−76 pA $p<0.05$ vs. siRNA control (ANOVA). Input resistances for untreated and scrambled siRNA treated neurons ranged from 200-300 MΩ and 400-500 MΩ for Magi-1 siRNA treated neurons. AP amplitudes were analyzed for these experimental conditions and values are expressed as mean+/−SEM. (ANOVA, $F_{(2,32)}=39.64$, $p<0.001$, *$p<0.0001$ vs. respective controls.

Figure 12:
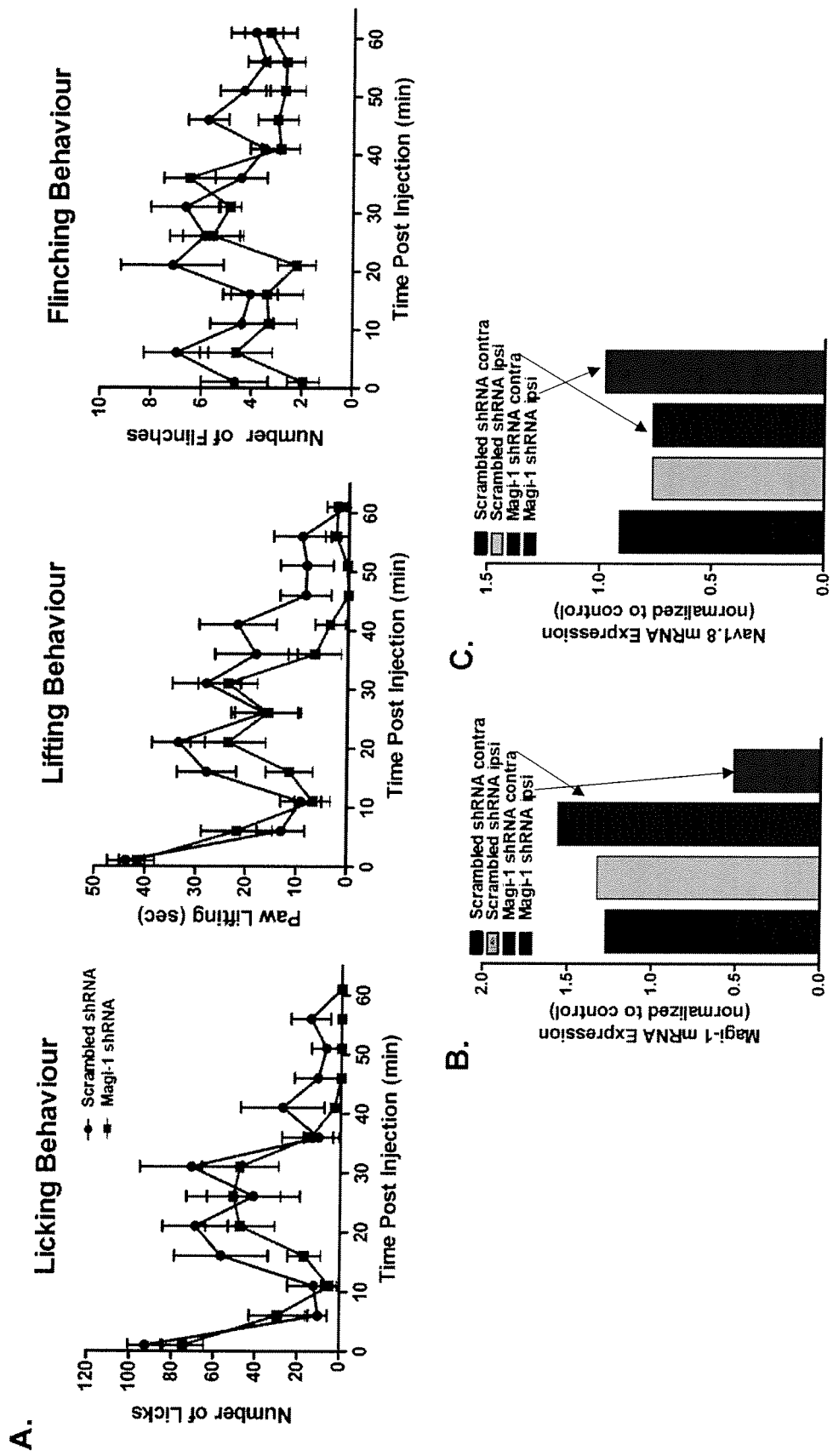

FIG. 12 shows Magi-1 in vivo knockdown. (A) Time course of inflammatory pain responses after 5% formalin injection taken from the entire cohort (6 males and 3 females). No animals were excluded. Nocifensive behaviors were measured over a period of 60 minutes in mice injected with Magi-1 shRNA or control shRNA. Injection with formalin produced the typical biphasic response of this model for inflammatory pain. Mice injected with shRNA showed significant reduction in phase II (10-60 minutes) inflammatory pain. (B) Non-quantitative qRT-PCR confirmed reductions in Magi-1 RNA in ipsilateral paw injected with Magi-1 shRNA as compared to contralateral paw from the same mice and animals injected with control shRNA. (C) No change in $Na_V1.8$ transcripts in ipsilateral paw injected with Magi-1 shRNA was observed compared to contralateral paw from the same mouse and an animal injected with control shRNA.

Figures 13, 14:
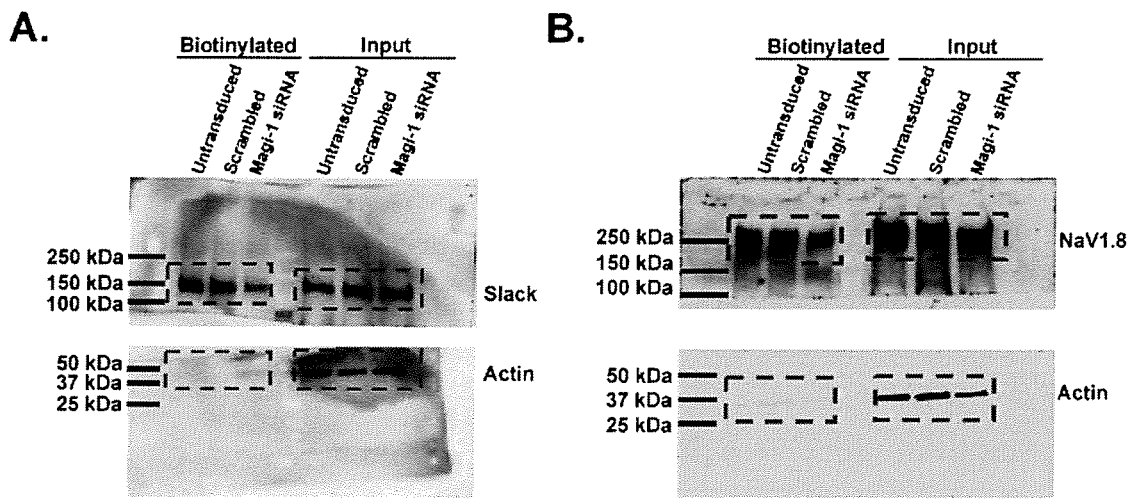

FIG. 13 shows evolutionarily conserved PY motif in $Na_V$ channels. WW binding motifs in $Na_V$ channels. Sequence alignment of rat $Na_V$ channels that have the consensus WW binding motifs. PPSY (SEQ ID NO:73) is the WW motif. Phosphoproteomic data from PhosphoSitePlus® on $Na_V1.8$ channel indicates that threonine1924 in rat, which is threonine1926 in mice (third residue from the C-terminus) is phosphorylated.

FIG. 14 shows representative whole blots for membrane biotinylation experiments. DRG Neuronal biotinylation; (A) FIG. 3E, (B) FIG. 4D, and (C) FIG. 9C, and CHO cell biotinylation (D) FIG. 1E.

Figure 5:
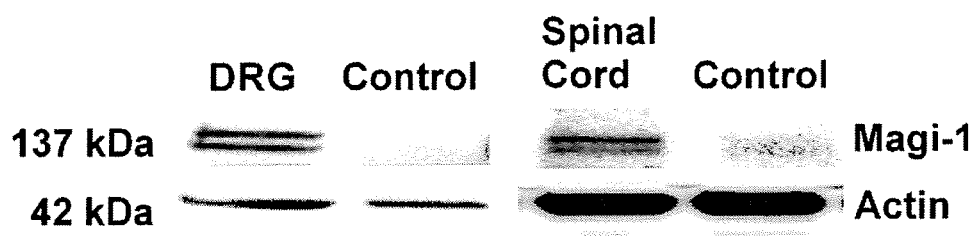
FIG. 5 shows Magi-1 is expressed in DRG neurons, spinal cord, sciatic nerve and at Nodes of Ranvier. (A) Representative immunoblots depicting Magi-1 expression from intact DRG (left) and spinal cord (right) (B) Immunolabeling images showing Magi-1 expression in cultured DRG neurons (panel 1), DRG sections (panels 2 and 3) and the spinal cord (panels 4 and 5) using a previously validated monoclonal antibody. Panel 4 demonstrates control immunolabeling, stained with secondary antibody only. Dapi labels all nuclei of cells. Scale bars, 50 µm. (C) Double immunolabeling depicting Magi-1 and the paranodal marker Caspr in sciatic nerve sections (top). Scale bar, 50 µm. Arrows indicate Magi-1 labeling at nodes of Ranvier. Bottom, insets represents high magnification images of Magi-1 immunoreactivity at nodes. Scale bar, 10 µm. (D) Frequency distribution of Magi-1 in intact DRG neurons of varying cell body size. A total of 735 neurons from four mice were analyzed (in each series: left is all neurons and right is Magi-1 positive neurons).
Figure 5:
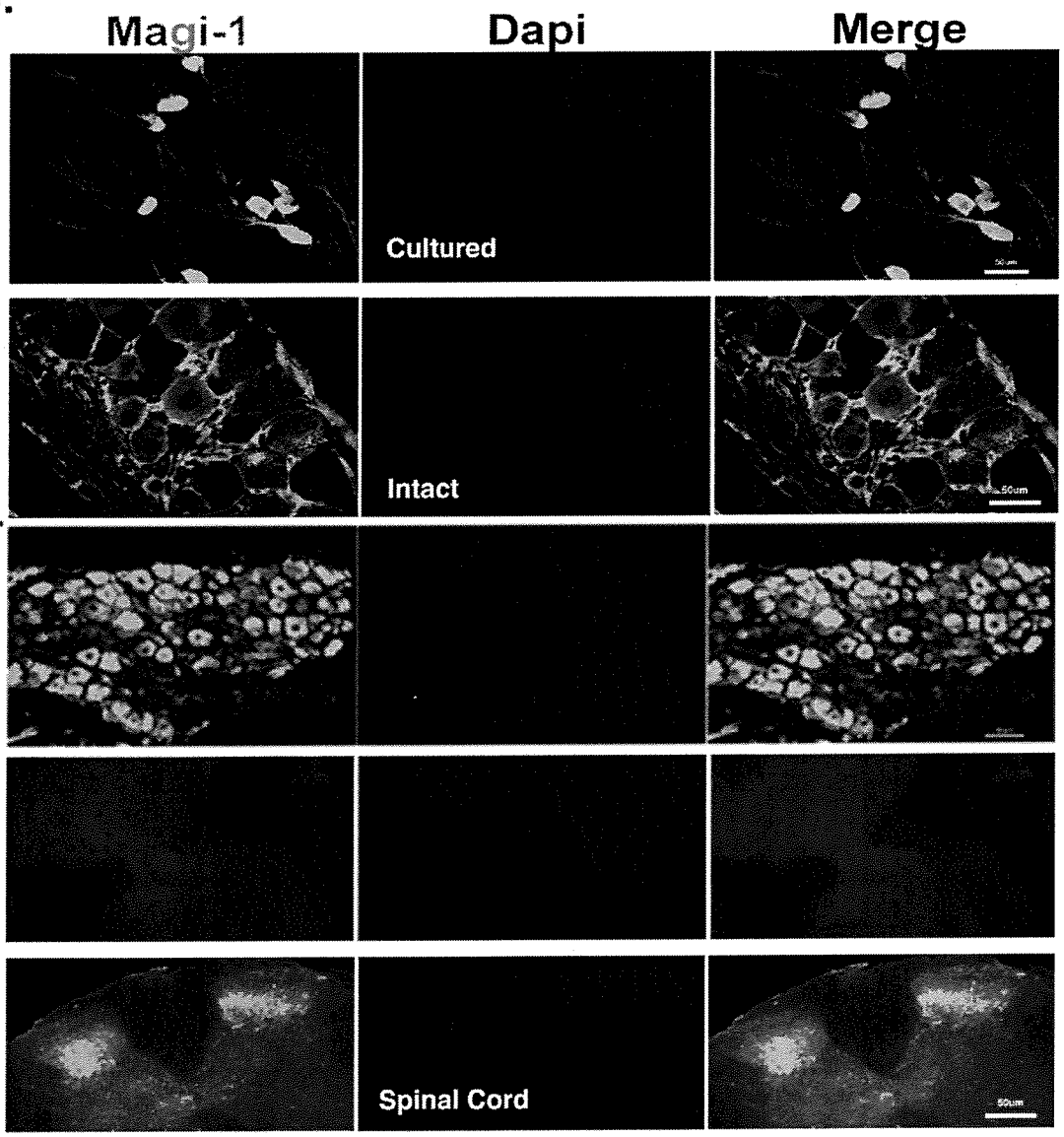
Figure 5:
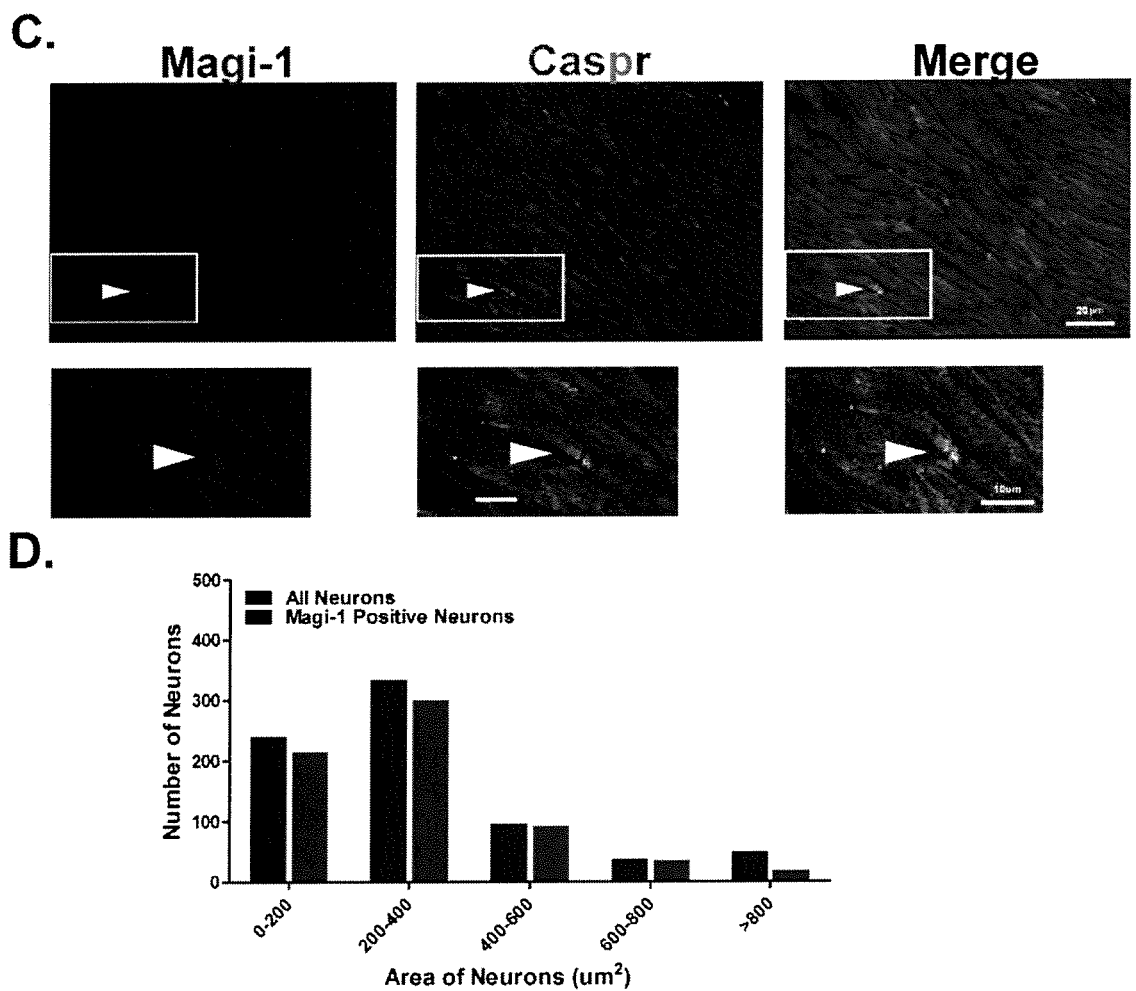
Figure 6:
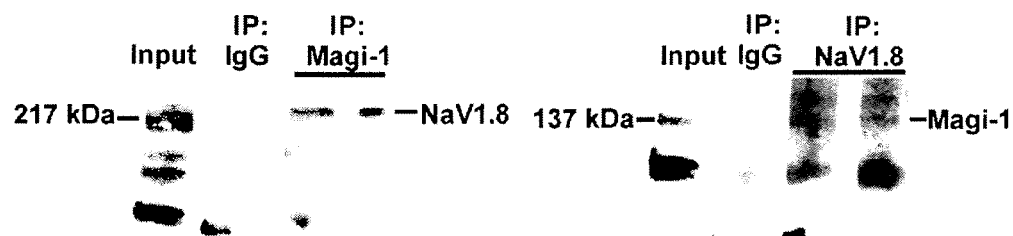
FIG. 6 shows Magi-1 complexes Na$_V$1.8 channels with Slack K$_{Na}$ channels in DRG neurons. (A) Representative whole immunoblots from co-immunoprecipitation (Co-IP) assays demonstrating binding between Magi-1 and Na$_V$1.8 using intact adult DRG tissue. IP product samples were run in duplicate. The polyclonal Magi-1 antibody also recognized a 50 kDa band during blotting thought to be a degradation product (as per manufacturer's description) (B) Double immunolabeling experiments demonstrate similar localization between Magi-1 and Na$_V$1.8 in cultured DRG neurons (panel 1), DRG sections (panel 2), and the spinal cord (Panel 3). Scale bar, 50 µm. (C) Representative immunoblots of Co-IP between Slack and Na$_V$1.8 from intact adult DRG neurons. (D) CoIP showing the interaction between Magi-1 and Na$_V$1.8 in mouse DRGs. DRG lysate was immunoprecipitated with either anti-Magi-1 antibody (left) or anti-Na$_V$1.8 antibody (right), and immunoblotted with anti-Na$_V$1.8 or anti Magi-1 antibody as indicated. This experiment was repeated at least three times. (E) Double immunolabeling showing co-localization of Slack and Na$_V$1.8 in intact DRG neurons. The scale bar represents 20 µm.
Figure 6:
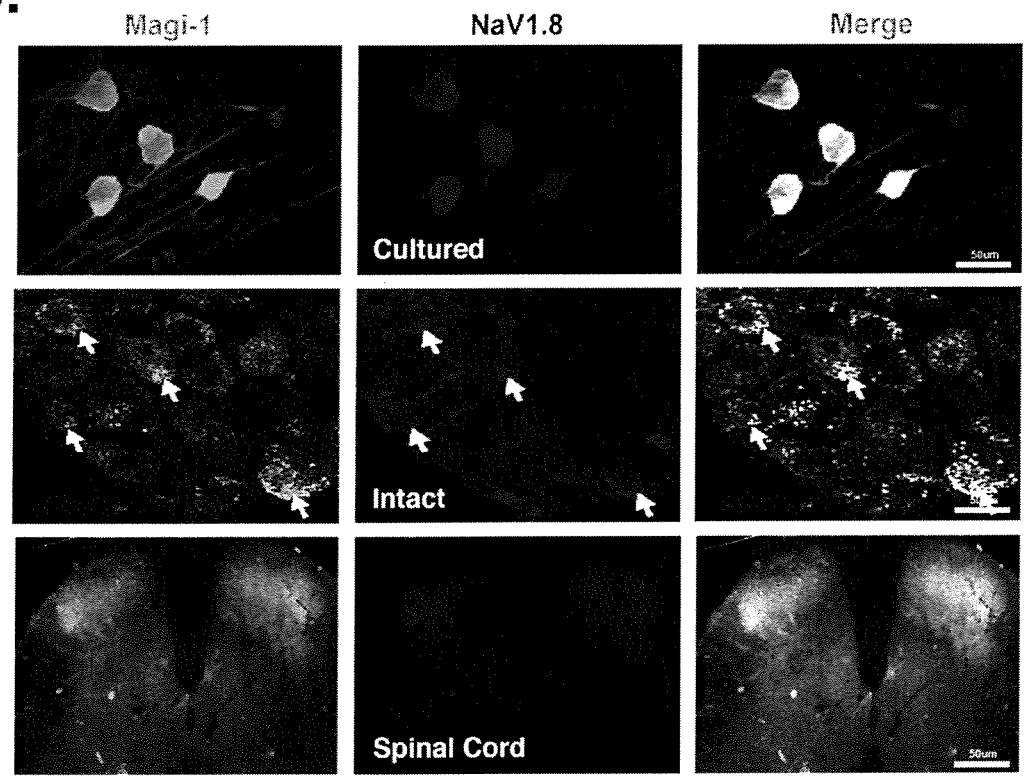
Figure 6:
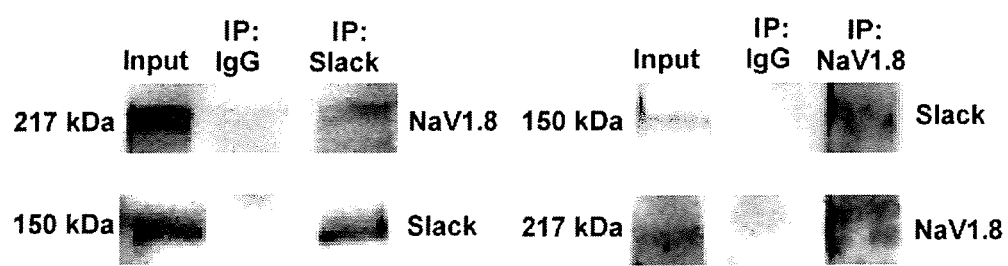
Figure 6:
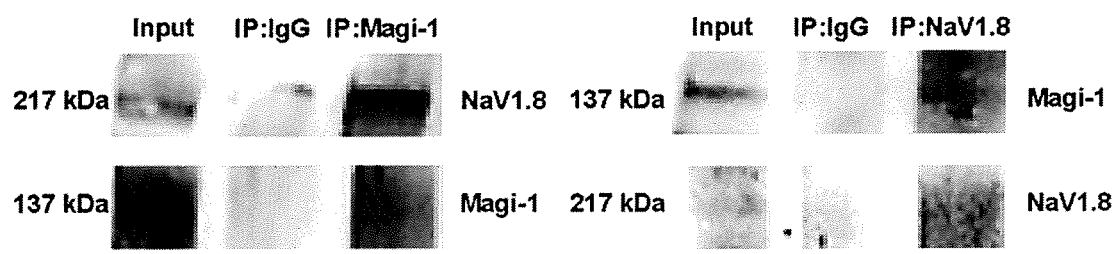
Figure 6:
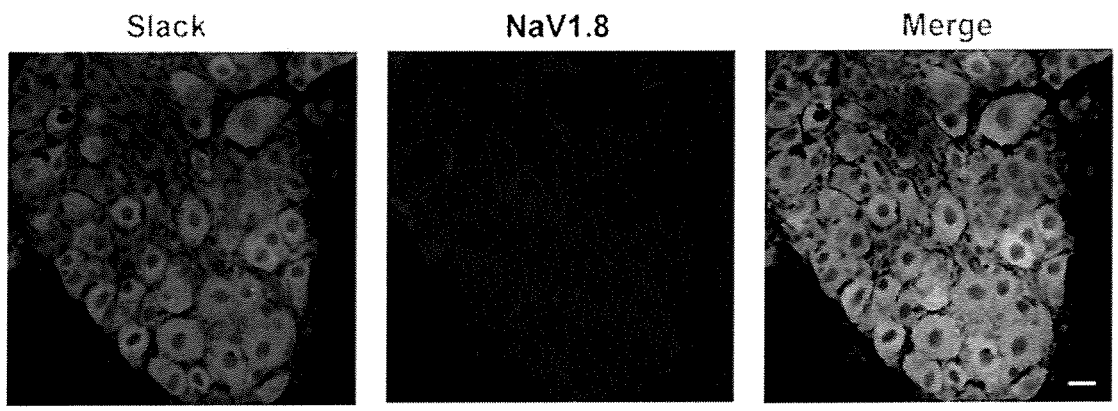
Figure 15:
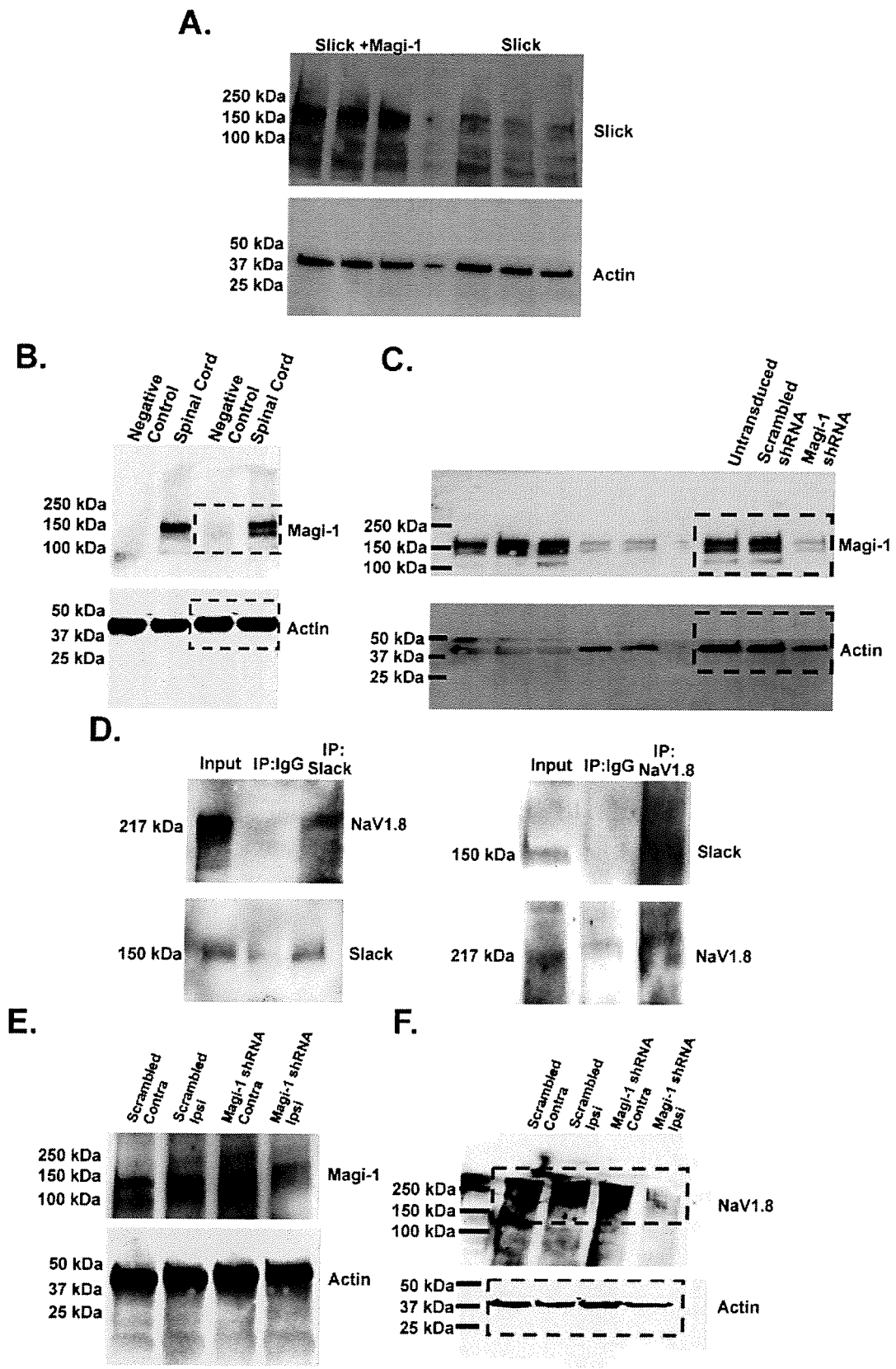

FIG. 15 shows representative full blots for Western blots and co-immunoprecipitation assays. A. FIG. 2C, B. FIG. 5A, C. FIG. 2B, D. FIG. 6C, E. FIG. 6F, F. FIG. 8B.

Figure 16:
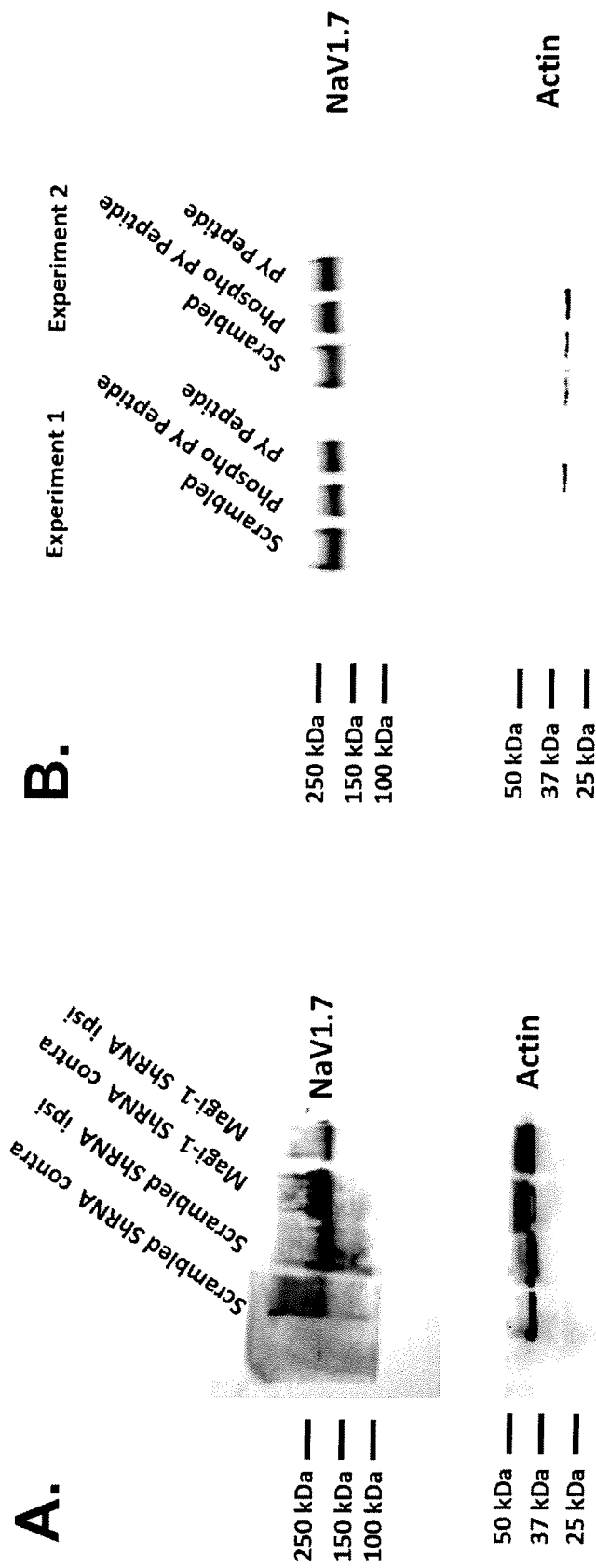

FIG. 16 shows $Na_V1.7$ protein expression was diminished during in vivo Magi-1 knockdown but surface expression was unaltered after treatment with WW motif peptidomimetics. A. Immunoblot of $Na_V1.7$ expression from ipsilateral and contralateral DRG lysates of mice injected in the sciatic nerve with non-targeting Magi-1 shRNA (scrambled) or Magi-1 targeting shRNA. B. Western blots from two experiments of surface (biotinylated) $Na_V1.7$ membrane expression after cultured DRG neurons were treated with PY peptide, phospho-PY peptide or a scrambled (left) for 24 hrs.

DETAILED DESCRIPTION OF THE DISCLOSURE

Although claimed subject matter will be described in terms of certain embodiments/examples, other embodiments/examples, including embodiments/examples that do not provide all of the benefits and features set forth herein, are also within the scope of this disclosure. Various structural, logical, and process step changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

Throughout this application, the singular form encompasses the plural and vice versa. The references cited in this application are hereby incorporated by reference. All sections of this application, including any supplementary sections or figures, are fully a part of this application.

The term "treatment" as used herein refers to reduction in one or more symptoms or features associated with the presence of the particular condition being treated. Treatment does not necessarily mean complete cure or remission, nor does it preclude recurrence or relapses. For example, treatment in the present disclosure means reducing pain (e.g., decreasing pain sensitivity) or increasing pain sensitivity.

The term "therapeutically effective amount" as used herein refers to an amount of an agent sufficient to achieve, in a single or multiple doses, the intended purpose of treatment. Treatment does not have to lead to complete cure, although it may. Treatment can mean alleviation of one or more of the symptoms or markers of the indication. The exact amount desired or required will vary depending on the particular compound or composition used, its mode of administration, patient specifics and the like. Appropriate effective amount can be determined by one of ordinary skill in the art informed by the instant disclosure using only routine experimentation. Treatment can be orientated symptomatically, for example, to suppress symptoms. It can be effected over a short period, over a medium term, or can be a long-term treatment, such as, for example within the context of a maintenance therapy. Treatment can be continuous or intermittent.

Unless otherwise indicated, nucleic acids are written left to right in 5' to 3' orientation; amino acid sequences are written left to right in amino to carboxyl orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

$Na_V1.8$ channels determine the depolarizing phase of the action potential (AP) in nociceptive neurons. $Na_V1.8$ channel plasma membrane localization, retention and stability occurs through a direct interaction with the PDZ- and WW-domain containing scaffold protein called Magi-1. Additionally, dorsal root ganglion (DRG)-specific knockdown of Magi-1 attenuated thermal nociception and inflammatory pain and deficits in $Na_V1.8$ protein expression. The present disclosure describes a competing, cell-penetrating, peptide mimetic derived from $Na_V1.8$ WW binding motif. A peptide of the present disclosure triggered a decrease in sodium current, an almost complete loss of $Na_V1.8$ expression and stunted AP firing in DRG neurons. A peptide of the present disclosure can also trigger an increase in sodium current. A single intraplantar peptide mimetic injection caused a reduction in nocifensive behaviors. It is further described that Magi-1 binds to Slack $K_{Na}$ channels through a PDZ interaction, resulting in macro-complexing with $Na_V1.8$ channels. These data indicate that Magi-1 is an essential scaffold for ion transport in DRG neurons and a central player in pain signaling.

In an aspect, the present disclosure provides a peptide comprising or consisting of the following sequence:

$X^1X^2X^3X^4X^5X^6PX^7YX^8X^9VX^{10}X^{11}X^{12}$ (SEQ ID NO:75), wherein $X^1$ is S, P, or A; $X^2$ is T, S, or A; $X^3$ is A or T; $X^4$ is A, T, I, or S; $X^5$ is C, S, or F; $X^6$ is P or L; $X^7$ is any amino acid residue, $X^8$ is E, D, or Y; $X^9$ is S or R; $X^{10}$ is T, A, E, or D, and T is optionally phosphorylated; $X^{11}$ is K or R; and $X^{12}$ is P, A, or G, and wherein $X^1$, $X^2$, $X^3$, $X^9$, $X^{10}$, $X^{11}$, or a combination thereof is acylated 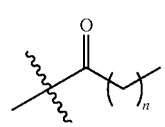 (e.g., and n is 4-18, (e.g., 4, 5, 6, 7, 8, 9, 10, 11, 12, 13, 14, 15, 16, 17, or 18). In a further embodiment, the acyl group 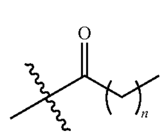 (e.g., )

is a myristoyl group.

In an embodiment, a peptide of the present disclosure is acylated at the N-terminus. In another embodiment, a peptide of the present disclosure is acylated at a nucleophilic atom of an amino acid residue (e.g., the sidechain oxygen atom of a serine or threonine, the sidechain nitrogen of a lysine, and the like).

In an embodiment, $X^1$ is S or P and is acylated (e.g., myristoylated) at the amine N-terminal amine of $X^1$. The sequence further comprises $-PPX^7Y-$ at the $-X^6PX^7Y-$portion of the peptide sequence, where X is any amino acid residue. In a further example, $X^7$ is S.

The present disclosure describes a peptide sequentially comprising:

a) an acylated amino acid residue 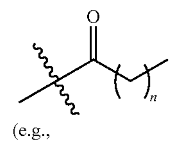 (e.g., and n is 4-18, (e.g., 4, 5, 6, 7, 8, 9, 10, 11, 12, 13, 14, 15, 16, 17, or 18), such as, for example, a myristoylated amino acid residue);

b) at least one intervening amino acid residue;

c) a first amino acid sequence; and d) a terminal amino acid sequence.

In one embodiment, the myristoylated amino acid residue is S, P, or A. In an embodiment for human use, the myristoylated amino acid residue is S or P.

In another embodiment, the at least one intervening amino acid residue comprises T, S, or A, wherein said T, S, or A immediately succeeds (i.e., follows, going from N- to C-terminus) the myristoylated amino acid residue. In a further embodiment, said T, S or A is immediately succeeded by A or T. In yet another embodiment, said A or T is immediately succeeded by A, T, S or I. In an embodiment for human use, said A or T is immediately succeeded by A, T or S. In an additional embodiment, said A, T, S or I is immediately succeeded by C, S or F. In a further embodiment for human use, said A, T or S is immediately succeeded by C, S or F.

In one embodiment, said first amino acid sequence comprises PXY, wherein X is any amino acid residue.

In another embodiment, said first amino acid sequence comprises UPXY (SEQ ID NO:71), wherein U is P or L and X is any amino acid residue. In a further embodiment, X is S.

In yet another embodiment, the terminal amino acid sequence comprises A, D, E, or an amino acid residue capable of being phosphorylated and dephosphorylated. In an embodiment, the amino acid residue capable of being phosphorylated and dephosphorylated is T. In a further embodiment, the amino acid residue capable of being phosphorylated and dephosphorylated is phosphorylated. In still another embodiment, the amino acid residue capable of being phosphorylated and dephosphorylated is not phosphorylated.

In one embodiment, the terminal amino acid sequence comprises D or E, wherein said D or E immediately succeeds said first amino acid sequence. In an embodiment, said D or E is immediately succeeded by R or S. In another embodiment, said R or S is immediately succeeded by V. In a further embodiment, said V is immediately succeeded by said A, D, E, or amino acid residue capable of being phosphorylated and dephosphorylated. In an embodiment, said A, D, E, or amino acid residue capable of being phosphorylated and dephosphorylate is immediately succeeded by K or R. In another embodiment, said K or R is immediately succeeded by P, A or G.

In a preferred embodiment, the peptide has any one of the sequences in Tables 1 or 2.

TABLE 1

Human Peptides

| SEQ ID | Sodium Channel | Sequence |
|---|---|---|
| 1 | SCN1A | (myristoyl)-STAACPPSYDRVTKP |
| 2 | SCN2A | (myristoyl)-PSTTSPPSYDSVTKP |
| 3 | SCN3A | (myristoyl)-SSTTSPPSYDSVTKP |
| 4 | SCN5A | (myristoyl)-SSTSFPPSYDSVTRA |
| 5 | SCN8A | (myristoyl)-PSTASLPSYDSVTKP |
| 6 | SCN9A | (myristoyl)-SSTTSPPSYDSVTKP |
| 7 | SCN10A | (myristoyl)-SATSFPPSYESVTRG |
| 8 | SCN1A | (myristoyl)-STAACPPSYDRVT^KP |
| 9 | SCN2A | (myristoyl)-PSTTSPPSYDSVT^KP |
| 10 | SCN3A | (myristoyl)-SSTTSPPSYDSVT^KP |
| 11 | SCN5A | (myristoyl)-SSTSFPPSYDSVT^RA |
| 12 | SCN8A | (myristoyl)-PSTASLPSYDSVT^KP |
| 13 | SCN9A | (myristoyl)-SSTTSPPSYDSVT^KP |
| 14 | SCN10A | (myristoyl)-SATSFPPSYESVT^RG |
| 15 | SCN1A | (myristoyl)-STAACPPSYDRVAKP |
| 16 | SCN2A | (myristoyl)-PSTTSPPSYDSVAKP |
| 17 | SCN3A | (myristoyl)-SSTTSPPSYDSVAKP |
| 18 | SCN5A | (myristoyl)-SSTSFPPSYDSVARA |
| 19 | SCN8A | (myristoyl)-PSTASLPSYDSVAKP |
| 20 | SCN9A | (myristoyl)-SSTTSPPSYDSVAKP |
| 21 | SCN10A | (myristoyl)-SATSFPPSYESVARG |
| 22 | SCN1A | (myristoyl)-STAACPPSYDRVEKP |
| 23 | SCN2A | (myristoyl)-PSTTSPPSYDSVEKP |
| 24 | SCN3A | (myristoyl)-SSTTSPPSYDSVEKP |
| 25 | SCN5A | (myristoyl)-SSTSFPPSYDSVERA |
| 26 | SCN8A | (myristoyl)-PSTASLPSYDSVEKP |
| 27 | SCN9A | (myristoyl)-SSTTSPPSYDSVEKP |
| 28 | SCN10A | (myristoyl)-SATSFPPSYESVERG |
| 29 | SCN1A | (myristoyl)-STAACPPSYDRVDKP |
| 30 | SCN2A | (myristoyl)-PSTTSPPSYDSVDKP |
| 31 | SCN3A | (myristoyl)-SSTTSPPSYDSVDKP |
| 32 | SCN5A | (myristoyl)-SSTSFPPSYDSVDRA |
| 33 | SCN8A | (myristoyl)-PSTASLPSYDSVDKP |

TABLE 1-continued

Human Peptides

| SEQ ID | Sodium Channel | Sequence |
|---|---|---|
| 34 | SCN9A | (myristoyl)-SSTTSPPSYDSVDKP |
| 35 | SCN10A | (myristoyl)-SATSFPPSYESVDRG | where the residue is myristoylated it is indicated by (myristoyl)- and ^ denotes the T immediately preceding the "^" is phosphorylated.

TABLE 2

Rat Peptides

| SEQ ID | Sodium Channel | Sequence |
|---|---|---|
| 36 | Scn1a | (myristoyl)-STAACPPSYDRVTKP |
| 37 | Scn2a | (myristoyl)-PSTTSPPSYDSVTKP |
| 38 | Scn3a | (myristoyl)-SSTTSPPSYDSVTKP |
| 39 | Scn5a | (myristoyl)-SSTSFPPSYDSVTRA |
| 40 | Scn8a | (myristoyl)-SSTASLPSYDSVTKP |
| 41 | Scn9a | (myristoyl)-SSTISPPSYDSVTKP |
| 42 | Scn10a | (myristoyl)-SATSFPPSYDSVTRG |
| 43 | Scn1a | (myristoyl)-STAACPPSYDRVT^KP |
| 44 | Scn2a | (myristoyl)-PSTTSPPSYDSVT^KP |
| 45 | Scn3a | (myristoyl)-SSTTSPPSYDSVT^KP |
| 46 | Scn5a | (myristoyl)-SSTSFPPSYDSVT^RA |
| 47 | Scn8a | (myristoyl)-SSTASLPSYDSVT^KP |
| 48 | Scn9a | (myristoyl)-SSTISPPSYDSVT^KP |
| 49 | Scn10a | (myristoyl)-SATSFPPSYDSVT^RG |
| 50 | Scn1a | (myristoyl)-STAACPPSYDRVAKP |
| 51 | Scn2a | (myristoyl)-PSTTSPPSYDSVAKP |
| 52 | Scn3a | (myristoyl)-SSTTSPPSYDSVAKP |
| 53 | Scn5a | (myristoyl)-SSTSFPPSYDSVARA |
| 54 | Scn8a | (myristoyl)-SSTASLPSYDSVAKP |
| 55 | Scn9a | (myristoyl)-SSTISPPSYDSVAKP |
| 56 | Scn10a | (myristoyl)-SATSFPPSYDSVARG |
| 57 | Scn1a | (myristoyl)-STAACPPSYDRVEKP |
| 58 | Scn2a | (myristoyl)-PSTTSPPSYDSVEKP |
| 59 | Scn3a | (myristoyl)-SSTTSPPSYDSVEKP |
| 60 | Scn5a | (myristoyl)-SSTSFPPSYDSVERA |
| 61 | Scn8a | (myristoyl)-SSTASLPSYDSVEKP |
| 62 | Scn9a | (myristoyl)-SSTISPPSYDSVEKP |
| 63 | Scn10a | (myristoyl)-SATSFPPSYDSVERG |
| 64 | Scn1a | (myristoyl)-STAACPPSYDRVDKP |

TABLE 2-continued

Rat Peptides

| SEQ ID | Sodium Channel | Sequence |
|---|---|---|
| 65 | Scn2a | (myristoyl)-PSTTSPPSYDSVDKP |
| 66 | Scn3a | (myristoyl)-SSTTSPPSYDSVDKP |
| 67 | Scn5a | (myristoyl)-SSTSFPPSYDSVDRA |
| 68 | Scn8a | (myristoyl)-SSTASLPSYDSVDKP |
| 69 | Scn9a | (myristoyl)-SSTISPPSYDSVDKP |
| 70 | Scn10a | (myristoyl)-SATSFPPSYDSVDRG | where the residue is myristoylated it is indicated by (myristoyl)- and ^ denotes the T immediately preceding the "^" is phosphorylated.

Using sequence 1 from Table 1 as an example, the present disclosure provides a peptide wherein the myristoylated amino acid is S, the at least one intervening amino acid residue is TAAC (SEQ ID:72), the first amino acid sequence is PPSY (SEQ ID NO:73) and the terminal amino acid sequence is DRVTKP (SEQ ID NO:74).

The sequences of Table 1 were derived from the WW binding domains in sodium channels SCN1A, SCN2A, SCN3A, SCN5A, SCN8A, SCN9A, SCN10A and further modified (e.g., acylated). The peptides of SEQ ID NOs. 1-14 use threonine as the third last amino acid of the sequence. Threonine is capable of being phosphorylated and dephosphorylated. In the peptides of SEQ ID NOs. 15-21, alanine replaces threonine negating any putative in vivo phosphorylation of peptide that may limit potency. In the peptides of SEQ ID NOs. 22-28, glutamic acid replaces threonine. In the peptides of SEQ ID NOs. 29-35, aspartic acid replaces glutamic acid. The glutamate and the aspartic acid, respectively, mimic a permanently phosphorylated threonine (resistant to endogenous phosphatase action). Neither the glutamate nor the aspartic acid is actually phosphorylated. Without intending to be bound by any particular theory, these peptides may provide longer action due to retained negative charge at this amino acid site resistant to phosphatase action.

In an embodiment, a peptide of the current disclosure increases or decreases inward sodium current of neurons. Sodium current is typically measured at peak. In an example, a peptide of the present disclosure increases or decrease sodium current of neurons in a local/targeted area (e.g., an area of treatment).

In an embodiment, a peptide of the present disclosure is not an anesthetic agent. A peptide of the present disclosure that decreases sodium current does not act as a sodium channel blocker, but rather induces degradation of sodium channels.

In an aspect, the present disclosure also provides a pharmaceutical composition comprising a pharmaceutically acceptable carrier, a peptide of the present disclosure, optionally, a Magi-1 targeting shRNA or Magi-1 targeting siRNA and, optionally, one or more analgesic agents (e.g., nonsteroidal anti-inflammatory drugs (NSAIDS)) and/or one or more anesthetic agent. Non-limiting examples of analgesic agents or anesthetic agents include bupivacaine, etidocaine, levobupivacaine, lidocaine, mepivacaine, prilocaine, ropivacaine, procaine, chloroprocaine, meloxicam, ketorolac, diclofenac, ketoprofen, piroxicam, metamizole, or a combination thereof. Additional examples of analgesics include acetaminophen, aspirin, ibuprofen, naproxen, and the like, and salts thereof. Using techniques and carriers known to those of skill in the art (e.g., Remington: The Science and Practice of Pharmacy (2005) 21st Edition, Philadelphia, PA. Lippincott Williams & Wilkins), the compositions can be formulated as intramuscular, intradermal, intrathecal or nerve injections, topical creams or transdermal patches. Non-limiting examples of siRNA include

```
                                        (SEQ ID NO: 88)
GGAAAGACAGCCAGAAUAGUU, (SEQ ID NO: 89)
GCCCAAGCUCCAGAUCAAACU, (SEQ ID NO: 90)
GUGGAUGGGACGCCAGUAAUU;

(SEQ ID NO: 91)
GAAGCAUUCUCGAGCUAUAGA, (SEQ ID NO: 92)
GUUUCCCCUAUUCACCAGUGU, (SEQ ID NO: 93)
GCCUCUCGCACCAUGUGAUUA, (SEQ ID NO: 94)
GACCAAGAGCGAAGGAAUGUU, (SEQ ID NO: 95)
GUUCCUCAGAUCCAAUUGUUA, (SEQ ID NO: 96)
GACCAUCUGAGCCCACUACUA, (SEQ ID NO: 97)
GGAAACAUGUGACUAUACCUU,
and (SEQ ID NO: 98)
GAUCUUUACAUAGCUUAGUGU.
```

In one embodiment, the agent is a siRNA for use in RNA interference (RNAi) mediated silencing or downregulation of MAGI-1 mRNA. RNAi agents are commonly expressed in cells as short hairpin RNAs (shRNA). shRNA is a RNA molecule that contains a sense strand, antisense strand, and a short loop sequence between the sense and antisense fragments. shRNA is exported into the cytoplasm where it is processed by dicer into short interfering RNA (siRNA). siRNA are typically 20-23 nucleotide double-stranded RNA molecules that are recognized by the RNA-induced silencing complex (RISC). Once incorporated into RISC, siRNA facilitate cleavage and degradation of targeted mRNA. Thus, for use in RNAi mediated silencing or downregulation of MAGI-1 expression, the polynucleotide agent can be either a siRNA or a shRNA. Representative but non-limiting shRNAs for use in various aspects of the instant disclosure are provided in Example 1.

shRNA can be expressed from any suitable vector such as a recombinant viral vector either as two separate, complementary RNA molecules, or as a single RNA molecule with two complementary regions. In this regard, any viral vector capable of accepting the coding sequences for the shRNA molecule(s) to be expressed can be used. Examples of suitable vectors include but are not limited to vectors derived from adenovirus, adeno-associated virus, retroviruses (e.g, lentiviruses), rhabdoviruses, murine leukemia virus, herpes virus, and the like. A preferred virus is a lentivirus. The tropism of the viral vectors can also be modified by pseudotyping the vectors with envelope proteins or other surface antigens from other viruses. As an alternative to expression of shRNA in cells from a recombinant vector, chemically stabilized shRNA or siRNAs may also be used administered as the agent in the method of the invention. Vectors for expressing shRNA which in turn produces siRNA once introduced into a cell are commercially available. Further, shRNAs or siRNAs targeted to virtually every known human gene are also known and are commercially available.

The present disclosure provides compositions comprising at least one peptide of the present disclosure. Non-limiting examples of compositions include solutions, suspensions, emulsions, solid injectable compositions that are dissolved or suspended in a solvent before use, and the like. The injections may be prepared by dissolving, suspending or emulsifying one or more of the active ingredients in a diluent. Examples of diluents, include, but are not limited to distilled water for injection, physiological saline, vegetable oil, alcohol, and a combination thereof. Further, the injections may contain stabilizers, solubilizers, suspending agents, emulsifiers, soothing agents, buffers, preservatives, etc. The injections may be sterilized in the final formulation step or prepared by sterile procedure. The composition of the disclosure may also be formulated into a sterile solid preparation, for example, by freeze-drying, and can be used after sterilized or dissolved in sterile injectable water or other sterile diluent(s) immediately before use.

The compositions may include one or more pharmaceutically acceptable carrier. Pharmaceutically-acceptable carriers include, but are not limited to, sugars, such as lactose, glucose and sucrose; starches, such as corn starch and potato starch; cellulose, including sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The composition, if desired, can also contain minor amounts of wetting or emulsifying agents, or pH buffering agents. Additional non-limiting examples of pharmaceutically acceptable carriers can be found in: *Remington: The Science and Practice of Pharmacy* (2005) 21 st Edition, Philadelphia, Pa. Lippincott Williams & Wilkins.

In an aspect, peptide of the present disclosure or composition thereof is used to alter (e.g., increase or decrease) a subject's pain sensitivity (e.g., a subject in need of treatment for pain and/or pain sensitivity). In an example, a subject's pain is decreased (e.g., ameliorated) when the subject's pain sensitivity is decreased. In another example, a subject's pain sensitivity is increased. In an example, a peptide of the present disclosure, a composition thereof, Magi-1 targeting shRNA, or Magi-1 targeting siRNA are used to manage pain (e.g., pain control).

The present disclosure further provides a method of treating a subject afflicted with pain comprising administering a peptide of the present disclosure, a composition comprising a peptide having the sequence of SEQ ID NOs:1-7, 15-21, Magi-1 targeting shRNA, or Magi-1 targeting siRNA to the subject in an amount effective to treat the pain. Treating pain includes, but is not limited to, decreasing the subject's sensitivity to pain. A subject in need of treatment may be a human or non-human mammal. Non-limiting examples of non-human mammals include cows, pigs, mice, rats, rabbits, cats, dogs, or other agricultural, pet, or service animals, and the like.

A subject's pain (e.g., pain sensitivity, pain intensity, pain relief in response to an intervention/treatment, patient ratings of improvement and satisfaction with intervention/treatment, pain interference with physical functioning, pain interference with emotional functioning) can be determined (e.g., determined at rest, during, or after activity) by description from the subject based on pain assessments using a variety of validated pain measurement tools (e.g., visual analog pain scale (VAS), numeric rating pain (NRS), categorical verbal rating pain scale (VRS), multidimensional scales assessing the sensory components and also cognitive and psychological dimensions of pain, health-related quality-of-life assessment, pain-related functional assessments). Non-limiting examples of pain measurement tools include the VAS, NRS, VRS, the McGill Pain Questionnaire (MPQ) and its Short Form, The Brief Pain Inventory (BPI), Neuropathic Pain Score (NPS), The Pain Self-Efficacy Questionnaire, Patient Global Impression of Change scale, The European Quality of Life Instrument (EQ 5D), Pain Disability Index (PDI), The Oswestry Disability Index (ODI), the Beck Depression Inventory and Profile of Mood States, the Wong-Baker faces pain scale, the FLACC scale (face, legs, activity, cry, and consolability), the CRIES scale (crying, requires $O_2$ for $SaO_2$<95%, increased vital signs (BP and HR), expression, sleepless), the COMFORT scale, Mankoski pain scale, descriptor differential scale of pain intensity, and the like, and combinations thereof. In an embodiment, the Magi-1 targeting shRNA, or Magi-1 targeting siRNA may be human Magi-1 targeting shRNA or human Magi-1 targeting siRNA.

A subject's pain may be ameliorated when the subject's pain (e.g., pain sensitivity) decreased. In example, a subject's pain is ameliorated when the subject's pain (e.g., pain sensitivity) is at a desired level (e.g., the pain is not uncomfortable).

In an added embodiment, the subject is in need of said peptide, Magi-1 targeting shRNA, or Magi-1 targeting siRNA.

In one embodiment, a subject's pain is nociceptive. In another embodiment, a subject's pain is neuropathic. A subject's pain may be a symptom of any disease, condition, or occurrence, such as injury (e.g., spinal cord injury, nerve injury, or burns), chronic disease (e.g., diabetes, Herpes zoster, major depressive disorder, fibromyalgia arthritis, or cancer), chronic inflammation (e.g., chronic inflammation associated with repetitive stress, such as, for example, carpal tunnel syndrome), chemotherapy, radiation, or Morton's neuroma. The pain may also be post-surgical pain.

In an embodiment, a subject is treated preemptively for pain (e.g., prior to anticipated pain, such as pain caused during, for example, surgery, chemotherapy, dental work, radiation treatment, and the like). In another embodiment, the subject is treated for pain following a procedure that induces pain. Such procedures include, for example, surgery, chemotherapy, radiation treatment, and the like, and combinations thereof.

In an embodiment, the subject has chronic pain and/or acute pain. Chronic pain is any pain lasting for more than around 12 weeks. In another embodiment, chronic pain is pain that extends beyond the expected period of healing.

Acute pain is sharp, and does not typically last longer than around six months. Acute pain goes away when there is no longer underlying cause of pain. Causes for acute pain include, but are not limited to, surgery, broken bones, dental work, burns, cuts, labor/childbirth, and combinations thereof, and the like.

In an embodiment, the subject does not take opioids, cannot take opioids, suffers from opioid addiction, or is at risk of relapse for opioid addiction.

In an aspect, the present disclosure provides a method of inducing local analgesia in a subject comprising administering composition comprising a peptide having the sequence of any one of SEQ ID NOs. 1-7 or 15-21, Magi-1 targeting shRNA, or Magi-1 targeting siRNA to the subject in analgesic effective amount (e.g., a therapeutically effective amount).

The present disclosure further provides a method of increasing pain sensitivity of a subject comprising administering a composition comprising a peptide having the sequence of any one of SEQ ID NOs. 8-14 or 21-35 to the subject at an amount effective to increase pain sensitivity.

In an example, a peptide of the present disclosure, a composition thereof, Magi-1 targeting shRNA, or Magi-1 targeting siRNA can be used to alter pain sensitivity locally (e.g., in an area of treatment).

The subject may be afflicted with a disease or condition having a symptom of pain hyposensitivity. Such diseases or conditions include, but are not limited to, amyotrophic lateral sclerosis, multiple sclerosis, schizophrenia, autism spectrum disorders (e.g., Asperger's syndrome and the like), congenital hyposensitivity to pain, and diabetes-induced nerve loss.

In an embodiment, one can administer or use one or more peptides of present disclosure (e.g., one or more peptide of the present disclosure that are the same or different). In another example, one or more composition comprising a peptide of the present disclosure (e.g., one or more peptide of the present disclosure that are the same or different), Magi-1 targeted shRNA, or Magi-1 targeted siRNA may be administered or used in combination with one or more analgesic and/or one or more anesthetic (e.g., lidocaine) agent and/or with an anti-inflammatory agent (e.g., glucorticoid).

When any of the foregoing are used or administered in combination, the use or administration may occur simultaneously or sequentially. Any of the foregoing may be formulated in combined formulation or in separate formulations.

An exemplary co-administration is the co-administration of i) a peptide having the sequence of any one of SEQ ID NOs:1-7, 15-21, Magi-1 targeting shRNA or Magi-1 targeting siRNA and ii) a peptide having the sequence of any one of SEQ ID NOs:8-14 or 22-35, where i) is administered after ii) or ii) is administered after i). There may be a delay between the administration of i) and ii) or ii) and i). In another example, i) is administered immediately (e.g., without delay) after ii) or ii) is administered immediately (e.g., without delay) after i). Co-administration may be used to reverse the first added peptide. For example, a subject who has been treated for pain (e.g., the subject's pain sensitivity has been decreased) using a peptide of having the sequence of any one of SEQ ID NOs:1-7 or 15-21 may administered a peptide having the sequence of any one of SEQ ID NOs: 8-14 or 22-35, such that the subject's pain sensitivity increases. In another example, if a subject is administered too much of SEQ ID NOs: 1-7 or 15-21, the subject may be administered a peptide having the sequence of any one of SEQ ID NOs:8-14 or 22-35 to increase pain sensitivity. Alternatively, if a subject is administered too much of SEQ ID NOs:8-14 or 22-35, the subject may be administered a peptide having the sequence of any one of SEQ ID NOs:1-7 or 15-21 to decrease the subject's pain sensitivity.

In an embodiment, a peptide of the present disclosure, a composition thereof, a Magi-1 targeting shRNA, or Magi-1 targeting siRNA is used for pain management.

The peptides of present disclosure, Magi-1 targeting shRNA, or Magi-1 targeting siRNA may be administered to the subject in a variety of ways. For example, they may be injected into spinal nerves or nerve endings during and/or after surgery. The peptides, Magi-1 targeting shRNA, or Magi-1 targeting siRNA may also be administered intramuscularly or intradermally. Additionally, the peptides may be administered topically. Without intending to be bound by any particular theory, the most effective route or the administration of shRNAs is administration directly into nerves.

In an embodiment, one or more compound and/or one or more composition comprising one or more compound described herein is administered to a subject in need of treatment using any known method and route, including, but not limited to, oral, parenteral, subcutaneous, intraperitoneal, intrapulmonary, intranasal and intracranial injections. Parenteral infusions include, but are not limited to intramuscular, intravenous, intraarterial, intraperitoneal, and subcutaneous administration. Topical and/or transdermal administrations are also encompassed. Further encompassed are methods of application involving needleless injections.

In an embodiment, a subject in need of treatment is administered a therapeutically effective amount of a peptide of the present disclosure, a Magi-1 targeting shRNA, or Magi-1 targeting siRNA. A dose of a therapeutically effective amount of a peptide of the present disclosure may have a concentration of 10 nM to 10 mM (e.g., 100 μM), including all 0.1 nM values and ranges therebetween. In an embodiment, a dose of a therapeutically effective amount of a peptide of the present disclosure may have a concentration of 1-500 μM, 50-500 μM, 1-250 μM, 10-250 μM, 25-250 μM, 25-150 μM, 50-250 μM, or 50-150 μM.

In an embodiment, a subject in need of treatment is administered a peptide of the present disclosure, a composition thereof, a Magi-1 targeting shRNA, or a Magi-1 targeting siRNA as a single dose (e.g., a single administration step). Following a single dose, the subject's pain is ameliorated or the subject's pain sensitivity is increased for 1-120 hours (hr(s) or h) (e.g., 24-120 hours, 1-48 hours, 12-48 hours, or 24-48 hours), including all second values and ranges therebetween. In another example, the subject's pain is ameliorated or the subject's pain sensitivity is increased in the absence of any other active components (e.g., an additional analgesic agent and/or an anesthetic agent) for 1-120 hours (e.g., 24-120 hours, 1-48 hours, 12-48 hours, or 24-48 hours), including all second values and ranges therebetween.

In an embodiment, a subject in need of treatment is administered a peptide of the present disclosure, a composition thereof, a Magi-1 targeting shRNA, or a Magi-1 targeting siRNA in multiple doses dose (e.g., multiple administration steps). Following the multiple doses, the subject's pain is ameliorated or the subject's pain sensitivity is increased for 1-120 hours (e.g., 24-120 hours, 1-48 hours, 12-48 hours, or 24-48 hours), including all second values and ranges therebetween. In another example, the subject's pain is ameliorated or the subject's pain sensitivity is increased in the absence of any other active components (e.g., an additional analgesic agent and/or an anesthetic agent) for 1-120 hours (e.g., 24-120 hours, 1-48 hours, 12-48 hours, or 24-48 hours), including all second values and ranges therebetween.

In an aspect, the disclosure further provides kits.

In an embodiment, a kit comprises pharmaceutical preparations containing any one or any combination of compounds of the present disclosure.

In an embodiment, the kit comprises a package (e.g., a closed or sealed package) that contains a pharmaceutical preparation, such as, for example, one or more closed or sealed vials, bottles, blister (bubble) packs, or any other suitable packaging for the sale, distribution, or use of the pharmaceutical compounds and compositions comprising them.

In an embodiment, the printed material includes, but not limited to, printed information. The printed information may be provided on a label, or on a paper insert, or printed on the packaging material itself. The printed information may include information that, for example, identifies the composition in the package, the amounts and types of other active and/or inactive ingredients, and instructions for taking the composition, such as, for example, the number of doses to take over a given period of time, and/or information directed to a pharmacist and/or another health care provider, such as a physician, or a patient. The printed material may include, for example, an indication that the pharmaceutical composition and/or any other agent provided with it is for treatment of a subject having a bacterial infection. In an example, the product includes a label describing the contents of the container and providing indications and/or instructions regarding use of the contents of the container to treat a subject having any bacterial infection.

In an aspect, the present disclosure further provides peptides of SEQ ID NOs:36-70 for use as research tools. As such, they can be administered to research subjects, such as mice and rats. The peptides are also useful for in vitro testing.

In the following Statements, various examples of the peptides, compositions, and methods of using the peptides and compositions of the present disclosure are described:

Statement 1. A peptide comprising the following sequence:

$$X^1X^2X^3X^4X^5X^6PX^7YX^8X^9VX^{10}X^{11}X^{12}, \text{ (SEQ ID NO: 75)}$$

wherein $X^1$ is chosen from S, P, and A;
$X^2$ is chosen from T, S, and A;
$X^3$ is chosen from A and T;
$X^4$ is chosen from A, T, I, and S;
$X^5$ is chosen from C, S, and F;
$X^6$ is chosen from P and L;
$X^7$ is any amino acid residue;
$X^8$ is chosen from E, D and Y;
$X^9$ is chosen from S and R;
$X^{10}$ is chosen from T, A, E, and D, and T is optionally phosphorylated;
$X^{11}$ is chosen from K and R; and
$X^{12}$ is chosen from P, A, and G,
wherein $X^1$, $X^2$, $X^3$, $X^4$, $X^{10}$, $X^{11}$, or a combination are acylated

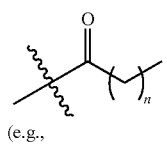

(e.g., and n is 4-18 (e.g., 4, 5, 6, 7, 8, 9, 10, 11, 12, 13, 14, 15, 16, 17, or 18), such as, for example, a myristoyl group).

Statement 2. The peptide according to Statement 1, where $X^1$ is chosen from S and P.

Statement 3. The peptide according to Statement 2, where the peptide has a sequence chosen from SEQ ID NO: 1-7 and 15-21.

Statement 4. The peptide according to Statement 2, where the peptide has a sequence chosen from SEQ ID NO: 8-14 and 22-35.

Statement 5. The peptide according to any one of the preceding Statements, where the peptide has the following sequence:
$X^1X^2X^3X^4X^5PPSYX^8X^9VX^{10}X^{11}X^{12}$ (SEQ ID NO:75, $X^6$ is S and $X^7$ is S), where $X^1$ is myristoylated.

Statement 6. The peptide according to any one of the preceding Statements, where the peptide has the following sequence:
$SX^2X^3X^4X^5PPSYX^8X^9VX^{10}X^{11}X^{12}$ (SEQ ID NO:75, where $X^1$ is S, $X^6$ is P, and $X^7$ is S), where S is myristoylated.

Statement 7. The peptide according to any one of the preceding Statements, where the peptide has the following sequence: (myristoyl)-SSTTSPPSYDSVTKP (SEQ ID NO:6), (myristoyl)-SATSFPPSYESVTRG (SEQ ID NO:7), (myristoyl)-SSTTSPPSYDSVT^KP (SEQ ID NO:13), (myristoyl)-SATSFPPSYESVT^RG (SEQ ID NO:14), (myristoyl)-SSTTSPPSYDSVAKP (SEQ ID NO:20), (myristoyl)-SATSFPPSYESVARG (SEQ ID NO:21), (myristoyl)-SSTTSPPSYDSVEKP (SEQ ID NO:27), (myristoyl)-SATSFPPSYESVERG (SEQ ID NO:28), (myristoyl)-SSTTSPPSYDSVDKP (SEQ ID NO:34), or (myristoyl)-SATSFPPSYESVDRG (SEQ ID NO:35), wherein the residue is myristoylated, it is indicated by (myristoyl)- and ^ denotes the T immediately preceding the "^" is phosphorylated.

Statement 8. A composition comprising one or more peptide according to any one of the preceding Statements and a carrier.

Statement 9. The composition according to Statement 8, comprising at least two peptides according to any one of Statements 1-7, where the at least two peptides are the same or different.

Statement 10. The composition according to Statements 8 or 9, further comprising one or more analgesic agent and/or one or more anesthetic agent.

Statement 11. The composition according to Statement 10, where the one or more analgesic and/or one or more anesthetic agent is bupivacaine, etidocaine, levobupivacaine, lidocaine, mepivacaine, prilocaine, ropivacaine, procaine, chloroprocaine, meloxicam, ketorolac, diclofenac, ketoprofen, piroxicam, metamizole, or a combination thereof.

Statement 12. The composition according to any one of Statements 8-11, where the carrier is a pharmaceutically acceptable carrier.

Statement 13. A method of treating pain or increasing pain sensitivity in a subject in need of treatment comprising: administering to the subject in need of treatment a therapeutically effective amount of one or more peptide of any one of Statements 1-7 and/or one or more composition according to any one of Statements 8-12, wherein pain of the subject in need of treatment is ameliorated or the pain sensitivity of the subject in need of treatment is increased.

Statement 14. The method according to Statement 13, where the subject's pain is chronic pain.

Statement 15. The method according to Statement 13, where the subject's pain is acute pain.

Statement 16. The method according to any one of Statements 13-15, where the administration step is performed in anticipation of pain Statement 17. The method according to any one of Statements 14-16, where the subject in need of treatment has an injury, a chronic disease, a chronic inflammation, Morton's neuroma, post-operative pain, or a combination thereof.

Statement 18. The method according to Statement 17, where the injury is a spinal cord injury, a nerve injury, a burn, or a combination thereof.

Statement 19. The method according to Statement 17, where the chronic disease is diabetes, Herpes zoster, major depressive disorder, fibromyalgia arthritis, amyotrophic lateral sclerosis, multiple sclerosis, schizophrenia, autism spectrum disorders, cancer, or a combination thereof.

Statement 20. The method according to any one of Statements 14-19, where the administering step induces an increase or decrease in sodium current.

Statement 21. The method according to any one of Statements 14-20, where the peptide administered to the subject has a sequence chosen from SEQ ID NOs: 1-7, 15-21, and combinations thereof.

Statement 22. The method according to any one of Statements 14-21, where the subject's pain is ameliorated (e.g., the subject's pain sensitivity is decreased).

Statement 23. The method according to any one of Statements 14-22, where subject's pain is ameliorated (e.g., the subject's pain sensitivity is decreased) for 1-120 hours following a single administration step.

Statement 24. The method according to any one of Statements 14-23, where subject's pain is ameliorated (e.g., the subject's pain sensitivity is decreased) for 24-120 hours following a single administration step.

Statement 25. The method according to any one of Statements 14-20, where the subject's pain sensitivity is increased.

Statement 26. The method according to any one of Statements 14-20 or 25, where the peptide administered to the subject has a sequence chosen from SEQ ID NOs:8-14, 22-35, and combinations thereof.

Statement 27. The method according to any one of Statements 14-20, 25, or 26, where the subject's pain sensitivity is increased for 1-120 hours following a single administration step.

Statement 28. The method according to any one of Statements 14-20 or 25-27, where the subject's pain sensitivity is increased for 24-120 hours following a single administration step.

Statement 29. The method according to any one of Statements 14-20 or 25-28, where the subject is administered a peptide having a sequence chosen from SEQ ID NOs:1-7, 15-21, and combinations thereof, followed by a peptide having a sequence chosen from SEQ ID NOs:8-14, 22-35, and combinations thereof.

Statement 30. The method according to any one of Statements 14-20 or 25-29, where the subject is administered a peptide having a sequence chosen from SEQ ID NOs:8-14, 22-35, and combinations thereof, followed by a peptide having a sequence chosen from SEQ ID NOs:1-7, 15-21, and combinations thereof.

Statement 31. The method according to any one of Statements 14-30, where the administering step comprises administering one or more of the follow sequences: (myristoyl)-SSTTSPPSYDSVTKP (SEQ ID NO:6), (myristoyl)-SATSFPPSYESVTRG (SEQ ID NO:7), (myristoyl)-SSTTSPPSYDST^KP (SEQ ID NO:13), (myristoyl)-SATSFPPSYESVT^RG (SEQ ID NO:14), (myristoyl)-SSTTSPPSYDSVAKP (SEQ ID NO:20), (myristoyl)-SATSFPPSYESVARG (SEQ ID NO:21), (myristoyl)-SSTTSPPSYDSVEKP (SEQ ID NO:27), (myristoyl)-SATSFPPSYESVERG (SEQ ID NO:28), (myristoyl)-SSTTSPPSYDSVDKP (SEQ ID NO:34), or (myristoyl)-SATSFPPSYESVDRG (SEQ ID NO:35), wherein the residue is myristoylated, it is indicated by (myristoyl)- and ^ denotes the T immediately preceding the "^" is phosphorylated.

The following example is presented to illustrate the present disclosure. It is not intended to be limiting in any matter.

Example 1

This example provides a description of peptides of the present disclosure and uses thereof.

Disclosed are the consequences of Magi-1 deficiency on pain sensitivity. It was demonstrated that membrane targeting of $Na_V1.8$ and $K_{Na}$ channels is dependent upon Magi-1. The expression and distribution of Magi-1 in DRG neurons was characterized and found that knockdown of Magi-1 caused a reduction in sodium ($I_{Na}$) and potassium ($I_K$) currents and diminished excitability in neurons. It was also determined that $Na_V1.8$ and Slack $K_{Na}$ channels are complexed together. In vivo knockdown of Magi-1 suppressed pain behaviors and produced a significant loss of $Na_V1.8$ channel protein expression. Finally, using WW motif cell-penetrating peptidomimetics, it described that $Na_V1.8$ channel trafficking can be pharmacologically manipulated.

Figure 1:
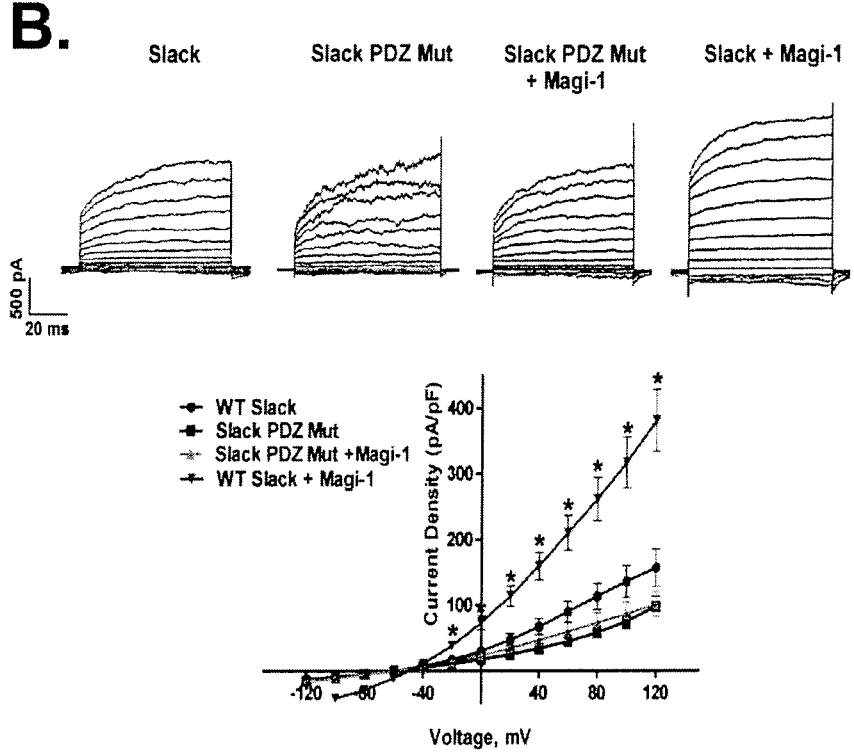
FIG. 1 shows PDZ binding motif regulates $K_{Na}$ channel expression. (A) Amino acid alignment of the distil C-termini from orthologous Slack subunits (Xenopus, chicken, rat, and human Slack) and the rat Slick subunit. The final four, evolutionarily conserved amino acids (ETQL) (SEQ ID NO: 112) (long and short dashed line on the C-terminus) represent a consensus Type 1 PDZ motif (X-S/T-X-V/L/I). (solid box indicates AP-2 binding site; dotted box indicates putative PKA phosphorylation site; dashed-line box indicates putative PKC phosphorylation site) (B) Representative current traces of Slack and mutated Slack channels (Mut) where the PDZ motif was truncated, recombinantly expressed in CHO cells with or without Magi-1 (top). Current density analysis for each experimental conditions (bottom). For each experimental condition currents from 20-25 cells were analyzed and values expressed as +/−SEM, *p<0.05, vs. respective controls. (C) Co-immunoprecipitation assay of Magi-1 with wildtype and a mutant Slack variant with a truncated PDZ motif. Truncating the Slack PDZ motif prevented co-immunoprecipitation with Magi-1. (D) Representative immunoblot of surface biotinylation assay from CHO cells co-expressing Magi-1 with Slack or Slack alone, (left). Quantification of surface Slack expression is shown on the right (16=4.276, *p<0.0129, n=4 per group, two-tailed t test). Data was normalized to input to account for transfection efficiency (E) Double immunolabeling experiments showing overlapping expression between Magi-1 and Slack and F. Magi-1 and Slick when expressed in CHO cells. (F) Representative immunoblots of co-immunoprecipitation assay between Magi-1 and Slack from intact DRG neurons from adult mice. (G) Double immunolabeling experiments depicting co-localization between Magi-1 and Slack in cultured DRG neurons (upper panels), and intact DRG neurons (lower panels). Scale bar, 50 μm. The superficial laminae of the spinal cord is on the bottom. The scale bar represents 50 μm. (H) Co-IP showing Magi-1/Slack interaction in mouse DRGs. DRG lysate was immunoprecipitated with either Magi-1 antibody or Slack antibody, and immunoblotted with Slack or Magi-1 antibody as indicated. This experiment was repeated at least three times. (I) Top, Representative current clamp traces of neurons treated with the PDZ peptide derived from the Slack C-terminal. Scrambled peptide B (myristoyl-QPNTRLDETE) (SEQ ID NO: 113) (23/23) (top left) and untreated neurons (17/17) (top middle) fired one action potential followed by firing accommodation during suprathreshold stimulation (400 pA) for 1000 ms. Neurons treated with PDZ peptide exhibited repetitive firing (11/21) (top right). Surface biotinylation showing decreased Slack surface expression 24 hrs after PDZ peptide incubation compared to the scrambled peptide B in DRG neurons (bottom left). Quantification of surface Slack expression (bottom right). (n=3) *p<0.05 One-way ANOVA.
Figure 1:
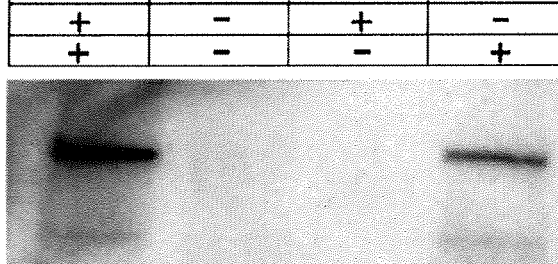
Figure 1:
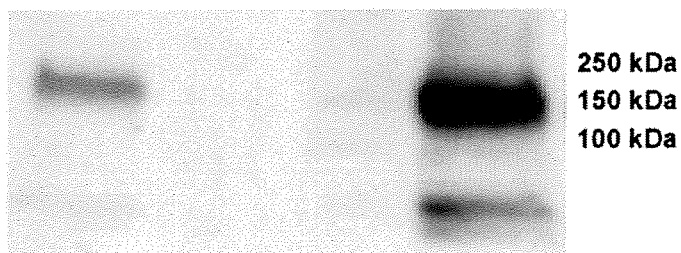
Figure 1:
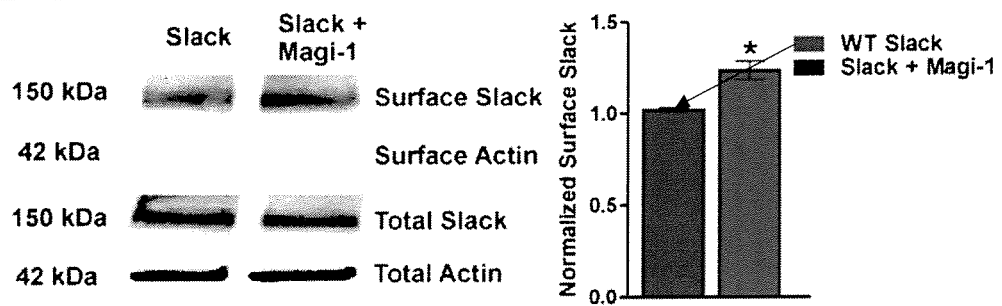
Figure 1:
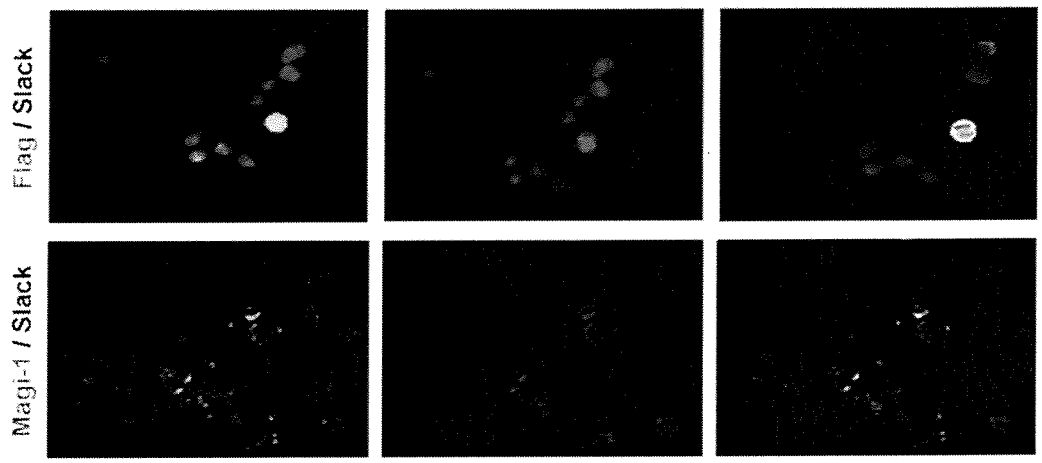
Figure 1:
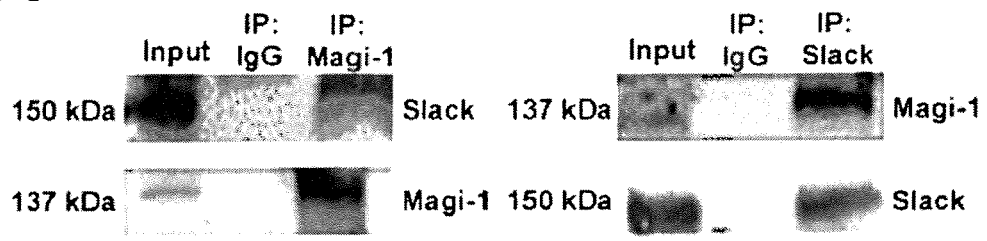
Figure 1:
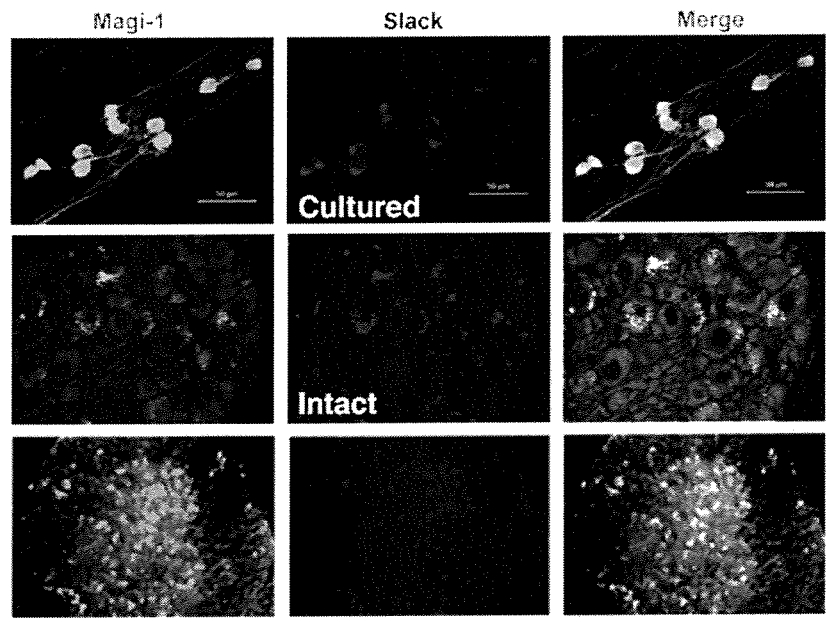
Figure 1:
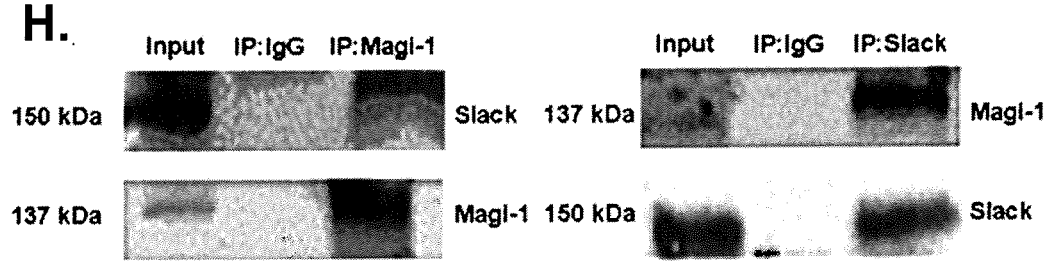
Figure 1:
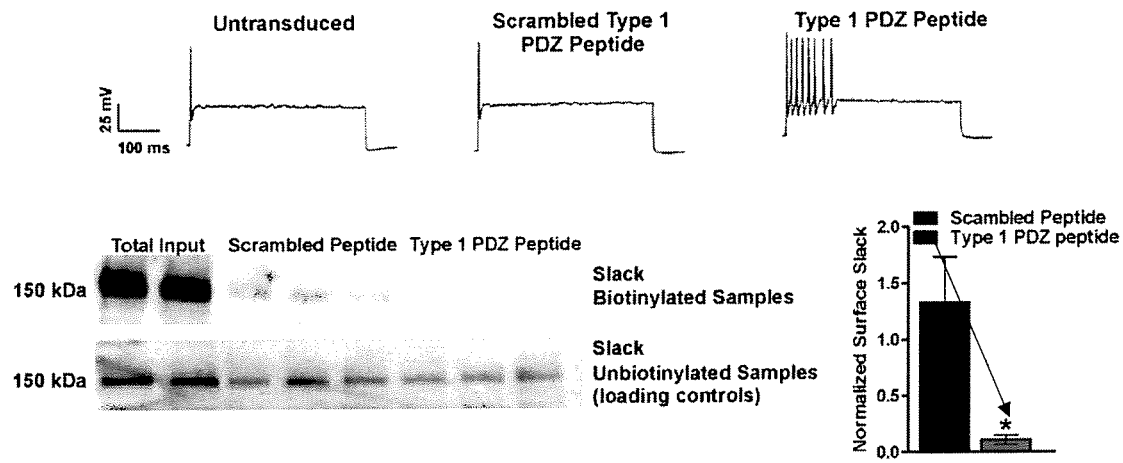

$K_{Na}$ channel expression is affected by the PDZ binding motif Slack and Slick channels contain a type 1 PDZ binding motif at their respective distil C-termini (FIG. 1A). Using the PDZ protein interactive predictor (PDZPedInt, University of Freiburg), and inputting the Slack amino acid sequence Magi-1 was identified as a Slack channel interactor, specifically the second and fifth PDZ domain of Magi-1. Heterologous co-expression of Magi-1 and the Slack-B subunit, increased Slack current density (FIG. 1B), however, co-expression of Magi-1 with a mutated Slack construct with a truncated PDZ motif did not affect Slack current density (FIG. 1B). We confirmed that Magi-1 interacted with Slack channels in Chinese hamster ovary (CHO) cells and in DRG neurons using co-immunoprecipitation (Co-IP) assays (FIG. 1C,F). Double-immunolabeling studies depicted co-localization between Magi-1 and Slack $K_{Na}$ channels in CHO cells, in cultured and intact DRG neurons (FIG. 1E,G). It was confirmed by Co-IP that Slack $K_{Na}$ channels interacted with Magi-1 via its C-terminal PDZ motif (ETQL (SEQ ID NO:99)) (FIG. 1C). To verify the role of Magi-1 on Slack channel membrane expression, a surface biotinylation assay was performed and confirmed that co-expression of Slack with Magi-1 increased Slack channel surface expression (FIG. 1D). Slick, the other member of the $K_N$a family of channels, which shares approximately 74% sequence homology to Slack, has the same evolutionarily conserved, Class 1 PDZ binding motif (ETQL) (FIG. 1A). It was assessed whether Magi-1 also modulated Slick current activity in CHO cells by co-expressing Magi-1 and Slick. Patch-clamp recordings revealed that Magi-1 similarly potentiated Slick current density FIG. 2A), but differing with Slack-B, Western analysis surprisingly showed an increased total Slick protein expression (8-fold) (FIG. 2C). Magi-1 was also found to co-localize with Slick channels when heterologously expressed in CHO cells (FIG. 2D). Therefore, Magi-1 influenced $K_{Na}$ currents by increasing Slack channel membrane expression and with respect to Slick channels: Magi-1 seemed to serve an additional protein stabilizing function as Magi-1 expression resulted in increased total Slick channel protein expression.

Figure 3:
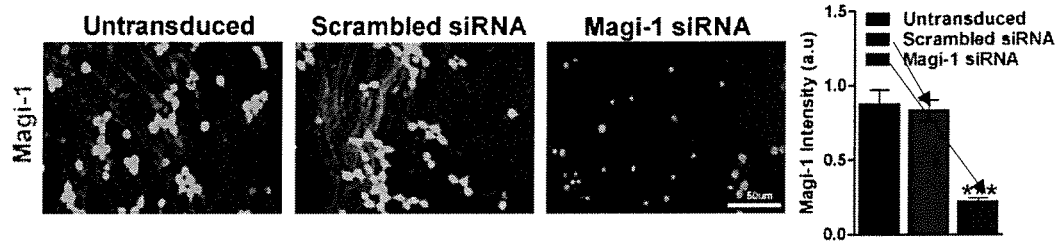
FIG. 3 shows Magi-1 knockdown decreases ionic currents and excitability in DRG neurons. (A) Representative Magi-1 immunolabeling from cultured DRG neurons 3 days after transfection with Magi-1 targeting siRNA and non-targeting scrambled siRNA (left) using a previously validated polyclonal Magi-1 antibody. Quantification of Magi-1 immunoreactivity shown on the right. The integrated fluorescence intensity was calculated as the product of the area and the mean pixel intensity using Metamorph software (Molecular devices). Values from four independent DRG neuronal cultures per experimental condition were analyzed and values and expressed mean+/−SEM. (ANOVA, $F_{(2,11)}$=32.25, p<0.0003, *p<0.001 vs. respective controls. (B) Representative immunoblots depicting Magi-1 expression after siRNA mediated Magi-1 knockdown. Magi-1 antibodies normally detect multiple splice variants as indicated by the multiple bands observed on Western blot. Quantification of Magi-1 knockdown in DRG neurons (right). Three different cultures per experimental condition were analyzed and values expressed as mean+/−SEM. (ANOVA, $F_{(2,6)}$=42.94, p=0.0003, *p<0.001 vs. respective controls. (C) Representative immunoblots of surface biotinylation from DRG neurons after Magi-1 knockdown (left). Quantification of Slack channel surface expression is shown on the right. Three independent cultures were analyzed and values expressed as mean+/−SEM. (ANOVA, $F_{(2,6)}$=10.84, P=0.0102, **p<0.01 vs respective controls. (D) Representative current traces of $I_K$ in DRG neurons after Magi-1 knockdown (top). 11-12 neurons/experimental condition were analyzed and values expressed as mean+/−SEM. *p=<0.05. (E) Representative AP firing from neurons after siRNA mediated Magi-1 during suprathreshold current stimulation (400 pA) for 1000 ms, untransduced (10/10), scrambled DRG neurons 12/12 fire 1 AP whereas 12/18 neurons transfected with Magi-1 siRNA failed to fire a single AP.
Figure 3:
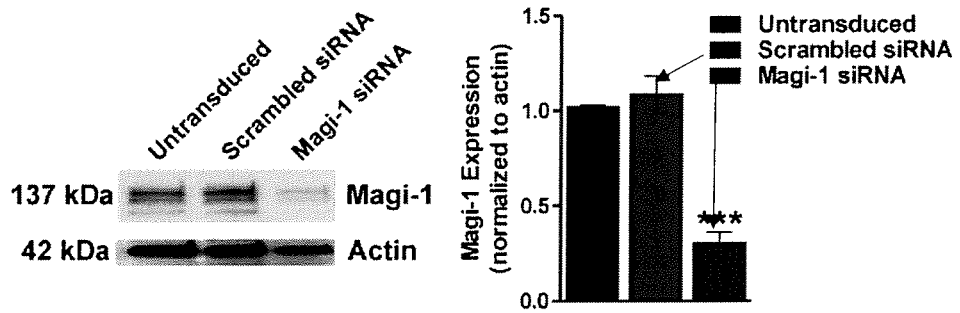
Figure 3:
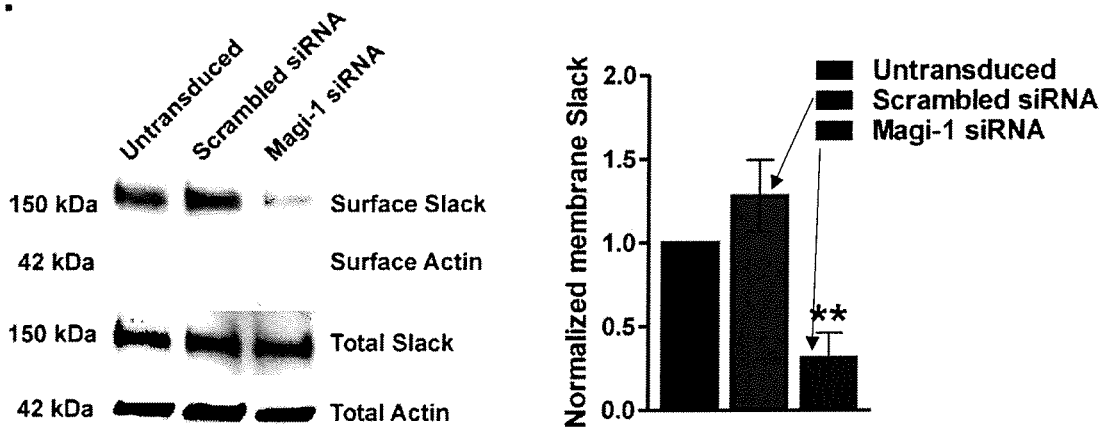
Figure 3:
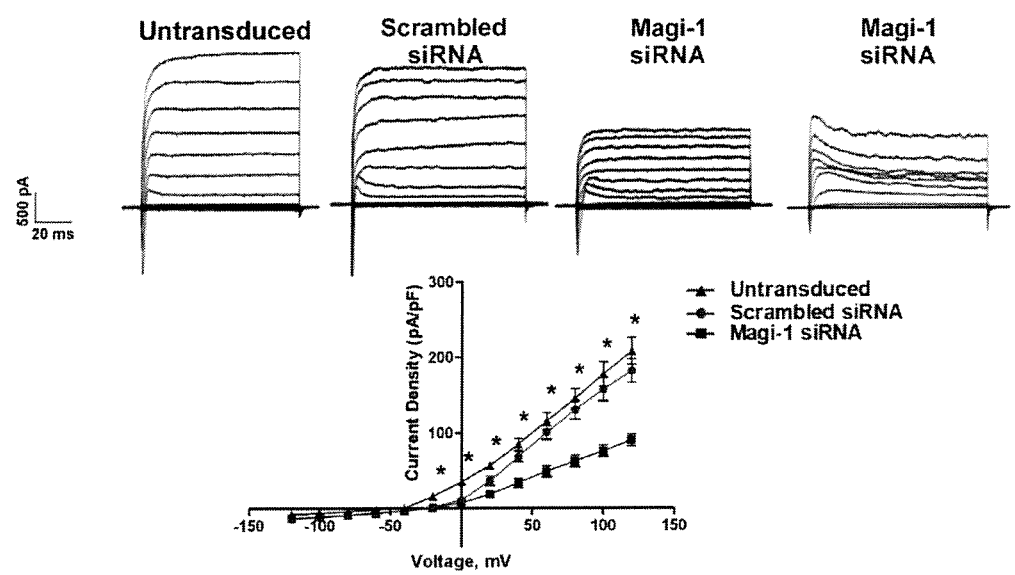
Figure 3:
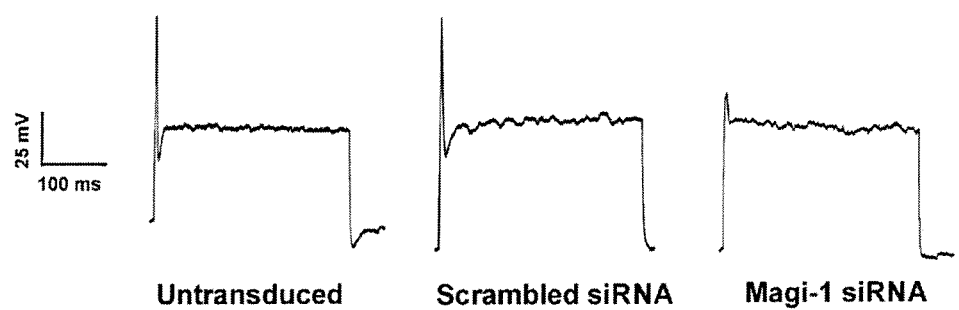

Magi-1 knockdown suppressed $I_K$ but produced hypoexcitability in cultured DRG neurons. The neurophysiological function of Magi-1 was examined by using knockdown strategies, with previously validated small interfering RNAs (siRNAs) in cultured DRG neurons. Magi-1 knockdown was verified by immunolabeling and Western blot analyses (FIGS. 3A,B) using a previously validated polyclonal Magi-1 antibody. Substantial Magi-1 knockdown was achieved as it was observed approximately 70-75% reduction in Magi-1 protein when compared to a non-coding scrambled control siRNA 72 hrs after transfection (FIGS. 3A,B). Additional immunofluorescence images depicting knockdown can be found in FIG. 10. We examined the consequences of Magi-1 knockdown on $K_{Na}$ Slack channel surface expression. Membrane biotinylation assays revealed a significant decrease in membrane Slack channel expression ~70% compared to controls (FIG. 3C). Voltage-clamp recordings also showed a significant reduction in outward $I_K$ density after Magi-1 knockdown although the transient $I_K$ was still present (FIG. 3D). Surprisingly, Magi-1 knockdown resulted in DRG hypoexcitability with neurons failing to fire APs (FIG. 3E and FIG. 11A). It was expected that the decrease in surface Slack $K_{Na}$ channels to result in repetitive firing, however, the observed severely stunted action potentials suggested that Magi-1 deficiency was also affecting sodium channel functioning.

Figure 4:
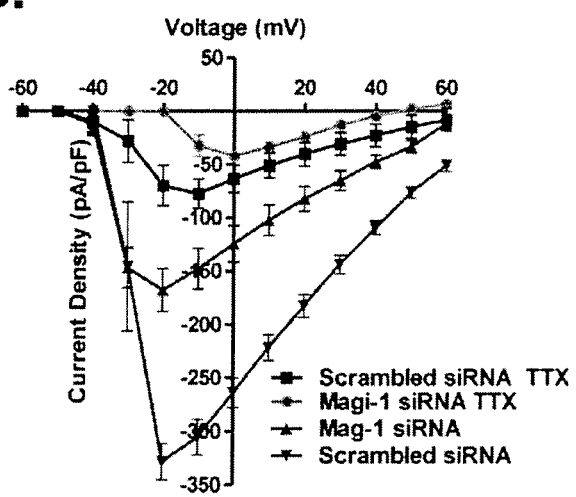
FIG. 4 shows Magi-1 knockdown decreases $Na_v1.8$ plasma membrane expression. (A) Representative whole cell voltage-clamp current traces of total $I_{Na}$ and TTX-resistant $I_{Na}$ in cultured DRG neurons 3 days after transfection with Magi-1 targeting siRNA or non-targeting scrambled siRNA. (B) Current density analysis of $I_{Na}$ currents with different conditions. Sodium currents in neurons were recorded either in the presence or absence of 25 nM TTX. The total and TTX-resistant $I_N$a was significantly reduced after siRNA mediated-Magi-1 knockdown in cultured DRG neurons. A total of 9-12 cells/experimental group were analyzed and values are expressed as mean+/−SEM. (C) Quantification of peak $I_{Na}$ and TTX-resistant peak $I_{Na}$ (at voltage step −20 mV) after Magi-1 knockdown. 9-12 cells/experimental group were analyzed and values expressed as mean+/−SEM. F $(3,26)$=66.24 P<0.0001 *p<0.0106, ***p<0.001 vs respective controls (scrambled siRNA with or without TTX). (D) Representative immunoblots from surface biotinylation experiments of DRG neurons depicting reduced Na$_V$1.8 surface expression after Magi-1 knockdown (left). Quantification of Na$_V$1.8 surface expression is shown on the right. For quantification four independent DRG cultures per experimental condition were analyzed and values expressed as +/−SEM. (ANOVA $F_{(2,6)}$=7.319, p=0.0246 *p<0.05 vs respective controls.
Figure 4:
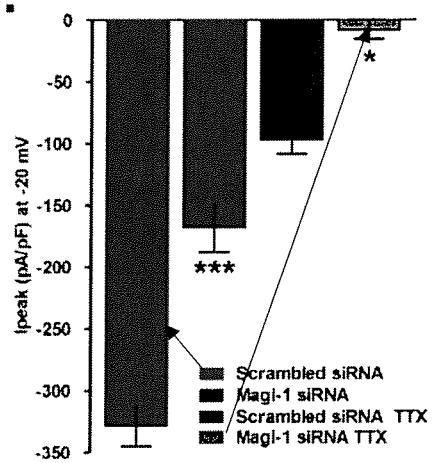
Figure 4:
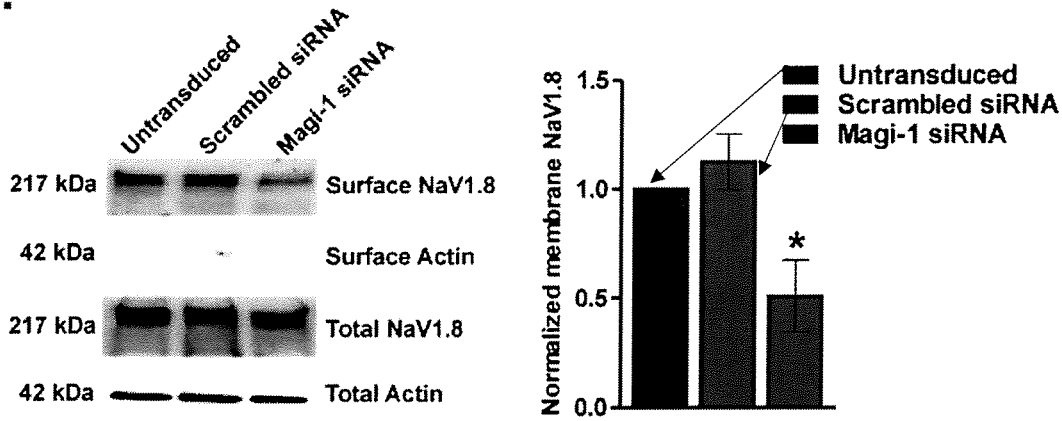

Magi-1 knockdown also decreased Iva and $Na_V1.8$ plasma membrane expression in DRG neurons. The effects of Magi-1 knockdown were examined on the inward sodium current ($I_{Na}$) in DRG neurons using whole-cell voltage-clamp recordings. Magi-1 knockdown produced a significant reduction in total $I_{Na}$ (FIGS. 4A-C). The peak tetrodotoxin (TTX)-sensitive and the TTX-resistant components of $I_{Na}$ were both significantly reduced compared to neurons treated with control siRNA accounting for the hypoexcitability phenotype seen in DRG neurons during Magi-1 knockdown despite decreased membrane Slack expression. Notably, the culture conditions of these DRG neurons favor TrkA positive, nociceptive DRG neurons (see Methods) that express high levels of $Na_V1.8$ channels. In most mature nociceptive DRG neurons, $Na_V1.8$ channels account for up to 90% of the upstroke of the action potential. Since Magi-1 knockdown reduced the TTX-resistant component of the $I_{Na}$, of which $Na_V1.8$ is a significant contributor, the investigation was concentrated on the surface expression of $Na_V1.8$. Using surface biotinylation assays, decreased membrane expression of $Na_V1.8$, (~50%) was found, after Magi-1 knockdown (FIG. 4D). Together, these results suggested that Magi-1 is an essential scaffold for the membrane localization of both $Na_V1.8$ and Slack channels in DRG neurons.

Magi-1 is expressed in small- and medium-sized DRG neurons, in their axonal tracts and at some Nodes of Ranvier. The expression of Magi-1 in intact DRG neurons was verified for indication of its broader physiological function. The Allen Mouse Spinal Cord Atlas and BioGPS support high Magi-1 message within DRG neurons. According to BioGPS DRG tissue has the second highest Magi-1 mRNA tissue expression profile, with the hypothalamus accounting for the highest expression. Moreover, the Allen Spinal Cord Atlas depicts differential Magi-1 expression in small- and medium-sized, presumably nociceptive DRG neurons. Magi-1 immunolabeling was also previously shown in the growth cones of cultured DRG neurons and within the dorsal root entry zone of embryonic spinal cords. We confirmed Magi-1 expression in adult mouse DRG neurons and spinal cord tissue by Western blot (FIG. 5A) and immunohistochemistry analyses (FIG. 5B). Immunohistochemistry was performed using a previously validated monoclonal anti-Magi-1 antibody. Histological examination of the sciatic nerve showed high Magi-1 immunoreactivity along axonal fibers, and at some Nodes of Ranvier using the paranodal marker Caspr (FIG. 5C). Cell size analysis indicated highest distribution of Magi-1 in DRG neurons within small- and medium-sized DRG neurons (<600 um$^2$) (FIG. 5D) similar to the data that can be found in the Allen Mouse Spinal Cord Atlas. The preferential tissue expression profile of Magi-1 to small- and medium-size DRG neurons and the dorsal horn of the spinal cord indicated a potential function for Magi-1 in pain signaling.

Magi-1 mediated coupling between Slack $K_{Na}$ channels and $Na_V1.8$ in DRG neurons. Previous reports showed that neuronal $K_{Na}$ channel activity decreased when sodium entry pathways were blocked, suggesting that $Na_V$ channels reside in close proximity to $K_{Na}$ channels. Moreover, a co-immunolocalization was previously observed between the Slack $K_{Na}$ channel and $Na_V1.8$ in DRG neurons. These data also suggested possible coupling as indicated by decreased membrane localization of $Na_V1.8$ and Slack channels after Magi-1 knockdown. The possibility of Magi-1 interacting with $Na_V1.8$ in DRG neurons was examined and whether Magi-1 facilitated a coupling of $Na_V1.8$ with Slack $K_{Na}$ channels. In Co-IP assays, it was confirmed that Magi-1 interacted with $Na_V1.8$ channels (FIG. 6A). Double immunolabeling studies also depicted a co-localization between Magi-1 and $Na_V1.8$ in cultured and intact DRG neurons and within the spinal cord (FIG. 6B). Co-IP experiments using Slack and $Na_V1.8$ specific antibodies from intact DRG lysates were performed and successfully co-immunoprecipitated Slack with $Na_V$ 1.8 (FIG. 6C) indicating that $Na_V1.8$ and Slack $K_{Na}$ channels are complexed together in DRG neurons. These findings implicated the scaffolding of Slack and $Na_V1.8$ in sensory neurons by Magi-1.

Figure 7:
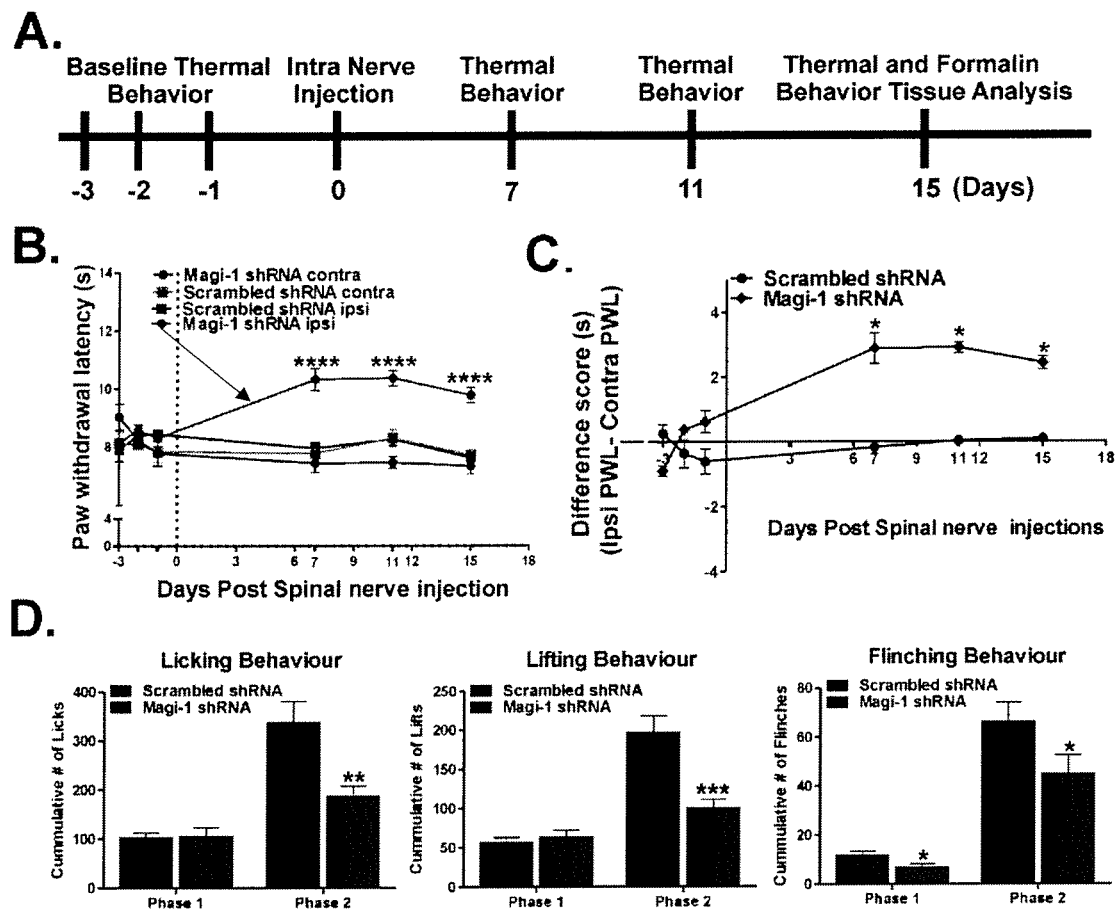
FIG. 7 shows in vivo Magi-1 knockdown attenuates thermal nociception and acute inflammatory pain behavior. (A) Experimental timeline before and after Magi-1 knockdown in vivo. (B) Hargreaves test for thermal nociception showed increased paw withdrawal latency in ipsilateral paw injected with Magi-1 targeting shRNA when compared to the contralateral paw. No significant difference was seen in paw withdrawal latency between paws in mice injected with non-targeting shRNA. Behavior was taken from nine (9) different animals (3 females and 6 males) per experimental condition and analyzed. Values are expressed as mean+/−SEM. ***p<0.001 vs respective controls. (C) Difference score analysis determined a ~3 sec difference in withdrawal latency between ipsilateral and contralateral paw after Magi-1 shRNA in vivo transfection (Days 7, 11 and 15).
Figure 7:
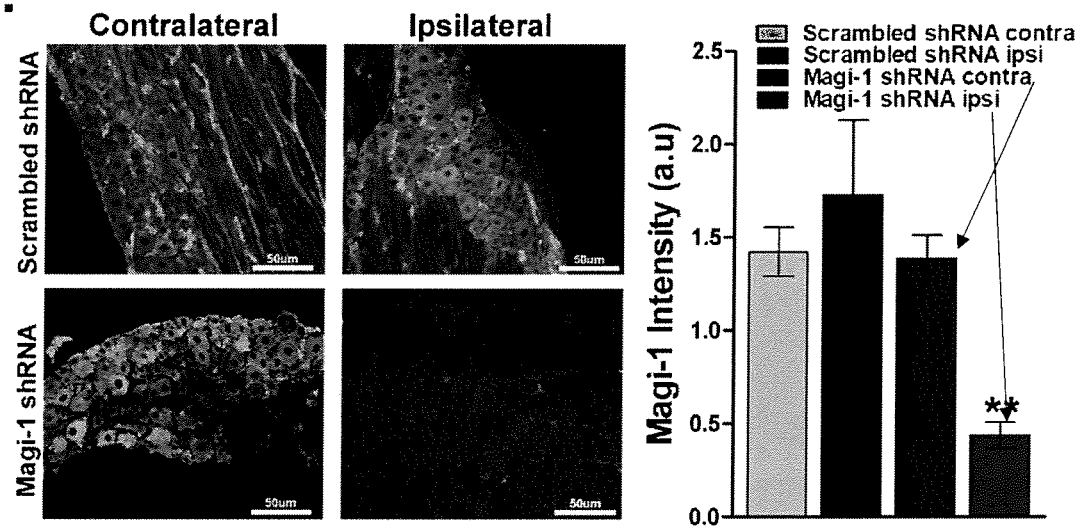
Figure 7:
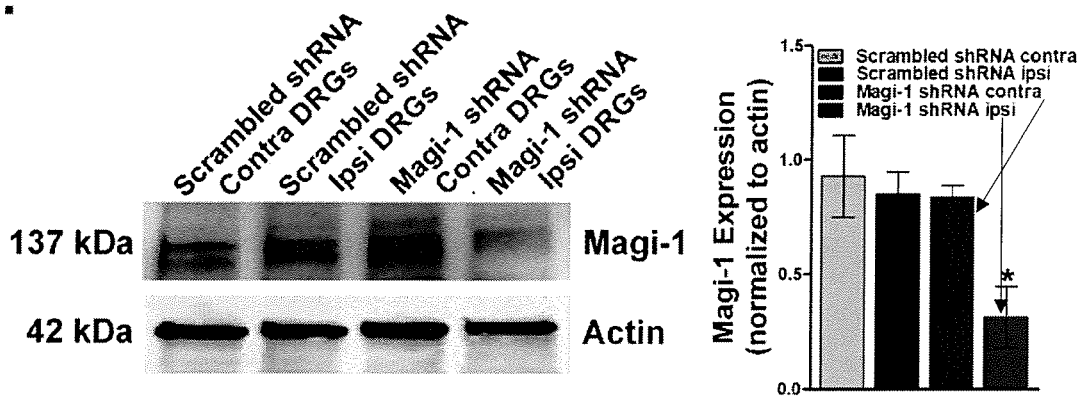

In vivo Magi-1 knockdown in DRG neurons reduced pain sensitivity. The ability of in vivo knockdown of Magi-1 to attenuate pain behavior was examined. A novel spinal nerve injection technique of non-viral vectors containing short hairpin RNA (shRNA) sequences was used. This disclosure is the first to describe this in vivo transfection method for mice, and the technique allows for shRNA plasmid uptake by DRG sensory neurons via axonal retrograde transport but did not require invasive paraspinal muscle dissection that is necessary for rats. The schematic representation of the experimental outline is depicted in FIG. 7A. Intra-spinal nerve injection of Magi-1 shRNAs in naïve male and female mice induced a marked and persistent reduction in thermal nociception compared to control shRNA (FIGS. 7B,C). To assess the intra-animal differences with respect to withdrawal latency the contralateral (un-injected) paw withdrawal latency (PWL) was subtracted from the ipsilateral (injected) PWL. Within individual animals, there was a significant ~3-second increase in PWL in mice injected with Magi-1 shRNA compared to paw injected with non-targeting shRNA. The effects of Magi-1 knockdown in an acute inflammatory pain model (formalin assay) were examined next. Intraplantar (i.pl.) injection of 5% formalin induced the typical biphasic inflammatory pain responses associated with this acute inflammatory pain model. To this extent, fifteen days after Magi-1 shRNA in vivo transfection, phase I flinching behavior and phase II licking, lifting and flinching behaviors were all significantly reduced (FIG. 7D).

In vivo Magi-1 silencing fifteen days after transfection within the DRG and sciatic nerve of shRNA injected mice was confirmed by immunohistochemical and biochemical analyses. A significant loss of Magi-1 immunoreactivity in the ipsilateral DRG and sciatic nerves was observed from mice injected with Magi-1 shRNA when compared to contralateral DRG from the same mouse, and mice injected with control shRNA (FIG. 7E). Magi-1 transcript knockdown using RT-PCR (FIG. 12B) was also verified. Magi-1 protein knockdown was confirmed by immunoblotting (~70-75%) (FIG. 7F) and was comparable to the knockdown achieved in vitro (FIG. 3A,B). Together, these results suggest that Magi-1 regulates nociception and acute inflammatory pain.

$Na_V1.8$ expression decreased after Magi-1 knockdown in vivo. Immunohistochemical analyses of the sciatic nerve and at the Nodes of Ranvier also revealed an unexpected but significant reduction of $Na_V1.8$ immunoreactivity after Magi-1 shRNA treatment when compared to non-coding scrambled shRNA control (FIG. 8A). This finding was corroborated by an observed 75% decrease in $Na_V1.8$ protein expression in DRG neurons after Magi-1 in vivo knockdown (FIG. 8B) as determined by Western blot analysis. These data revealed that in addition to scaffolding channels at the membrane, Magi-1 is required for $Na_V1.8$ protein stability. Recent studies have demonstrated a protective role for Magi-2 in preventing the dendrin from Nedd4-2 mediated protein degradation via a WW mediated interaction. Furthermore, the loss of $Na_V1.8$ protein and the concomitant reduction in phase II inflammatory pain behavior is consistent with the reduced phase II behavior seen in $Na_V1.8$ knockout mice. Using RT-PCR, it was confirmed that $Na_V1.8$ message remained unchanged during Magi-1 knockdown reinforcing the notion that Magi-1 regulates $Na_V1.8$ protein stability (FIG. 12C). These results suggested that Magi-1 play a critical role in regulating ion channel protein stability.

PY motif mimicking peptides regulate $Na_V1.8$ trafficking, DRG neuronal excitability and pain behavior. A PDZ mediated interaction was an absolute requirement for the Slack/Magi-1 interaction (FIG. 1D) was demonstrated. $Na_V1.8$ channels were reported to contain multiple internal putative PDZ binding motifs and bind to the PDZ domain containing protein Pdzd2. However, Pdzd2 knockout mice failed to show any alterations in pain behavior. On the other hand, $Na_V1.8$ channels also contain PY motifs (PPXY (SEQ ID NO:76)) (FIG. 13) at their distal C-termini and this motif was postulated to regulate the interaction with Nedd4-2 ubiquitin ligase for targeted protein degradation. Interestingly, the WW domain of Nedd4-2 shares high sequence homology with the WW domains in Magi-1. Furthermore, Magi proteins have been shown to protect Nedd4-2 target proteins from degradation via WW interaction. Therefore, it was opted to compete off WW domain binding of $Na_V1.8$, using cell-penetrating PY motif peptide mimetics. Two peptides of identical sequence were engineered based on the $Na_V1.8$ WW binding motif except one of the peptides was phosphorylated (representing Thr1926 within the channel). This was done because scanning $Na_V1.8$ with the Phospho-SitePlus® posttranslational modification resource tool revealed that Thr1926, four (4) amino acids adjacent to the PPXY (SEQ ID NO:76) domain, is putatively phosphorylated (FIG. 13). Primary DRG neurons were then treated with 10 µM of the unphosphorylated peptide (PY, myristoyl-SATSFPPSYDSVTRG (SEQ ID NO:77)) or phosphorylated peptide (phospho-PY myristoyl-SATSFPPSYDSV[pT]RG (SEQ ID NO:77, where T is phosphorylated)) to outcompete $Na_V1.8$ channel WW domain binding. Neurons exposed to PY peptide for 24 hrs resulted in an almost complete loss of total $I_{Na}$, while in contrast, the phospho-PY peptide strongly increased peak $I_{Na}$. The PY and phospho-PY peptide showed time-dependent decreases or increases in $I_{Na}$ respectively (6 hrs and, 24 hrs) (FIGS. 9A,B). PY peptide treatment (24 hrs) almost completely abolished AP firing (10 of 11 neurons), whereas the phospho-PY produced contrasting repetitive AP firing (7 of 12) (FIG. 9B). We assessed surface expression of $Na_V1.8$ channels after treatment with the PY peptide was assessed and a substantial decrease of $Na_V1.8$ channels at the plasma membrane was found while there was a significant increase of $Na_V1.8$ membrane expression with phospho-PY peptide (FIG. 9C). Moreover, a substantial decrease was observed in total $Na_V1.8$ protein after incubation with PY peptide suggesting that $Na_V1.8$ protein stability is dependent upon this WW binding motif. These results indicate that the phosphorylation status of the competitor $Na_V1.8$ PY motif peptide was essential for the stabilization of $Na_V1.8$ channels. Furthermore, these data imply that other sodium channels are potentially regulated by PY motif interactions (FIG. 9A,B).

To assess the potential analgesic effects of disrupting sodium channel membrane localization on pain behavior, the impact of the competing peptides in the formalin model of inflammatory pain was investigated. Mice were given a single i.pl. injection of either PY, phospho-PY, or a scrambled PY peptide (100 µM, 20 µl) to the right hindpaw, 24 hrs before injection with 5% formalin into the same paw. Pretreatment with the PY peptide significantly reduced Phase II acute inflammatory pain, and the phospho-PY peptide pretreated mice exhibited a contrasting increase in phase 11 response when compared to scrambled peptide-treated mice (FIG. 9D). These data corroborate what was observed during in vitro experiments and demonstrate a capability of routing $Na_V1.8$ channels in and out of the neuronal membrane using PY motif based peptidomimetics. Additionally, these data suggest that the phosphorylation state of Thr1926 determines $Na_V1.8$ channel trafficking, neuronal excitability, and acute pain behavior.

DISCUSSION: Herein, it is described that Magi-1 is expressed in the pain pathway: high Magi-1 expression was observed in the cell bodies and axons of nociceptive DRG neurons and within the superficial dorsal horn of the spinal cord. Additionally, it was demonstrated that Magi-1 was a critical scaffold for the membrane localization of $Na_V1.8$ and Slack $K_{Na}$ channels in DRG neurons. Both $Na_V1.8$ and Slack $K_{Na}$ channels have been previously implicated in rodent models of inflammatory and neuropathic pain and it has further been shown that Magi-1 interacted with both Slack and $Na_V1.8$ channels. Furthermore, it was found that Magi-1 silencing decreased membrane expression of both types of ion channels resulting in net deficits in DRG neuronal excitability, suggesting that Magi-1 is a critical regulator of ion channel function in neurons. To assess the importance of Magi-1 in pain processing, in vivo silencing Magi-1 shRNAs were transfected into DRG neurons of naïve mice using spinal nerve injection. This is a novel and rapid technique to manipulate gene functioning in the DRG neurons of naïve rodents, in particular mice. It allows for internal control testing of ipsilaterally modified DRG neurons versus unaltered contralateral DRG neurons within the same mouse. Using this in vivo transfection method, it was found that Magi-1 knockdown resulted in significant deficits in thermal nociception and acute inflammatory pain behavior.

Figure 2:
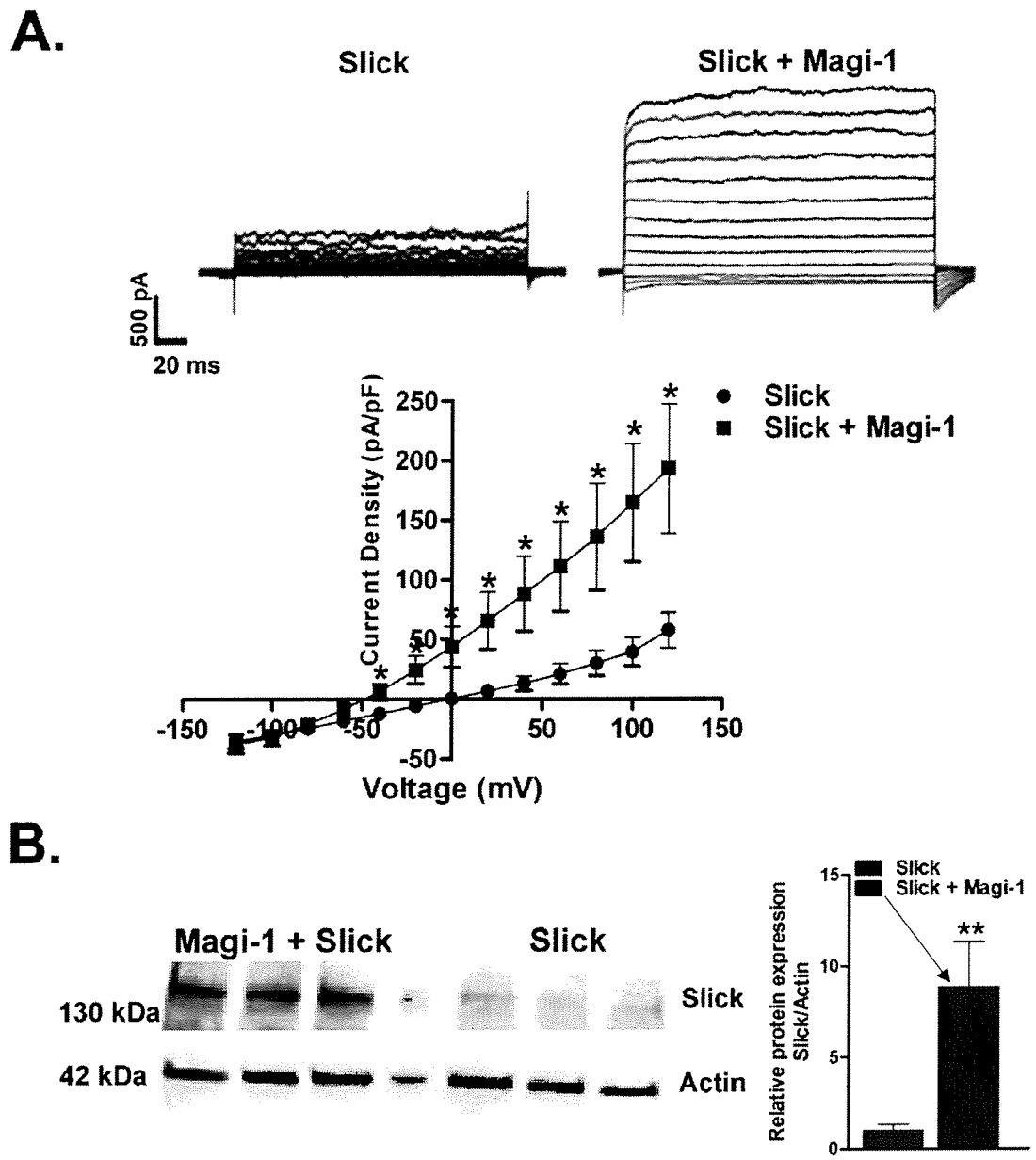
FIG. 2 shows Magi-1 regulates Slick channels in CHO cells. (A) Representative current traces of Slick currents recombinantly expressed with or without Magi-1 in CHO cells (top), (bottom) current density analysis of Slick currents for each condition. 25 cells were analyzed and values expressed as +/−SEM, *p<0.05, vs. respective controls. (B) Immunoblot depicting total increased Slick protein expression during co-expression with Magi-1. Results were taken from three independent cultures and values are expressed as mean+/−SEM (t4=6.152, **p<0.0021, n=3 cultures per group, two-tailed t test). (C) Immunolabeling of recombinant Slick channels and Magi-1 when expressed alone or in combination in CHO cells. (D) Co-immunolabeling of recombinant Slick channels and Magi-1 when expressed in CHO cells.
Figure 2:
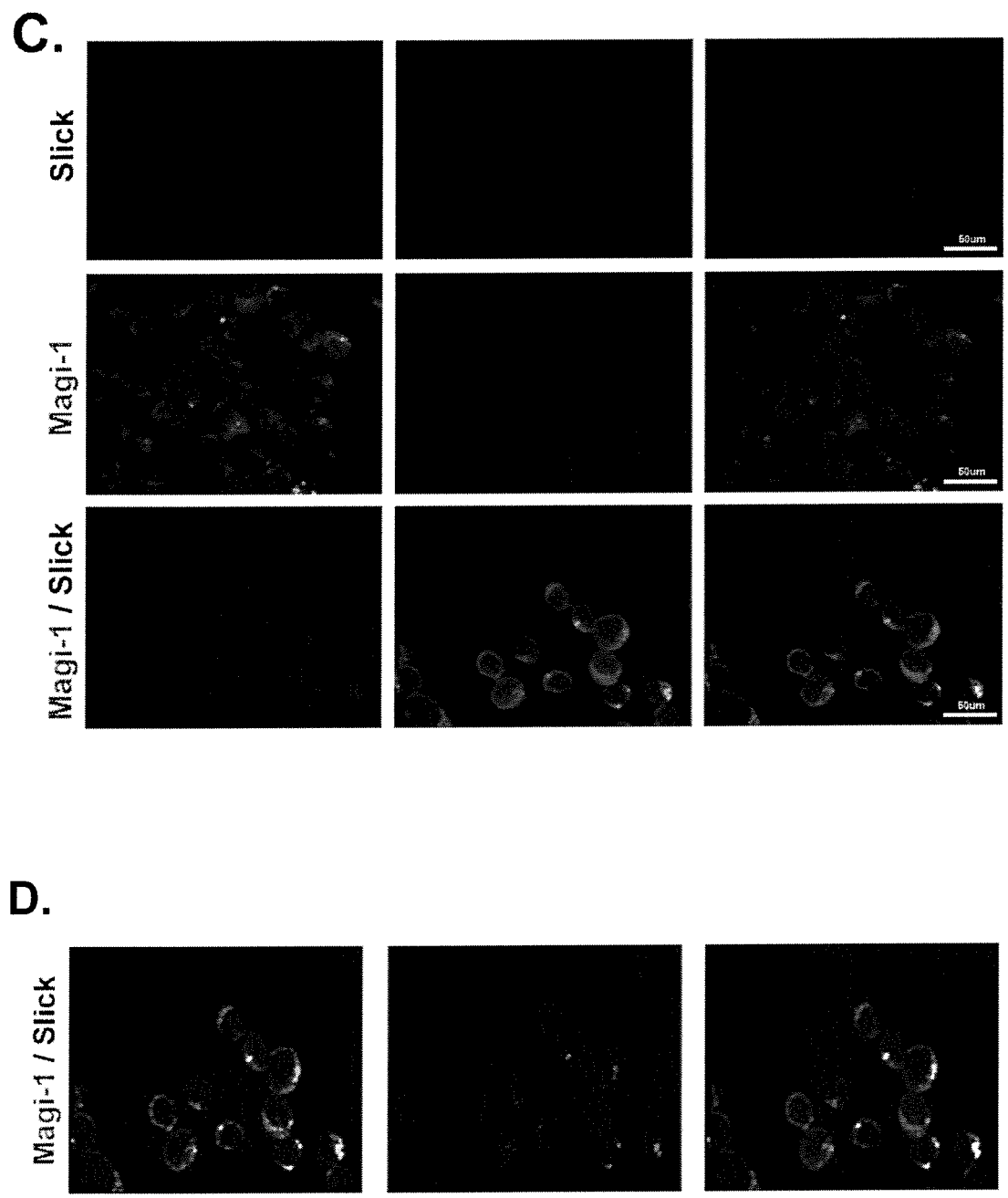

In addition to localizing ion channels to the neuronal membrane, these findings are the first to indicate that Magi-1 is also crucial for ion channel protein stability. Indeed, unlike other scaffolding proteins, the Magi family of proteins may serve a broader function of protecting proteins from degradation. For example, the non-UL YAP1 protein through its WW domain, was shown to protect against Nedd4-2 mediated protein degradation. Subsequently Magi-2 was then reported to protect the protein dendrin also from Nedd4-2 mediated ubiquitination via a WW domain interaction with a conserved PY motif in dendrin. Like dendrin, $Na_V1.8$ has an evolutionarily conserved PY motif that has been demonstrated to be the binding site for Nedd4-2, targeting $Na_V1.8$ for subsequent proteasomal degradation. During prolonged in vivo Magi-1 knockdown, substantial and statistically significant decreases in $Na_V1.8$ immunolabeling and protein expression was observed as determined by immunoblotting (FIG. 8A,B). Likewise, after 24 hrs of PY peptide incubation in DRG neurons, an almost complete loss of $Na_V1.8$ expression was observed. Indeed, $I_{Na}$ density decreased by 50% after just 6 hours suggesting both TTX-resistant and TTX-sensitive $Na_V$ channel membrane expression is dependent upon the PY motif. However, subsequent immunoblotting analysis of $Na_V1.7$ protein showed that while there was some protein reduction was observed during long-term in vivo Magi-1 shRNA knockdown, surface $Na_V1.7$ protein levels were unchanged after peptidomimetic treatment (FIG. 16). It should be noted that embryonic DRG neurons also express $Na_V1.3$ channels, which contain WW binding domains (FIG. 13). So some of the in vitro effects we observed on TTX-sensitive channels might have been attributed to this channel. Nonetheless, these data suggest that there are differential sensitivities for $Na_V$ isoforms to scaffolding and protein stability by Magi-1. Furthermore, it was observed that the Slick $K_{Na}$ subunit, which has a putative PY motif in its N-terminal at amino acids 12-15 (-PPRY- (SEQ ID NO:78)), when recombinantly expressed with Magi-1, produced approximately 5-fold larger currents with concomitant increases in Slick channel protein levels than when the subunit was expressed alone (FIG. 2). This contrasted with the Slack-B subunit for which there is an absence of this PY motif in its N-terminal; membrane currents increased to a lesser extent (2-fold), and no increase in Slack-B protein expression was observed. Indeed, the difficulty in expressing Slick channels compared to Slack channels in heterologous expression systems may be due to this WW binding motif and susceptibility to UL-dependent degradation. Therefore, these results suggest that in addition to membrane targeting Magi-1 also protects ion channels from degradation pathways and indeed targeting Magi-1 represents a novel pharmacological approach to affect ion channel levels and function.

Although both Magi-1 knockdown and the PY peptide caused a reduction in $I_{Na}$, $Na_V1.8$ channel stability and decreased pain behavior, the opposite effects produced by the phospho-PY peptide, specifically the increase in $I_{Na}$, repetitive firing and exacerbation of nocifensive responses, were unexpected. Phosphoproteomic data available online from PhosphoSitePlus® determined that Thr1926 in $Na_V1.8$ channels is putatively phosphorylated. We used this information to design the second peptide, as Thr1926 is four amino acids downstream of the PY motif (FIG. 13). Using the web-based software from Scansite, (MIT), Thr1926 is predicted to be either a Casein 11 kinase or a GSK-3β kinase consensus phosphorylation site. Both kinases are constitutively active kinases suggesting that Thr1926 is likely basally phosphorylated. Without intending to be bound by any particular theory, it is speculated that the phospho-PY peptide competed with phosphorylated $Na_V1.8$ channels at ULs, preventing a significant proportion of $Na_V1.8$ channels from being ubiquitinylated and retained within the cytosol (FIG. 9E). In addition, a statistically significant increase in input levels of $Na_V1.8$ protein over 24 hours was not observed, indicating that at least during this time window the majority of internally localized channels are likely in a monoubiquitinylated state. Without intending to be bound by any particular theory, it is further speculated that dephosphorylated Thr1926 has a higher affinity for Magi-1, which would explain why the competing PY peptide caused a loss of $Na_V1.8$ channels membrane expression. In this case, a substantial decrease in total $Na_V1.8$ channels protein levels was observed, suggesting that within 24 hours, the final fate of channels was degradation. Nevertheless, these results strongly suggest that the PY motif is a primary determinant for $Na_V1.8$ channel trafficking and Magi-1 is a critical component of the sodium signalosome in DRG neurons (FIG. 9E).

Demonstrated herein is a single intradermal injection of the PY peptidomimetic produced significant analgesia 24 hours after administration (FIG. 9D). The PY peptide acted as a local long-lasting analgesic and could have therapeutic value for invasive procedures that require long-lasting analgesia and/or to reduce the need for postsurgical opioids. In contrast the phospho-PY peptide drove $Na_V1.8$ channels to the DRG neuronal membrane and exacerbated nocifensive behavior and therefore has potential value for pain insensitivity-related diseases. Myristoylation allows the peptide to partition through the membrane, possibly by a flip-flop mechanism but keeps most of the peptide tethered to the inner surface of the membrane. This membrane-delimited feature may enhance the ability of peptides to exert their mimetic effects, especially for membrane-associated proteins. In addition to causing cell permeability and anchoring peptides within the inner phospholipid bilayer, myristoylation of peptides and their inherent hydrophobic nature likely ensure that peptides are localized to the site of injection. Moreover, the metabolism of these peptides requires phospholipid membrane turnover possibly contributing to their long-lasting effects in vivo. Prior studies using a similar intradermal injection approach of a peptidomimetic for the T-mem100 protein, important for the TRPA1-TRPV1 complex, showed an analgesic effect during paclitaxel-induced chronic pain. Therefore, the use of myristoylated cell-penetrating peptides offers a potential therapeutic approach to manipulate nerve-ending activity.

In addition to the high expression of Magi-1 in peripheral DRG neurons, Magi-1 is also robustly expressed within the central nervous system. Therefore, scaffolding and membrane stabilization of $Na_V1.8$ and Slack $K_{Na}$ channels by Magi-1 in DRG neurons might similarly occur with TTX-sensitive, WW binding motif containing $Na_V$ channels within central neurons. Indeed, these data showed that Magi-1 knockdown in cultured DRG neurons also resulted in a significant reduction in the TTX-sensitive $I_{Na}$ possibly because multiple $Na_V$ channel isoforms contain WW-binding domains (FIG. 13). $Na_V$ channel loss-of-function mutations are linked with mental health disorders. These findings may help resolve why Magi-1 deficiency is also associated with multiple psychiatric syndromes because Magi-1 deficiency causes diminished sodium transport and hypoexcitability. It is expected phospho-PY peptide could serve as a novel therapeutic platform to increase excitability in neurological diseases associated with hypoexcitability.

EXPERIMENTAL PROCEDURES: Animals—All animals used in the present study were housed at the University at Buffalo (UB) Laboratory Animal Facility on a 12/12 light/dark cycle with free access to food and water. All experimental procedures were in accordance with the guidelines in "Guide for the Care and Use of Laboratory Animals" from the National Institute of Health and were approved by the University at Buffalo Institutional Animal Care Use Committee.

Primary DRG neuronal cultures—Timed-pregnant Sprague-Dawley rats (Harlan, Indianapolis, Ind.) were used for culturing neurons. On the day of the dissection, rats were euthanized by $CO_2$ asphyxiation and E15 embryos were extracted. DRG neurons were dissected from the embryos and enzymatically digested with Trypsin (2.5 mg/ml) at 37° C. for 45 min, followed by dissociation and plating. DRG neurons were plated onto poly-D-lysine (Sigma; 100 µg/ml) and laminin (Invitrogen; 3 µg/ml) coated coverslips. Neurons were maintained at 37° C. in a 7% $CO_2$ humidified incubator in serum-free medium, comprised of the trophic factors $N_2$ (Gemini Bio products; 1%), I-Glutamine (Invitrogen; 200 sg/ml), and Nerve Growth Factor (NGF) (Harlan; 100 ng/ml; essential for embryonic neuronal survival) in 50% DMEM and 50% F-12. The reliance of embryonic DRG neurons on NGF selects for the small-diameter population that is thought to underlie nociception and thermoception. Two successive days after DRG dissection, DRG neurons were cultured in C2 media containing the antimitotic agent cytosine β-d-arabinofuranoside hydrochloride (Sigma; 3 µM). This was followed by two days of recovery were neurons received regular serum free media before neurons were used for experiments. All subsequent experiments using embryonic cultures were performed on days 5-10 of neuronal culture.

Cell culture—Chinese Hamster Ovary (CHO) cells were cultured at 37° C. in 5% $CO_2$ in Iscove's Modified Dulbecco's Medium (IMDM) supplemented with 10% FBS, 1% hypoxanthine/thymidine (HT) supplement (Life Technologies) and 1% penicillin-streptomycin. CHO cells were plated on 12 mm coverslips for immunolabeling experiments, in 35 mm dishes for all electrophysiology experiments, and in six-well culture plates for biochemical experiments. Cells were co-transfected with either 0.5 µg Slick (pTRACER) or 0.5 µg Slack (pTRACER) plus 0.5 µg Magi-1 (pcDNA3.1; Addgene) or 0.5 µg empty vector using lipofectamine (ThermoScientific) as per manufacture's guidelines. The Magi-1 clone was mutated to include a Kozak sequence at the 5' end to boost protein expression.

DRG siRNA Transfection—Small interfering RNA (siRNA) directed against Magi-1 was purchased from Santa Cruz Biotechnology (Santa Cruz, Calif., USA). A negative control siRNA composed of a scrambled sequence was obtained from the same vendor. For each experiment, neurons were transfected with Magi-1 siRNA or a non-targeting control siRNA. Cultured DRG neurons (described above) were transfected using lipofectamine 2000 (ThermoScientific) following the manufacturer's protocol. Briefly, we diluted 1.5 µl lipofectamine 2000 in 50 µl of Opti-mem Medium and allow the mixture to sit at room temperature for 5 minutes. After 5 minutes this mixture was combined with 40 pmol of scrambled or Magi-1 siRNA (three different siRNA duplexes pooled) in 50 µl of Opti-mem, the mixture was allowed to incubate at room temperature for 30 minutes before being added to cells plated on 12 mm coverslips in 24 well plates. The siRNA mixture added to the DRG culture media was allowed to incubate with DRG neurons for 48-72 hours before being used for electrophysiological recordings. For Western Blotting, 300 pmoles of siRNA was used in each six well plate. siRNA transfected DRG neurons were used in experiments 48-72 hrs. post-transfection. For electrophysiological experiments, DRG neurons were co-transfected with the GFP containing plasmid pTRACER and siRNA duplexes for positive indication of transfection. Immunofluorescence procedures on cultured neurons were performed as previously described. Investigator was blinded to the transfection condition.

Electrophysiology—All data was acquired using the Axopatch 200B amplifier (Molecular Devices,) and Multiclamp-700B (Molecular Devices, Sunnyvale, Calif.), digitized and filtered at 5 kHz. Data acquisition was monitored and controlled using pClamp 10 (Molecular Devices). Whole-cell patch-clamp recordings were performed on cultured DRG neurons, and CHO cells transiently transfected with WT or mutated Slack with Magi-1. Glass electrodes were pulled using a vertical pipette puller (Narishige International USA, Amityville, NY) and fire polished to be of 5-8 MΩ resistance. Pipettes were filled with solution containing (in mM) 124 K-gluconate, 2 $MgCl_2$, 13.2 NaCl, 1 EGTA, 10 HEPES, 4 Mg-ATP, and 0.3 Na-GTP at pH 7.2 for neuronal recordings, and with 32.5 mM KCl, 97.5 mM potassium gluconate, 5 mM EGTA and 10 mM HEPES (pH 7.2) for CHO cell Slack and Slick recordings. The bath solution for all cells contained (in mM) 140 NaCl, 5.4 KCl, 1 $CaCl_2$, 1 $MgCl_2$, 10 HEPES, and 10 glucose (pH 7.4). Identical bath and pipette solutions were used in both the voltage-clamp and current-clamp modes. In voltage-clamp mode, macroscopic currents were recorded at voltages ranging from −120 to +120. Cells were clamped at −70 mV and voltage steps of 20 mV applied for 200 millisecond durations. The cell capacitance for CHO cells ranged from 10-15 pF and for cultured DRG neurons 20-25 pF recorded under these conditions. A current-clamp protocol consisting of depolarizing steps in increments of 10 pA from 10 to 200 pA (20 ms duration) was used to examine action potential firing. Firing frequency of individual neurons was assessed by measurement of repetitive discharge upon injecting of a suprathreshold stimulus of 400 pA for 1000 ms. For $I_{Na}$ recordings, the pipette solution contained (in mM): 130 CsCl, 13 CsF, 10 tetraethylammonium chloride, 1 $MgCl_2$, 1 EGTA, 2.5 $Na_2ATP$, 10 HEPES, pH was adjusted to 7.2 with CsOH. The bath solution contained (in mM) 140 NaCl, 5.4 KCl, 1 $CaCl_2$), 1 $MgCl_2$, 10 HEPES, and 10 glucose (pH 7.4). For TTX-resistant $I_{Na}$, DRG neurons were recorded in a bath solution containing 250 nM TTX. DRG neurons were recorded at voltages ranging from −60 to +60 mV. Cells were held at −70 mV and $I_Na$ was evoked by incremental 10 mV depolarizing steps for 50 ms duration.

Immunohistochemistry—Sciatic nerve (SN), lumbar spinal cord (SC), lumbar, and thoracic DRGs were isolated from adult mouse. Briefly, animals were anesthetized with fetal plus, perfused transcardially with iced cold PBS containing heparin (50 µg/ml) and sodium nitrite (5 mg/ml) followed by iced cold 4% paraformaldehyde (PFA). DRGs, SN, and SC were subsequently removed, cleaned of surrounding tissue and post-fixed in 4% PFA overnight at 4° C. The following day, SN and DRGs were transferred to 20% sucrose (Cryoprotect). After two days DRGs, SN and SC were removed from sucrose and embedded in freezing media and store at −80° C. for future use. 16 µm sections of DRGs, 10 μm sections of SN, and 20 μm sections of SC were made using a cryostat. Slices were permeabilized with a PBS solution containing 0.4% Triton X-100. Sections were then blocked for 2 hr at room temperature with PBS containing 5% BSA. Then sections were incubated with a mixture of primary antibodies in PBS containing 5% BSA overnight at 4° C. All primary antibodies were previously validated which included: mouse anti-$Na_V1.8$ antibody (1:250; NeuroMab), rabbit anti-Magi-1 antibody (1:100; Abcam), mouse anti-Magi-1 antibody (1:100; Novus Biochemical), rabbit anti-Caspr (1:250; Abcam) and chicken anti-Slack antibody (1:750). After several rinses, secondary antibodies Alexa Fluor 633 goat anti-mouse, Alexa Fluor 488 goat anti-rabbit, and Alexa Fluor 546 goat anti-chicken were added (1:1000) overnight. Coverslips were then mounted on slides using Prolong Gold antifade reagent with 4',6'-diamidino-2-phenylindole dihydrochloride. Cell size characterization of Magi-1 immunolabeling was analyzed using the MetaMorph software (Molecular Devices).

Western Blot Analysis—Total proteins were collected from transfected CHO cells, spinal cord and DRG. Tissue was homogenized in RIPA buffer supplemented in protease inhibitor cocktail (Sigma). Immunoblotting was performed as previously described. Briefly, proteins were separated on 4-15% Mini-PROTEAN TGX Precast Gel (Bio-Rad) and transferred to a 0.45 μm nitrocellulose membrane (BioRad). Membranes were probed overnight at 4° C. with antibodies against Slack anti-mouse (1:500; NeuroMab), rabbit anti-β-Actin (1:500; Millipore), rabbit anti-Magi-1 (1:100; Abcam), mouse anti-Magi-1 (1:100; Novus Biochemical), mouse anti-$Na_V1.8$ (1:200; NeuroMab), mouse anti-$Na_V1.7$ (1:200; NeuroMab), mouse anti-Flag (1:500; Sigma) in 5% milk prepared in 1×Tris-buffered saline tween (TBST). On the following day, the membrane was washed three times for five minutes in 1×TBST before being incubated for 1 hour at room temperature in Anti-mouse or Anti-rabbit horseradish peroxidase conjugate (1:5000; Promega) and 0.1% BSA prepared in 1×PBS. The membrane was again washed 3 times for 5 minutes before being developed and imaged. Bands were visualized with enhanced chemiluminescence (Thermo Scientific) and quantified with Image J Software (NIH). Each experiment was repeated at least three times.

Co-Immunoprecipitation—CHO cells in six-well plates were transiently transfected with WT or mutated Slack with or without Magi-1 plasmids respectively. Cells were then lysed with 100 μl/well ice-cold RIPA buffer supplemented with protease inhibitor cocktail (Sigma). 60 μl/well of Protein G-linked Sepharose bead slurry (GE Healthcare) was washed three times with ice-cold lysis buffer and incubated on a rotator overnight at 4° C. with 4 μg of rabbit Magi-1 antibody (Abcam) or mouse anti-Slack antibody (neuroMab) in PBS with 0.1% Tween-20 and cell lysate (3 wells/sample). On the following day, samples were centrifuged and supernatants were stored separately. Pellets were washed three times with cold lysis buffer and bound protein was eluted via boiling three times at 9° C. for 8 min. each. Samples were centrifuged to separate proteins into the supernatant, which was then denatured with Sodium Dodecyl Sulfate (SDS) and loaded onto a Ready Gel (Bio-Rad) (4-15% Tris-HCl) as the immunoprecipitate. The supernatants collected and whole cell lysate (total input) were also denatured with SDS and run as controls. Samples were probed for Slack or $Na_V1.8$ and actin protein by Western blot, as described above.

Surface Protein Biotinylation—Plasma membrane protein expression was detected using a protein biotinylation assay. Briefly, CHO cells or DRG neurons in six-well plates were used at 48 h after transient transfection of plasmid constructs or Magi-1 targeting siRNA respectively. For peptide incubation, neurons were incubated for 24 hrs. 160 μl of 10 mM Sulfo-NHS-SS-Biotin (Thermo Scientific) was added to each well and incubated at room temperature for 45 mins. The biotinylation reaction was terminated using 10 mM glycine (Quenching solution). Cells were harvested, washed in TBS and lysed on ice for 30 minutes in a lysis buffer/protease inhibitor cocktail. Lysates were collected and incubated with 500 uL of NeutrAvidin Agarose for 60 mins at room temperature with rotation. Following incubation, the column underwent centrifugation to collect the unbiotinylated protein. To elute the biotinylated proteins, sodium dodecyl sulfate (SDS) and dithiothreitol (DDT) were added to column membrane and incubated with rotation for 1 hour at room temperature. Biotinylated and unbiotinylated samples were probed for Slack or $Na_V1.8$ and Actin protein by Western blot, as described above.

Nociception Testing—Baseline thermal nociceptive behavior was measured using the automated Hargreaves Apparatus by Ugo Basile (Varese, Italy). Naïve C57Bl/6 Mice (8-10 weeks) (Envigo) underwent two days of habituation followed by three days of measurements. On days 1 and 2 (habituation), mice spent 30 min in homecages adjusting to the testing room and were then transferred to testing chambers for 1 hr. On days 3 through 5, mice underwent testing. An infrared stimulus (IR 40) was delivered through the plexiglass floor to the plantar surface of the hind paw, and the latency to withdrawal was measured automatically. For each subject, three to six measurements per hind paw were taken and used to calculate the average latency to withdraw (seconds). A maximum IR exposure time of 15 s was established to ensure no tissue damage occurred, and at least 5 min was allowed between measurements taken from the same mouse.

In vivo transfection with jetPEI®/Magi-1 shRNA plasmid DNA polyplexes—The spinal nerve injection protocol was adopted from and optimized for spinal nerve injection in mice. Three days after baseline thermal behavior was established, mice were anesthetized using isoflurane (induction: 4% and maintenance: 2%), and placed in a prone position. A 3-cm posterior longitudinal skin incision was made at the lumbar segment of the spine. The ipsilateral paraspinal muscles were carefully separated, using a pair of sterile toothpicks, from their attachments at the L4~S1 levels of the vertebral column. 1.5 μl of PEI/shRNA plasmid DNA polyplexes at an N/P ratio of 6 were injected directly in the spinal nerve of the right hind paw slowly using a syringe connected to a 26-gauge needle (Hamilton 80030, Hamilton, Reno, NV). Magi-1 shRNAs and control shRNA were purchased from Santa Cruz Biotechnology (Santa Cruz, CA, USA) and were identical to the siRNA sequences described above. After injection, the needle was held at the spinal nerve for 1 min to prevent leakage. Complete hemostasis was confirmed, and the wound was sutured with wound clips. Mice were allowed to recover for 7 days before thermal nociceptive behavior was tested again.

Formalin test—Mice were habituated in the behavior room for 15 minutes, then 30 minutes in the formalin chamber before formalin injection. 20 microliters of 5% formalin (in sterile saline) was injected intraplantarly into the right hind paw and mice were placed back in chamber for video recording. The total time spent lifting, the total number of licks, and the number of flinches were recorded in 5 minute intervals for 60 minutes. The measurements from two observers blinded to the experimental condition for each video recording were averaged to obtain final measurements at each time point.

RNA Extraction and cDNA Synthesis—RNeasy Micro Kit (Qian) was used for total RNA extraction from mouse lumbar DRG neurons. RNA was reverse transcribed with SuperScript III Reverse Transcriptase (Life Technologies). Polymerase chain reaction was performed using this cDNA as the template with previously validated primers against Magi-1 and $Na_V1.8$. Transcriptional abundance was measured by thermocycler using SYBR Green PCR Master Mix. For quantification, a 50 cycle two step denaturing and annealing protocol was used, with a 15 second absorbance reading on BioRad iQ5 cycler. Each sample was performed in triplicates.

Peptides—We designed the N-terminal myristoylated PDZ peptide peptidomimetic NPETRDETQL (SEQ ID NO:79) based upon the C-terminal sequence of the rat Slack channel. This peptide and the scrambled variant peptide, QPNTRLDETE (SEQ ID NO:80), were synthesized by GenScript. Similarly, the PY peptide SATSFPPSYDSVTRG (SEQ ID NO:77) and the phospho-PY peptide SATSFPPSYDSV(pT)RG (SEQ ID NO:77, where T is phosphorylated) were designed based upon the WW binding domain in rat $Na_V1.8$ channels. These peptides and the scrambled peptide SDRPVTSYSFSAPG (SEQ ID NO:81) were also synthesized by GenScript. Peptides were initially dissolved in DMSO and diluted to final working concentration in saline. Peptide concentration of 10 μM was used on primary neurons as previously described; final DMSO concentration was 0.05%. Intraplantar dosing was chosen based on a prior study demonstrating the analgesic effects of hindpaw intradermal injections of a different myristoylated peptide.

For optional phospho-threonine peptides, threonine is protected by trityl ethers [Fmoc-Thr(Trt)-OH]. The trityl-protected derivatives can be selectively deprotected on resin, which is useful for preparing and phosphothreonine-containing peptides by global phosphorylation methodology. Global phosphorylation involves selective phosphitylation of the appropriate hydroxyl threonine on the solid phase, with a protected phosphoramidite, followed by oxidation of the resultant P(III) triester to the P(V) triester. Finally, myristoylation was achieved by N-myristoyltransferase, the enzyme that catalyzes protein N-myristoylation (at the N-terminus).

Statistics—Clampfit (Molecular Devices) and Origin 8.0 (Origin Lab) software were used for all electrophysiology data analysis. Densitometry analyses of Western blots were done using Image J (NIH) software. Statistical analysis was done using GraphPad Prism 4 (GraphPad, San Diego, CA). Single between group comparisons were made using Student's t-test. Multiple comparisons were investigated using one-way or two-way ANOVA followed by Bonferroni's test to detect pair wise between-group differences. Data are presented as mean+/−SEM.

RNA Extraction and cDNA Synthesis for Real Time PCR. RNeasy Micro Kit (Qiagen) was used for RNA extraction from neuronal culture. RNA was reverse transcribed with SuperScript III Reverse Transcriptase (Life Technologies) into cDNA and used for subsequent RT-PCR. Transcriptional abundance was measured by thermocycler using SYBR Green PCR Master Mix. For quantification, a 50 cycle two step denaturing and annealing was used, with a 15 second absorbance reading on BioRad iQ5 cycler. Each sample was performed in triplicate. Primers for RT-PCR are listed below:

```
Magi-1 Primers
                                      (SEQ ID NO: 82)
5-GTCTTCGAGGGGGCCGAGAATATAACATGG-3

(SEQ ID NO: 83)
5-GGTGGAGGGGCCGTTCCTGTCG-3

Nav1.8 Primers
                                      (SEQ ID NO: 84)
5' CCCAAAGGGCAGCAGGAGCTG-3'

(SEQ ID NO: 85)
5'-CGGCGAGTGCAGCCTTCTGTGA-3'

(SEQ ID NO: 86)
5'-CTGCCACAAGTCCAAAAGTGTGAA-3'

(SEQ ID NO: 87)
5'-AGTCATCGGGCTCGTCCAGATC-3'
```

Plasmid DNA encoding MAGI-1 shRNAs for humans. To make a therapeutic shRNA for pain treatment, we would screen the human Magi-1 mRNA sequence for 3 unique interfering RNA sequences, and then each one of those sequences (in DNA form) would be inserted into a plasmid containing the minimal promoter for the human $Na_V1.8$ channel, thus creating 3 plasmids. Expression of the shRNA driven under the minimal $Na_V1.8$ channel promoter would ensure that that Magi-1 targeted shRNAs are only expressed in pain sensing neurons.

Although the present disclosure has been described with respect to one or more particular embodiments and/or examples, it will be understood that other embodiments and/or examples of the present disclosure may be made without departing from the scope of the present disclosure.

The invention claimed is:

1. A method for treating pain comprising:
   a) a subject in need of treatment for pain;
   b) administering to said subject a therapeutically effective amount of a composition selected from the group consisting of a fifteen amino acid peptide having the sequence of $X^1X^2X^3X^4X^5PPSYX^8X^9VX^{10}X^{11}X^{12}$ (SEQ ID NO:114) and a MAGI-1 antisense ribonucleic acid; and
   c) reducing said pain of said subject.

2. The method of claim 1, further comprising administering one or more analgesic agent and/or one or more anesthetic agent.

3. The method of claim 1, wherein said pain is caused by a particular condition selected from the group consisting of an injury, a chronic disease, a chronic inflammation, Morton's neuroma, operative/post-operative pain and a combination thereof.

4. The method of claim 3, wherein said injury is selected from the group consisting of a spinal cord injury, a nerve injury, a burn injury and any combination thereof.

5. The method of claim 3, wherein said chronic disease is selected from the group consisting of diabetes, Herpes zoster, major depressive disorder, fibromyalgia arthritis, amyotrophic lateral sclerosis, multiple sclerosis, schizophrenia, autism spectrum disorders, cancer and a combination thereof.

6. The method of claim 1, wherein said MAGI-1 antisense ribonucleic acid is a sequence selected from the group consisting of SEQ ID NOs: 88-98 and combinations thereof.

7. The method of claim 1, wherein said peptide has a sequence selected from the group consisting of SEQ ID NOs:1-4, 6, 7, 15-18, 20-21 and combinations thereof.

8. The method of claim 7, wherein said pain is ameliorated for 1-120 hours.

9. The method of claim 7, wherein said pain is ameliorated for 24-120 hours.

10. The method of claim 7, wherein said SEQ ID NO:6,- SEQ ID NO:7, SEQ ID NO:20, and SEQ ID NO:21 further comprise an N-terminal myristoyl group.

* * * * *